United States Patent
Cashman et al.

(10) Patent No.: US 10,874,766 B2
(45) Date of Patent: Dec. 29, 2020

(54) COMPOUNDS AND MATRICES FOR USE IN BONE GROWTH AND REPAIR

(71) Applicant: HUMAN BIOMOLECULAR RESEARCH INSTITUTE, San Diego, CA (US)

(72) Inventors: John R. Cashman, San Diego, CA (US); Daniel R. Ryan, San Diego, CA (US); Sigeng Chen, San Diego, CA (US)

(73) Assignee: Human Biomolecular Research Institute, San Diego, CA (US)

( * ) Notice: Subject to any disclaimer, the term of this patent is extended or adjusted under 35 U.S.C. 154(b) by 0 days.

(21) Appl. No.: 14/776,995

(22) PCT Filed: Mar. 17, 2014

(86) PCT No.: PCT/US2014/030912
§ 371 (c)(1),
(2) Date: Sep. 15, 2015

(87) PCT Pub. No.: WO2014/146039
PCT Pub. Date: Sep. 18, 2014

(65) Prior Publication Data
US 2016/0038641 A1 Feb. 11, 2016

Related U.S. Application Data

(60) Provisional application No. 61/801,347, filed on Mar. 15, 2013.

(51) Int. Cl.
| | | |
|---|---|---|
| *C07C 229/40* | (2006.01) | |
| *C12Q 1/6883* | (2018.01) | |
| *A61L 27/38* | (2006.01) | |
| *A61L 27/12* | (2006.01) | |
| *C07D 215/44* | (2006.01) | |
| *C07D 487/04* | (2006.01) | |
| *A61K 31/519* | (2006.01) | |
| *A61K 33/42* | (2006.01) | |
| *A61K 38/18* | (2006.01) | |
| *A61K 31/4706* | (2006.01) | |
| *A61K 31/12* | (2006.01) | |
| *A61K 45/06* | (2006.01) | |
| *A61K 35/28* | (2015.01) | |
| *G01N 33/50* | (2006.01) | |
| *A61L 27/28* | (2006.01) | |
| *A61L 27/32* | (2006.01) | |

(Continued)

(52) U.S. Cl.
CPC .......... *A61L 27/3895* (2013.01); *A61K 31/12* (2013.01); *A61K 31/4706* (2013.01); *A61K 31/519* (2013.01); *A61K 33/42* (2013.01); *A61K 35/28* (2013.01); *A61K 38/18* (2013.01); *A61K 45/06* (2013.01); *A61L 27/12* (2013.01); *A61L 27/28* (2013.01); *A61L 27/32* (2013.01); *A61L 27/3834* (2013.01); *A61L 27/3847* (2013.01); *A61L 27/425* (2013.01); *A61L 27/54* (2013.01); *A61L 27/58* (2013.01); *C07C 49/248* (2013.01); *C07C 49/255* (2013.01); *C07C 225/22* (2013.01); *C07C 229/40* (2013.01); *C07D 215/44* (2013.01); *C07D 487/04* (2013.01); *C12Q 1/6883* (2013.01); *G01N 33/502* (2013.01); *G01N 33/5044* (2013.01); *A61L 2300/112* (2013.01); *A61L 2300/412* (2013.01); *A61L 2300/606* (2013.01); *A61L 2300/64* (2013.01); *A61L 2400/18* (2013.01); *A61L 2420/02* (2013.01); *A61L 2420/06* (2013.01); *A61L 2430/02* (2013.01); *A61L 2430/40* (2013.01); *C12Q 2600/136* (2013.01); *C12Q 2600/158* (2013.01); *G01N 2333/916* (2013.01)

(58) Field of Classification Search
None
See application file for complete search history.

(56) References Cited

U.S. PATENT DOCUMENTS

| | | | | |
|---|---|---|---|---|
| 6,462,019 B1 * | 10/2002 | Mundy | ............... | A61K 8/64 |
| | | | | 435/69.2 |
| 2003/0009235 A1 * | 1/2003 | Manrique | ............ | A61B 17/866 |
| | | | | 623/23.63 |

(Continued)

FOREIGN PATENT DOCUMENTS

| | | |
|---|---|---|
| WO | WO-2006-000576 A2 | 1/2006 |
| WO | WO-2010-086040 A1 | 8/2010 |

OTHER PUBLICATIONS

Sandur, Carcinogenesis, 28, 8, 2007.*

(Continued)

*Primary Examiner* — Susan T Tran
*Assistant Examiner* — William Craigo

(57) ABSTRACT

Compositions of small molecules, matrices, and isolated cells including methods of preparation, and methods for differentiation, trans-differentiation, and proliferation of animal cells into the osteoblast blast cell lineage were described. Examples of osteogenic materials that were administered to cells or co-cultured with cells are represented by compounds of Formula II, IV, and VI independently or preferably in combination with a matrix to afford bone cells. Small molecule-stimulated cells were also combined with a matrix, placed with a cellular adhesive or material carrier and implanted to a site in an animal for bone repair. Matrix pretreated with compounds of Formula II, IV, and VI were also used to cause cells to migrate to the matrix that is of use for therapeutic purposes.

10 Claims, 6 Drawing Sheets

(51) Int. Cl.
  *A61L 27/42*  (2006.01)
  *A61L 27/54*  (2006.01)
  *A61L 27/58*  (2006.01)
  *C07C 49/248* (2006.01)
  *C07C 49/255* (2006.01)
  *C07C 225/22* (2006.01)

(56) References Cited

U.S. PATENT DOCUMENTS

| | | |
|---|---|---|
| 2004/0132724 A1 | 7/2004 | Bladh et al. |
| 2011/0206645 A1* | 8/2011 | Zhang ............ A61K 31/4545 424/93.7 |
| 2012/0004197 A1 | 1/2012 | Ashikawa et al. |
| 2012/0040976 A1 | 2/2012 | Cashman et al. |

OTHER PUBLICATIONS

Mujtaba International Journal of Molecular Medicine, 29, 2012.*
Buhrmann, Arthritis Research and Therapy, 12, R127, 2010 (Year: 2010).*
International Search Report for PCT/US2014/030912 (in English), dated Oct. 27, 2014; ISA/KR.
Ghosh-Choudhury, N. et al. "Immortalized murine osteoblasts derived from BMP 2-T-antigen expressing transgenic mice" Endocrinology (1996) 137(1): 331-339.
Kamiya, N. and Mishina, Y. "New insights on the roles of BMP signalling in bone—A review of recent mouse genetic studies" Biofactors (2011) 37(2): 75-82.

* cited by examiner

COMPOUNDS AND MATRICES FOR USE IN BONE GROWTH AND REPAIR

CROSS REFERENCE TO RELATED APPLICATIONS

This application claims the benefit of U.S. Provisional Patent Application Ser. No. 61/801,347, filed Mar. 15, 2013, the entire content of which is hereby incorporated by reference in its entirety.

FIELD OF THE INVENTION

The disclosure relates generally to compositions of compounds and matrices and isolated cells that are improved compositions for use in cell therapy and tissue engineering of bone or cartilage or their progenitor tissues. In another respect, the disclosure provides methods for using compositions of compounds and matrices and/or isolated cells to promote bone formation in vivo. In another respect, the disclosure provides a method for compound screening to identify compounds and matrices that when used together potently stimulate formation of bone or cartilage or their progenitor tissues. More specifically, animal cells (preferably human cells optimally cultured in the presence of serum and/or cell co-culture) are induced in the presence of small molecule and matrix to commit to the osteogenic lineage and to increase cell osteogenesis by increasing adherence of cells to the matrix, cell proliferation, cell differentiation and mineralized protein deposition. In another respect, matrices pretreated or adsorbed with small molecules are used to increase cell adherence to the matrix that are implantable compositions that improve cell engraftment of animal cell therapy or tissue engineering approaches to bone or cartilage formation. Fundamentally, the invention uses small molecules in the presence of a matrix to modulate cells through defined biological pathways. Together the small molecule/ matrix/cell combination constitutes a microenvironment that supports osteogenesis and can be used either for in vitro preparation of implantable compositions to generate bone or cartilage or their progenitor tissues in vivo, or for direct in vivo administration of the small molecule and/or matrix to effect endogenous cells for use in bone or cartilage formation or repair.

BACKGROUND OF THE INVENTION

Bone is a dynamic tissue because its homeostasis represents a balance between bone formation and bone resorption. In bone formation, adult stem cells differentiate into bone progenitor cells (i.e., osteoprogenitor cells) that have the ability to mature into osteoblasts, osteocytes, and form mature bone and mineralized matrix that is the hard tissue of bone. Endogenous mesenchymal stem cells (MSCs) that contribute to bone formation are most prominently found in the bone marrow, but these bone marrow-derived mesenchymal stem cells (also known as bone marrow-derived stromal stem cells, BMSCs) are relatively scarce. MSCs have also been identified and harvested from adipose tissue, cartilage tissue, blood, umbilical cord blood, muscle tissue, dental pulp, and corneal stromal tissue. Cell isolates from bone, whether intramembranous or endochronal bone in origin, often contain MSCs and osteoprogenitor cells, or a mixture of MSCs and osteoprogenitor cells that give rise to bone. Also, isolated embryonic stem cells and induced pluripotent stem cells are capable of producing bone, although normally adult stem cells are the endogenous source of cells for bone formation. However, MSCs by themselves and stem cells in general, are capable of adopting other, non-osteogenic cell lineages or tissues, and these cells by themselves are not very efficient at migrating to the site of injury required for bone formation. This disclosure provides novel compositions and methods that can be used to induce cell lineage commitment.

In bone resorption, osteoclasts (cells that resorb bone tissue) dissolve the mineralized matrix and create cavities on the bone surface. The balance between bone formation and bone resorption is instrumental in the maintenance of healthy bones, but maintenance of healthy bone often declines with age. Imbalance of bone formation and resorption usually causes loss of bone mass and eventually leads to bone related diseases, such as osteoporosis, rickets, and osteomalacia. These bone diseases are associated with increased risk of bone fractures, increased severity of fractures, protracted time periods for healing, and worsened patient outcomes, all of which can result in life-threatening complications. Additionally, with age or injury the incidence of disc degenerative disease or deformity of the spine is increased, leading to spondylolithesis with accompanying severe pain that can be dehabilitating for individuals afflicted with these conditions. The invention disclosed herein provides for a method to treat some of these conditions.

Bone grafts where bone is harvested from a patient (e.g., from the hip, leg, or calvarial bones) and re-applied to a bone defect, fracture, or void represents the "gold standard" for repair of bone injuries that cannot be efficiently repaired through natural processes. The benefits are that the graft substance contains a mixture of MSCs, osteoprogenitor cells, growth factors and mineralized protein matrix that stimulate bone growth, remodeling, and biointegration. However, the amount of graft substance available to fill a bone defect is fundamentally limited by the amount of bone that can be harvested from a patient and the bone harvest procedure has been associated with patient morbidity, surgical blood loss, and is not generally suitable for patients with an underlying bone disease that compromises the quality of the graft. Also, the ability of MSCs to produce bone has been proposed to decline with age, potentially further limiting the patient eligibility pool. Grafting of allogeneic MSCs from a donor individual avoids the harvesting procedure of autografts, but offers no apparent advantages over autologous MSCs in terms of capacity to form bone once transplanted to the patient in that they still require signals or stimulus. Artificial biomaterials have shown promise as bone graft alternatives, however, most biomaterials have poor biointegration (do not resorb) and brittleness due to the lack of biological components in the composition.

Cell therapy and tissue engineering can be used as an approach to bone formation that overcomes many of the forestated limitations. Allogeneic or autologous stem cells can be harvested, purified, and expanded to provide sufficient cell numbers for implantation or injection to a site where bone formation is desired in vivo. However, additional signals or stimulus are required to form robust bone and for MSCs to efficiently engraft at the site of bone injury. The choice of cell carrier material for implantable/injectable cell therapies can significantly impact the efficiency and quality of bone growth, as well as biointegration through remodeling of the carrier substance. Improved vascularization and hematopoiesis of a site of bone formation has also been associated with improved bone growth. Accordingly, the role of the biological niche or microenvironment of stem cells plays a critical role by providing the signals, stimuli, and biological factors that promote bone formation and repair.

Growth factors including bone morphogenetic proteins (BMPs) have been used to repair bone in various applications, such as in spinal fusion procedures of the lumbar spine that may arise through degenerative disc disease. Also, recombinant BMP-2 has been widely used as an additive to increase the osteoinductive properties of bone grafts in multiple applications. However, the commercial production of BMP-2 is expensive and there have been various adverse effects associated with therapeutic applications of BMP-2, particularly for off-label uses. These aspects have limited the therapeutic use of BMP-2. Compared to the use of growth factors to induce osteogenesis of MSCs, small molecule inducers of osteogenesis have less expensive production costs, longer shelf life, convenient dosing regimens and formulations, and unlike biologics (e.g., DNA that persist in the body in some form after administration), small molecules are metabolized and excreted from the body and therefore possess a better safety margin. Accordingly, there is currently a lack of clinically-acceptable agents that can be used to promote osteogenesis and to promote bone formation in implantable substances or grafts.

Until now, no approach to addressing the important problem of promoting human bone formation by combining the cell lineage-enhancing properties of a small molecule with the microenvironment-supporting properties of a matrix has been reported. MSCs have been treated with osteogenic agents, including various small-molecules in advance of transplantation on a matrix carrier, but to date, no significant way to form bone cells has been reported by the concurrent operation of small-molecules and matrices. Unexpectedly, treatment of MSCs with certain small molecules in the presence of matrix in vitro afforded cell preparations highly useful as implants for in vivo bone formation and repair. Thus, addition of a small molecule in the presence of a tricalcium phosphate (TCP) ceramic matrix induced MSCs to a bone lineage useful in therapy, and as specified herein, solves a major problem of bone repair that is the lack of currently available and safe osteoinductive agents for promoting bone growth from stem cells.

In general, induction of osteogenesis can be divided into four phases: recruitment of stem cells to the bone injury, proliferation of stem cells at the site of injury, differentiation of stem cells into osteoblasts and osteocytes, and bone tissue formation by mineralized matrix deposition along with resorption of matrix and remodeling of the bone. To improve the efficiency of implanted cells and bone grafts, this invention describes small molecules that act in conjunction with matrices to dramatically improve all four phases of osteogenesis. What was unexpected was the way in which small molecule-stimulated MSCs dramatically increased their osteogenic properties in the presence of a TCP matrix, and in many cases the effects of small molecule and TCP matrix were synergistic for increasing osteogenic differentiation of stem cells. We identified small molecules that promoted Toll-like receptor (TLR) signaling and/or vitamin D receptor signaling. Wnt signaling is an apparent secondary pathway. Molecules that promoted osteogenesis in the presence (or absence) of matrices were identified using established biomarkers of osteogenesis such as induction of alkaline phosphatase functional activity or mRNA expression levels that are established biomarkers in the field. Compared to either small molecule-stimulated cells or cells incubated in the presence of matrix alone, incubation of specified small molecules with cells in the presence of matrix gave rise to increased osteogenic differentiation that was in excess of the combined effects of small-molecule or matrix taken independently. Also, incubation of specified small molecules with cells in the presence of matrix was discovered to unexpectedly increase cellular migration and localization of cells to the matrix. The induced cell implants prepared through this invention were tested in vivo and showed improved osteoinduction. Therefore, combining small molecules and matrices created a microenvironment that supports cell migration and localization of cells onto the matrix, as well as cell proliferation, cell differentiation, and mineralized protein deposition from cells. The invention can be applied to a wide variety of other human tissue repair processes.

Taking advantage of unique mechanisms of induced osteogenesis by small molecule and matrix, compositions and methods were developed to improve osteogenic properties of both cells and matrix for tissue engineering and cell therapies of bone formation and repair. In the case of small molecule-induced human MSC-matrix combinations (i.e., hMSCs that were cultured with small molecules in the presence of matrix), the MSCs were shown to increase their migratory ability and localization onto a matrix or bone, as well as increase their proliferation and differentiation along the osteogenic lineage. In the case of matrix, small molecules can be used to coat the surface to induce 'chemotactic' effects that caused cells to migrate to the matrix. We invented a highly defined approach using small molecule-induced hMSCs and matrix that promoted osteogenesis and bone tissue formation for use in accelerating bone growth, healing bone injuries, and improving cell engraftment of cell-based implants.

SUMMARY OF THE INVENTION

Figure 1:
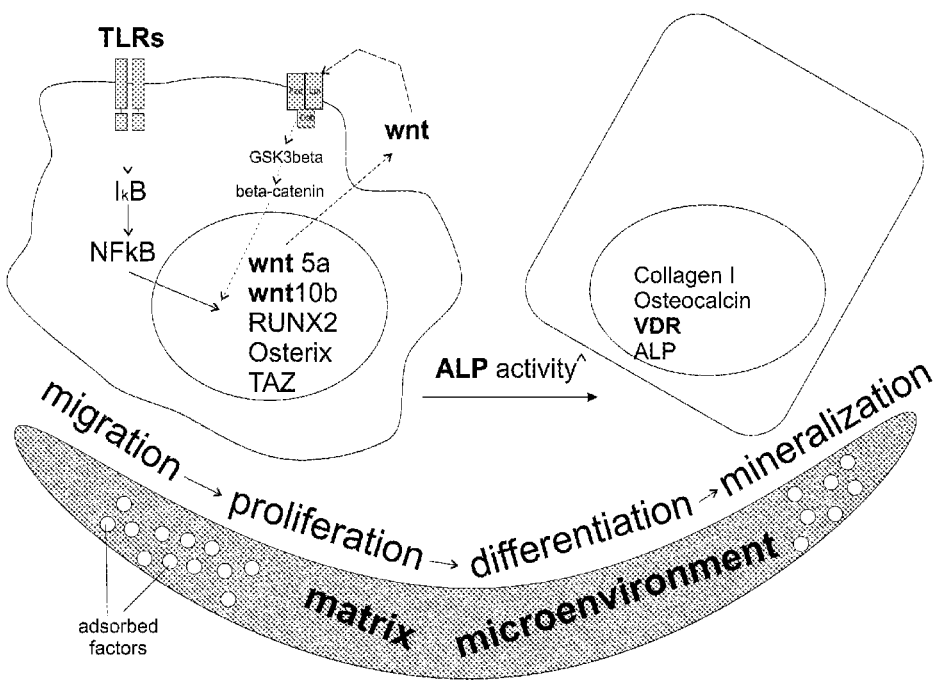
FIG. 1. Scheme depicting the effect of compounds of Formula I to VI on proliferation, differentiation and migration for induction of human mesenchymal stem cells into osteoblasts in the presence of matrix.

The invention provide a composition comprising a compound and isolated cells capable of differentiating into bone cells and a calcium phosphate matrix wherein the compound has the structure of

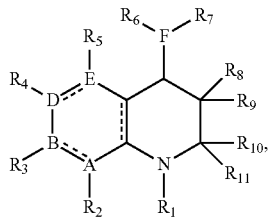

I wherein the dotted lines represent optional double bond; A, B, E is carbon or nitrogen; D is carbon; F is nitrogen; and $R_1$, $R_6$ and $R_7$ are independently methylcarbonyl, trideuteromethylcarbonyl, trifluoromethylcarbonyl, 2,2,2-trifluoroethylcarbonyl, propylcarbonyl, iso-propylcarbonyl, butylcarbonyl, sec-butylcarbonyl, iso-butylcarbonyl, tert-butylcarbonyl, pentylcarbonyl, 2-pentylcarbonyl, 3-pentylcarbonyl, 1,1-dimethylpropylcarbonyl, 1,2-dimethylpropylcarbonyl, 2-methoxyethylcarbonyl, 2-ethoxyethylcarbonyl, cyclopropylcarbonyl, cyclobutylcarbonyl, cyclopentylcarbonyl, cyclohexylcarbonyl, azacycloprop-2-ylcarbonyl, azacyclobut-2-ylcarbonyl, azacyclopent-2-ylcarbonyl, azacyclohex-2-ylcarbonyl, tetrahydrofuran-2-yl, tetrahydrofuran-3-yl, tetrahydrothien-2-yl, tetrahydrothien-3-yl, 2,3-dimethoxyphenylcarbonyl, 2,4-dimethoxyphenylcarbonyl, 2,5-dimethoxyphenylcarbonyl, 2,6-dimethoxyphenylcarbonyl, 3,5-dimethoxyphenylcarbonyl, 2,3,4-trimethoxyphenylcarbonyl, 2,3,5-trimethoxyphenylcarbonyl, 2,3,6-trimethoxyphenylcarbonyl, 2,4,5-trimethoxyphenylcarbonyl, 2,4,6-trimethoxylphenylcarbonyl, 3,4,5-trimethoxyphenylcarbonyl, 2-ethoxyphenylcarbonyl, 3-ethoxyphenylcarbonyl, 4-ethoxyphenylcarbonyl, 2,3-diethoxyphenylcarbonyl, 2,4-diethoxyphenylcarbonyl, 2,5-diethoxyphenylcarbonyl, 2,6-diethoxyphenylcarbonyl, 3,4-diethoxyphenylcarbonyl, 3,5-diethoxyphenylcarbonyl, 2,3,4-triethoxyphenylcarbonyl, 2,3,5-triethoxyphenylcarbonyl, 2,3,6-triethoxyphenylcarbonyl, 2,4,5-triethoxyphenylcarbonyl, 2,4,6-triethoxylphenylcarbonyl, 3,4,5-triethoxyphenylcarbonyl, 2,3-dimethylphenylcarbonyl, 2,4-dimethylphenylcarbonyl, 2,5-dimethylphenylcarbonyl, 2,6-dimethylphenylcarbonyl, 3,4-dimethylphenylcarbonyl, 3,5-dimethylphenylcarbonyl, 2-ethylphenylcarbonyl, 3-ethylphenylcarbonyl, 2,3-diethylphenylcarbonyl, 2,4-diethylphenylcarbonyl, 2,5-diethylphenylcarbonyl, 2,6-diethylphenylcarbonyl, 3,4-diethylphenylcarbonyl, 3,5-diethylphenylcarbonyl, 2,3-difluorophenylcarbonyl, 2,4-difluorophenylcarbonyl, 2,5-difluorophenylcarbonyl, 2,6-difluorophenylcarbonyl, 3,5-difluorophenylcarbonyl, or perfluorophenylcarbonyl; $R_2$, $R_3$, $R_4$, $R_5$, $R_8$, $R_9$, $R_{10}$, and $R_{11}$ are independently hydro, methyl, trideuteromethyl, ethyl, 2,2,2-trifluoroethyl, propyl, 2-propyl, butyl, sec-butyl, iso-butyl, tert-butyl, pentyl, 2-pentyl, 3-pentyl, 1,1-dimethylpropyl, 1,2-dimethylpropyl, cyclopropyl, cyclobutyl, cyclopentyl, cyclohexyl, methoxy, ethoxy, propyloxy, 2-propyloxy, butoxy, sec-butoxy, iso-butoxy, tert-butoxy, pentoxy, 2-pentoxy, 3-pentoxy, 1,1-dimethylpropoxy, 1,2-dimethylpropoxy, fluoro, chloro, amino, dimethylamino, diethylamino, dipropylamino, diisopropylamino, dibutylamino, N-azacycloprop-1-yl, N-azacyclobut-1-yl, N-pyrrolidino, N-piperidino, N-piperazinyl, N-methylpiperazinyl, N-ethylpiperazinyl, or N-propylpiperazinyl.

The invention also provide a composition comprising a compound and isolated cells capable of differentiating into bone cells and calcium phosphate matrix wherein the compound has the structure of

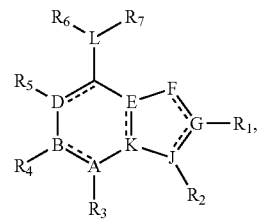

III wherein the dotten lines represent optional double bonds wherein A, E, F, G, J, K and L are independently carbon or nitrogen; B and D are carbon; and $R_1$, $R_3$, $R_4$ and $R_5$ are independently hydro, methyl, trideuteromethyl, trifluoromethyl, ethyl, propyl, iso-propyl, cyclopropyl, cyclobutyl, cyclopentyl, cyclohexyl, amino, N,N-dimethylamino, N,N-diethylamino, N-phenylamino, or unsubstituted; $R_2$ substituent is independently and optionally phenyl, perdeuterophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxylphenyl, 3,4,5-trimethoxyphenyl, 2-ethoxyphenylcarbonyl, 3-ethoxyphenyl, 4-ethoxyphenyl, 2,3-diethoxyphenyl, 2,4-diethoxyphenyl, 2,5-diethoxyphenyl, 2,6-diethoxyphenyl, 3,4-diethoxyphenyl, 3,5-diethoxyphenyl, 2,3,4-triethoxyphenyl, 2,3,5-triethoxyphenyl, 2,3,6-triethoxyphenyl, 2,4,5-triethoxyphenyl, 2,4,6-triethoxylphenyl, 3,4,5-triethoxyphenyl, 2-methylphenyl, 3-methylphenyl, 4-methylphenylcarbonyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, perfluorophenyl, 2-cyanophenyl, 3-cyanophenyl, 4-cyanophenyl, 2-pyridyl, 3-pyridyl, 4-pyridyl, 2-pyrimidinyl, 2-oxazolyl, 2-thiazolyl, 2-oxazolinyl, 2-benzoxazolyl, 1,2,4-oxadiazol-5-yl, 1,2,4-oxadiazol-3-yl, 2-pyrazinyl, cyclopropyl, cyclobutyl, cyclopentyl, cyclohexyl, azacyclopropan-1-yl, azacyclopropan-2-yl, azacyclobutan-1-yl, azacyclobutan-2-yl, azacyclopentan-1-yl, azacyclopentan-2-yl, azacyclohexan-1-yl, azacyclohexan-2-yl, tetrahydrfuran-2-yl; the $R_6$ and $R_7$ substituents are independently and optionally hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, or 2-(N-azacyclobutanyl)ethyl, or $R_6$ and $R_7$ taken together comprise an endocyclic 6-membered N-methylpyrazine, N-ethylpyrazine, or N-propylpyrazine ring.

The invention further provide a composition comprising a compound and isolated cells capable of differentiating into bone cells wherein the compound has the structure of

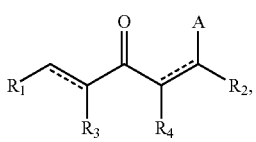

V wherein the dotted lines represent optional double bond; A is oxygen, nitrogen, culfur, or hydrogen; $R_1$ and $R_2$ are independently hydro, alkyl, heteroalkyl, cycloalkyl, cycloheteroalkyl, alkenyl, arylalkenyl, (heteroaryl)alkenyl, aryl, heteroaryl, amino, N-alkylamino, N-(heteroalkyl)amino, N,N-dialkylamino, N-arylamino, N,N-diarylamino, N-amido, S-alkylthio, S-(heteroalkyl)thio, S-arylthio; $R_3$ and $R_4$ are independently hydro, alkyl, heteroalkyl, cycloalkyl, cycloheteroalkyl, alkenyl, arylalkenyl, (heteroaryl)alkenyl, aryl, heteroaryl, halo, hydroxyl, cyano, alkoxy, aryloxy, amino, N-alkylamino, N-(heteroalkyl)amino, N,N-dialkylamino, N-arylamino, N,N-diarylamino, N-amido, S-alkylthio, S-(heteroalkyl)thio, S-arylthio, alkylcarbonyl, cycloalkylcarbonyl, (cycloheteroalkyl)carbonyl, arylcarbonyl, heteroarylcarbonyl, alkoxycarbonyl, aminocarbonyl, alkylthionyl, arylthionyl, alkylsulfonyl, heteroalkylsulfonyl, cycloalkylsulfonyl, (cycloheteroalkyl)sulfonyl, arylsulfonyl, aminosulfonyl, alkylphosphonyl, arylphosphonyl, aminophosphonyl, phosphonate, or sulfonate.

DETAILED DESCRIPTION OF THE DISCLOSURE

Definitions

The following terms, definitions and abbreviations apply. Abbreviations used herein have their conventional meaning within the chemical and biological arts.

"Osteogenesis" as used herein, refers to the formation of bone, bone tissue, and bone cells, including the formation of progenitor cells or any cells that have matured along the bone lineage. While in vivo osteogenesis is a complex process involving bone resorption and re-modeling, for the purposes of this disclosure the term "osteogenesis" is defined more strictly in terms of formation of bone tissues and does not necessarily invoke the resorption or degradation of bone that occurs by osteoclasts in vivo. Accordingly, the term osteogenesis can refer to in vitro and in vivo examples, provided that cells advance along the osteogenic lineage. Osteogenesis is considered a multi-step process that includes, but is not limited to: i) the localization of osteoprogenitor cells or stem cells or cells capable of differentiating into bone to a desired site, ii) the proliferation or growth of bone progenitor cells, or proliferation or growth of bone cells and bone tissue (hard tissue or mineralized matrix), iii) the cell differentiation or cell transdifferentiation of progenitor or precursor cells into cells of the bone lineage such as osteoprogenitor cells, osteoblasts, and osteocytes, iv) the deposition of mineralized matrix from bone cells such as osteoblasts and osteocytes that gives rise to the hard tissue of bone. Progenitor or precursor cells can be mesenchymal stem cells (MSCs) or bone marrow-derived stromal cells (BMSCs) that have pre-committed to a mesodermal lineage, or pluripotent stem cells, induced pluripotent stem cells, and embryonic stem cells that have not pre-committed to an osteo-lineage, or cells such as myoblasts that have pre-committed to a lineage other than the osteo-lineage but can convert into an osteo-lineage with appropriate stimulation.

"Osteogenic" as used herein refers to properties and characteristics that are associated with or support the formation of bone, bone tissue, or bone cells, including bone progenitor cells or any cells that have matured along the bone lineage. For example, a substance that is osteogenic will more capably form bone, deposited bone matrix, and support the processes of cell recruitment and/or angiogenesis. By way of a second example, an osteogenic stem cell may refer to a cell that is highly capable of differentiating into cells of the bone lineage, in vitro or in vivo, that in turn produce the mineralized matrix of bone tissue. By way of a third example, an osteogenic implant refers to a substance that once placed internally in an animal will be capable of supporting bone growth and deposition of mineralized matrix of the bone tissue.

A "stem cell" as used herein, refers to any progenitor cells or precursor cells that have the ability to differentiate into another cell type. Stem cells are classified in part by potency and may be totipotent and capable of generating all cell types of an organism, pluripotent and capable of generating cells of any of the three germ layers, or multipotent and capable of generating multiple but restricted cell lineages, oligopotent and capable of differentiating into only a few cell types, or unipotent and capable of differentiating into only one cell type. Stem cells of varying degrees of potency can be found in many tissue types, but may also be induced from non-pluripotent or somatic cells by forced gene expression in the cells, or by nuclear reprogramming, or by chemical methods, that may also be considered a transdifferentiation for the terms of this disclosure. Stem cells for use in the methods of the present invention include, by way of example, mesenchymal stem cells derived from various tissues, bone marrow-derived stromal cells, osteoprogenitor cells, pre-osteoblasts, pre-adipocytes, osteochondro progenitor cells, pre-chondrocytes, pre-myoblasts, pericytes, hematopoietic stem cells, and the transitory cells of these cell lineages. By way of further example, somatic cells can be considered to be subject to the invention by induction of pluripotency through forced gene expression, somatic cell nuclear transfer (i.e. nuclear reprogramming), or chemical or biochemical stimuli used to induce pluripotency, and so include fibroblasts, adipocytes, macrophages, keratinocytes, hematopoietic cells, erythrocytes, leukocytes, and thrombocytes.

"Lineage" as used herein refers to a shared ancestral path. In cell development, the lineage refers to the path between a specified cell type and either i) cells at a different stage of development from which the specified cells can be derived, or ii) cells (real or hypothetical) to which the specified cells are capable of becoming.

"Differentiate" or "differentiation" as used herein, refers to the process whereby a precursor or progenitor cell grows into specific cell types. Differentiated cells can be identified by their pattern of gene expression, or cell surface protein expression, or characteristic functional properties of the cells.

"Transdifferentiation" refers to the process whereby cells grow into another lineage from a pre-committed lineage. Transdifferentiated cells can be identified by their pattern of gene expression, their surface protein expression, or characteristic functional properties of the cells.

"Culturing" as used herein, refers to maintaining cells under conditions that cells can proliferate, differentiate and avoid senescence. Cells can be cultured in growth media containing appropriate growth factors and chemicals to maintain their normal growth.

"Migration" or "migrate" as used herein refers to a process whereby cells move from one specific location to another location. In the experimental procedure, migration refers to a cell that moves from one surface to another surface through designed openings that restrict random cell movement. For in vivo contexts, migration refers the movement of cells from one location of the body to another location of the body.

"Implant" refers to an object or substance that is inserted into another body. As used herein, the term refers to a substance that is placed internally in an animal, often via the use of surgical or injectable techniques. The term "implantation" refers generally to the process of placing or inserting the implant into the body.

"Cell Implant" refers to an entity, substance, or composition of matter that contains cells and is inserted into another body.

"Transplantation" as used herein refers to a process of transferring a substance from one environment to another. The term is generally used in the context of transferring biological substances including cells, biomaterials, or synthetic materials from an ex vivo environment into an animal or human. For the purposes of this disclosure, the terms "transplantation" and "implantation" have been used interchangeably (i.e., implants may be either implanted or transplanted into an animal).

"Matrix" refers generally to a substance or material that provides a two-dimensional or three-dimensional environment distinct from that of the surroundings. The term as used herein generally refers to naturally occurring or synthetic materials that provide one or more environments such as an outer or internal surface, an internal volume of a cavity, or the matter that comprises the matrix itself. For example, matrices of the disclosure include solid, semisolid and liquid states of matter. By way of further example, matrices of the disclosure include solid matter that extends in size from nanometers to meters and may further take the form of porous or non-porous, permeable or non-permeable, soluble or colloidal substances, while semisolid and liquid states of matter may be porous or non-porous, permeable or non-permeable, colloidal or soluble forms.

"Ceramic" refers generally to a substance that has been hardened by the process of heating. As used herein, the term generally refers to mineral compositions that are hardened by sintering in high temperature ovens. The substances can be prepared and processed in such a way as to provide ceramics of various shapes, sizes, particle sizes, surface topography, microporosity, physical properties such as brittleness and solubility, and chemical properties such as degradation, chemical stability, ion release rates, and resorption.

"Derived" as used herein refers to having emerged or been acquired from a source.

"Induced" as used herein refers to a change in one entity that was caused by a second entity. For examples, cells can be induced by a compound such that the presence of the compound causes the cells to adopt a cell lineage different from their current one.

"Promote" as used herein refers to furthering the progress, or supporting the presence of, a specified characteristic, property, process or behavior.

"Small Molecule" as used herein generally refers to molecules of relatively low molecular weight that are not polymers or biopolymers or macromolecules.

"Bioadhesive" as used herein refers to biologically compatible materials of natural or non-natural origin with adhesive properties that bind together specified entities. For example, congealed blood is biologically compatible. Congealed blood has a gel-like nature that is capable of binding cells, macroscopic or microscopic particles, tricalcium phosphate granules, and small molecules to hold the composite material in a cohesive, often macroscopic, form. A simplified form of congealed blood can be constituted ex vivo by the reaction that occurs between fibrinogen and thrombin that forms a fibrin gel and this gel is known to safely biodegrade once implanted in vivo.

"Suspension" as used herein refers generally to a non-homogeneous mixture. Most commonly, a suspension refers to a biphasic mixture wherein one or more of the components of the mixture is not fully soluble, or is insoluble, in a second component that is often a liquid. For example, a suspension includes particulate matter in solution whether colloidal or as insoluble particles in the presence of a liquid.

The term "alkyl," by itself or as part of another substituent, means, unless otherwise stated, a straight (i.e., unbranched) or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkyl, as exemplified, but not limited, by —$CH_2CH_2CH_2CH_2$—, —$CH_2CH$=$CHCH_2$—, —$CH_2CCH_2$—, —$CH_2CH_2CH$ ($CH_2CH_2CH_3$)$CH_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atom and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—. As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent that can be a single ring or multiple rings, which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, and arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g., "3 to 7 membered"), the term "member" referrers to a carbon or heteroatom.

The term "oxo" as used herein means an oxygen that is double bonded to a carbon atom.

The terms "heterocycle" and "heterocyclic" refer to a monovalent unsaturated group having a single ring or multiple condensed rings, from 1 to 8 carbon atoms and from 1 to 4 heteroatoms, for example, nitrogen, sulfur or oxygen within the ring.

The term "methylthio" refers to a moiety —S—CH$_3$.

The term "sulfonamide" refers to compound A shown below, as well as to the

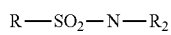

$$R-SO_2-N-R_2 \quad A$$

moiety derived from compound A:

The terms "furyl," "tetrahydrofuryl," and "pyridyl" refer to radicals formed by removing one hydrogen from the molecules of furan, tetrahydrofuran, and pyridine, respectively.

The terms "alkylamine" and "cycloalkylamine" refer to alkanes or cycloalkanes, respectively, having one hydrogen substituted by a primary, secondary or tertiary amino group, as well as to the moieties and radicals derived from such amines.

The term "alkyl amide" refers to alkanes, having one hydrogen substituted by a primary, secondary or tertiary amino group.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO2R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O) CF$_3$, —C(O) CH$_2$OCH$_3$, and the like).

The term "alkoxy" refers to the moiety —O-alkyl, wherein alkyl is as defined above. Examples of alkoxy structures that are within the purview of the definition include, but are not limited to, (C$_1$-C$_6$)alkoxy radicals, such as methoxy, ethoxy, propoxy, isopropoxy, butoxy, iso-butoxy, sec-butoxy, tert-butoxy, pentoxy, 3-pentoxy, or hexyloxy.

The terms "carboxylate" and "alkanoate", and the suffix "oate", as substituents refers to the moiety —O—(O)C—, wherein the bond between substituent and compound is made through the oxygen atom. Examples of carboxylate structures include the acetate (CH$_3$C(O)O—) substituent or the glycine carboxylate (H$_2$NCH$_2$C(O)O—) substituent.

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO2R', —C(O)NR'R", —OC(O)NR'R", —NR"C(O)R', —NR'—C(O)NR"R'", —NR"C(O)OR', —NR—C(NR'R"R'")=NR'", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R", R'" and R"" are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')q-U-, wherein T and U are independently —NR—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)r-B-, wherein A and B are independently —CRR'—, —NR—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S(O)—, —S(O)$_2$—, or —S(O)$_2$NR'—. The substituents R, R', R" and R'" are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties: (A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from: (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from: (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the disclosure may exist as salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When the disclosed compounds contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the disclosure contain both basic and acidic functionalities that allow the compounds to be converted into either base or acid addition salts.

Certain compounds of the disclosure possess asymmetric carbon atoms (optical or chiral centers) or double bonds; the enantiomers, racemates, diastereomers, tautomers, geometric isomers, stereo isometric forms that may be defined, in terms of absolute stereochemistry, as (R) or (S), as (D)- or (L)- for amino acids, and individual isomers are encompassed within the scope of the disclosure. The compounds of the disclosure do not include those which are known in art to be too unstable to synthesize and/or isolate. The disclosure is meant to include compounds in racemic and optically pure forms. Optically active (R) and (S), or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "relative stereochemistry" as used herein refers to the spatial configuration between two or more stereocenters. Two or more stereocenters may be related to each other by, for example, designating if the stereocenters are oriented in a cis configuration that is on the same side of a designated molecular plane or axis of symmetry by which the stereocenters are related, or trans configuration that are on opposite sides of a designated molecular plane or axis of symmetry by which the stereocenters are related. Accordingly, the relative stereochemistry between centers does not define the R or S absolute stereochemical designations described above.

The term "tautomer," as used herein, refers to one of two or more structural isomers which exist in equilibrium and which are readily converted from one isomeric form to another. It will be apparent to one skilled in the art that certain compounds of the disclosure may exist in tautomeric forms, regardless of the tautomeric form depicted, and all such tautomeric forms of the compounds being within the scope of the disclosure irrespective of the thermodynamically more stable tautomer. For the purposes of this disclosure, bonds that involved in interconversion between tautomers are designated as dashed bonds (e.g., C—C═O for a tautomeric keto functionality). For example, a tautomeric keto functionality can equally be depicted in its enol form.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the disclosure.

The compounds of the disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the disclosure, whether radioactive or not, are encompassed within the scope of the disclosure.

The term "pharmaceutically acceptable salts" is meant to include salts of active compounds which are prepared with relatively nontoxic acids or bases, depending on the particular substituent moieties found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, and such organic bases as isopropylamine, trimethylamine, 2-ethyl-amino-ethanol, histidine, procaine, and the like. When compounds of the disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compounds of the disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

In addition to salt forms, the disclosure provides compounds, which are in a prodrug form. Prodrugs of the compounds described herein are those compounds that readily undergo chemical or metabolism-mediated changes under physiological conditions to provide the compounds of the disclosure. Additionally, prodrugs can be converted to the compounds of the disclosure by chemical or biochemical methods in an ex vivo environment. For example, prodrugs can be slowly converted to the compounds of the disclosure when placed with cells or matrix or bioadhesive for implantation with a suitable enzyme or biological or chemical (or spontaneously with water) mileu.

Certain compounds of the disclosure can exist in unsolvated forms as well as solvated forms, including hydrated forms. In general, the solvated forms are to be considered equivalent to unsolvated forms and are encompassed within the scope of the disclosure. Certain compounds of the disclosure may exist in multiple crystalline or amorphous forms. In general, all physical forms are equivalent for the uses contemplated by and are intended to be within the scope of the disclosure.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

The terms "administration of" and or "administering a" compound should be understood to mean providing a compound or compound-matrix composition or compound-cell-matrix composition of the disclosure or pharmaceutical composition to the subject in need of treatment, and is to be understood as a non-limiting term with respect to the route of administration.

Descriptions of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The disclosure provides a composition comprising a compound and isolated cells capable of differentiating into bone cells and a calcium phosphate matrix wherein the compound has the structure of Formula I

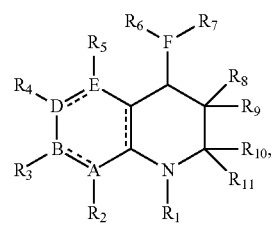

I wherein the dashed lines represent optional double bond, A, B, E is carbon or nitrogen; D is Carbon; F is nitrogen; $R_1$, $R_6$ and $R_7$ substituents are independently methylcarbonyl, trideuteromethylcarbonyl, trifluoromethylcarbonyl, 2,2,2-trifluoroethylcarbonyl, propylcarbonyl, iso-propylcarbonyl, butylcarbonyl, sec-butylcarbonyl, iso-butylcarbonyl, tert-butylcarbonyl, pentylcarbonyl, 2-pentylcarbonyl, 3-pentylcarbonyl, 1,1-dimethylpropylcarbonyl, 1,2-dimethylpropylcarbonyl, 2-methoxyethylcarbonyl, 2-ethoxyethylcarbonyl, cyclopropylcarbonyl, cyclobutylcarbonyl, cyclopentylcarbonyl, cyclohexylcarbonyl, azacycloprop-2-ylcarbonyl, azacyclobut-2-ylcarbonyl, azacyclopent-2-ylcarbonyl, azacyclohex-2-ylcarbonyl, tetrahydrofuran-2-yl, tetrahydrofuran-3-yl, tetrahydrothien-2-yl, tetrahydrothien-3-yl, 2,3-dimethoxyphenylcarbonyl, 2,4-dimethoxyphenylcarbonyl, 2,5-dimethoxyphenylcarbonyl, 2,6-dimethoxyphenylcarbonyl, 3,5-dimethoxyphenylcarbonyl, 2,3,4-trimethoxyphenylcarbonyl, 2,3,5-trimethoxyphenylcarbonyl, 2,3,6-trimethoxyphenylcarbonyl, 2,4,5-trimethoxyphenylcarbonyl, 2,4,6-trimethoxylphenylcarbonyl, 3,4,5-trimethoxyphenylcarbonyl, 2-ethoxyphenylcarbonyl, 3-ethoxyphenylcarbonyl, 4-ethoxyphenylcarbonyl, 2,3-diethoxyphenylcarbonyl, 2,4-diethoxyphenylcarbonyl, 2,5-diethoxyphenylcarbonyl, 2,6-diethoxyphenylcarbonyl, 3,4-diethoxyphenylcarbonyl, 3,5-diethoxyphenylcarbonyl, 2,3,4-triethoxyphenylcarbonyl, 2,3,5-triethoxyphenylcarbonyl, 2,3,6-triethoxyphenylcarbonyl, 2,4,5-triethoxyphenylcarbonyl, 2,4,6-triethoxylphenylcarbonyl, 3,4,5-triethoxyphenylcarbonyl, 2,3-dimethylphenylcarbonyl, 2,4-dimethylphenylcarbonyl, 2,5-dimethylphenylcarbonyl, 2,6-dimethylphenylcarbonyl, 3,4-dimethylphenylcarbonyl, 3,5-dimethylphenylcarbonyl, 2-ethylphenylcarbonyl, 3-ethylphenylcarbonyl, 2,3-diethylphenylcarbonyl, 2,4-diethylphenylcarbonyl, 2,5-diethylphenylcarbonyl, 2,6-diethylphenylcarbonyl, 3,4-diethylphenylcarbonyl, 3,5-diethylphenylcarbonyl, 2,3-difluorophenylcarbonyl, 2,4-difluorophenylcarbonyl, 2,5-difluorophenylcarbonyl, 2,6-difluorophenylcarbonyl, 3,5-difluorophenylcarbonyl, perfluorophenylcarbonyl; the $R_2$, $R_3$, $R_4$, $R_5$, $R_8$, $R_9$, $R_{10}$, and $R_{11}$ substituents are independently and optionally hydro, methyl, trideuteromethyl, ethyl, 2,2,2-trifluoroethyl, propyl, 2-propyl, butyl, sec-butyl, iso-butyl, tert-butyl, pentyl, 2-pentyl, 3-pentyl, 1,1-dimethylpropyl, 1,2-dimethylpropyl, cyclopropyl, cyclobutyl, cyclopentyl, cyclohexyl, methoxy, ethoxy, propyloxy, 2-propyloxy, butoxy, sec-butoxy, iso-butoxy, tert-butoxy, pentoxy, 2-pentoxy, 3-pentoxy, 1,1-dimethylpropoxy, 1,2-dimethylpropoxy, fluoro, amino, dimethylamino, diethylamino, dipropylamino, diisopropylamino, dibutylamino, N-azacycloprop-1-yl, N-azacyclobut-1-yl, N-pyrrolidino, N-piperidino, N-piperazinyl, N-methylpiperazinyl, N-ethylpiperazinyl or N-propylpiperazinyl.

In one embodiment, the disclosure provides the above composition, wherein the compound has the structure of Formula II

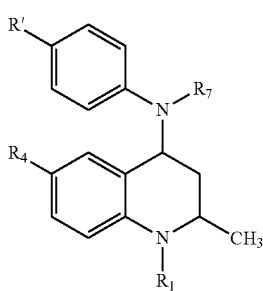

II wherein $R_1$ and $R_7$ substituents are independently methylcarbonyl, trideuteromethylcarbonyl, trifluoromethylcarbonyl, 2,2,2-trifluoroethylcarbonyl, propylcarbonyl, iso-propylcarbonyl, butylcarbonyl, sec-butylcarbonyl, iso-butylcarbonyl, tert-butylcarbonyl, pentylcarbonyl, 2-pentylcarbonyl, 3-pentylcarbonyl, 1,1-dimethylpropylcarbonyl, 1,2-dimethylpropylcarbonyl, 2-methoxyethylcarbonyl, 2-ethoxyethylcarbonyl, cyclopropylcarbonyl, cyclobutylcarbonyl, cyclopentylcarbonyl, cyclohexylcarbonyl, azacycloprop-2-ylcarbonyl, azacyclobut-2-ylcarbonyl, azacyclopent-2-ylcarbonyl, azacyclohex-2-ylcarbonyl, tetrahydrofuran-2-yl, tetrahydrofuran-3-yl, tetrahydrothien-2-yl, tetrahydrothien-3-yl, 2,3-dimethoxyphenylcarbonyl, 2,4-dimethoxyphenylcarbonyl, 2,5-dimethoxyphenylcarbonyl, 2,6-dimethoxyphenylcarbonyl, 3,5-dimethoxyphenylcarbonyl, 2,3,4-trimethoxyphenylcarbonyl, 2,3,5-trimethoxyphenylcarbonyl, 2,3,6-trimethoxyphenylcarbonyl, 2,4,5-trimethoxyphenylcarbonyl, 2,4,6-trimethoxylphenylcarbonyl, 3,4,5-trimethoxyphenylcarbonyl, 2-ethoxyphenylcarbonyl, 3-ethoxyphenylcarbonyl, 4-ethoxyphenylcarbonyl, 2,3-diethoxyphenylcarbonyl, 2,4-diethoxyphenylcarbonyl, 2,5-diethoxyphenylcarbonyl, 2,6-diethoxyphenylcarbonyl, 3,4-diethoxyphenylcarbonyl, 3,5-diethoxyphenylcarbonyl, 2,3,4-triethoxyphenylcarbonyl, 2,3,5-triethoxyphenylcarbonyl, 2,3,6-triethoxyphenylcarbonyl, 2,4,5-triethoxyphenylcarbonyl, 2,4,6-triethoxylphenylcarbonyl, 3,4,5-triethoxyphenylcarbonyl, 2,3-dimethylphenylcarbonyl, 2,4-dimethylphenylcarbonyl, 2,5-dimethylphenylcarbonyl, 2,6-dimethylphenylcarbonyl, 3,4-dimethylphenylcarbonyl, 3,5-dimethylphenylcarbonyl, 2-ethylphenylcarbonyl, 3-ethylphenylcarbonyl, 2,3-diethylphenylcarbonyl, 2,4-diethylphenylcarbonyl, 2,5-diethylphenylcarbonyl, 2,6-diethylphenylcarbonyl, 3,4-diethylphenylcarbonyl, 3,5-diethylphenylcarbonyl, 2,3-difluorophenylcarbonyl, 2,4-difluorophenylcarbonyl, 2,5-difluorophenylcarbonyl, 2,6-difluorophenylcarbonyl, 3,5-difluorophenylcarbonyl, perfluorophenylcarbonyl; $R_4$ and R' substituents are independently and optionally hydro, methyl, trideuteromethyl, ethyl, 2,2,2-trifluoroethyl, propyl, 2-propyl, butyl, sec-butyl, iso-butyl, tert-butyl, pentyl, 2-pentyl, 3-pentyl, 1,1-dimethylpropyl, 1,2-dimethylpropyl, cyclopropyl, cyclobutyl, cyclopentyl, cyclohexyl, methoxy, ethoxy, propyloxy, 2-propyloxy, butoxy, sec-butoxy, iso-butoxy, tert-butoxy, pentoxy, 2-pentoxy, 3-pentoxy, 1,1-dimethylpropoxy, 1,2-dimethylpropoxy, fluoro, chloro, amino, dimethylamino, diethylamino, dipropylamino, diisopropylamino, dibutylamino, N-azacycloprop-1-yl, N-azacyclobut-1-yl, N-pyrrolidino, N-piperidino, N-piperazinyl, N-methylpiperazinyl, N-ethylpiperazinyl or N-propylpiperazinyl.

In one embodiment, the disclosure provides the above composition, wherein the compound has the structure of Formula IIa

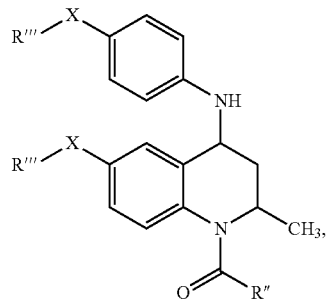

IIa wherein R" is independently cyclopropyl, cyclobutyl, cyclopentyl, cyclohexyl, tetrahydrofuran-2-yl, tetrahydrofuran-3-yl, tetrahydrothien-2-yl, tetrahydrothien-3-yl; X is independently and optionally oxygen or sulfur; and each R''' is independently cyclopropyl, cyclobutyl, cyclopentyl or cyclohexyl.

The disclosure provides a composition comprising a compound and isolated cells capable of differentiating into bone cells and calcium phosphate matrix wherein the compound has the structure of Formula III

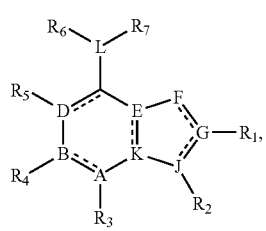

III wherein A, E, F, G, J, K and L are independently carbon or nitrogen; B and D are carbon; $R_1$, $R_3$, $R_4$ and $R_5$ are independently hydro, methyl, trideuteromethyl, trifluoromethyl, ethyl, propyl, iso-propyl, cyclopropyl, cyclobutyl, cyclopentyl, cyclohexyl, amino, N,N-dimethylamino, N,N-diethylamino or N-phenylamino, or unsubstituted; $R_2$ substituent is independently and optionally phenyl, perdeuterophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxylphenyl, 3,4,5-trimethoxyphenyl, 2-ethoxyphenylcarbonyl, 3-ethoxyphenyl, 4-ethoxyphenyl, 2,3-diethoxyphenyl, 2,4-diethoxyphenyl, 2,5-diethoxyphenyl, 2,6-diethoxyphenyl, 3,4-diethoxyphenyl, 3,5-diethoxyphenyl, 2,3,4-triethoxyphenyl, 2,3,5-triethoxyphenyl, 2,3,6-triethoxyphenyl, 2,4,5-triethoxyphenyl, 2,4,6-triethoxylphenyl, 3,4,5-triethoxyphenyl, 2-methylphenyl, 3-methylphenyl, 4-methylphenylcarbonyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, perfluorophenyl, 2-cyanophenyl, 3-cyanophenyl, 4-cyanophenyl, 2-pyridyl, 3-pyridyl, 4-pyridyl, 2-pyrimidinyl, 2-oxazolyl, 2-thiazolyl, 2-oxazolinyl, 2-benzoxazolyl, 1,2,4-oxadiazol-5-yl, 1,2,4-oxadiazol-3-yl, 2-pyrazinyl, cyclopropyl, cyclobutyl, cyclopentyl, cyclohexyl, azacyclopropan-1-yl, azacyclopropan-2-yl, azacyclobutan-1-yl, azacyclobutan-2-yl, azacyclopentan-1-yl, azacyclopentan-2-yl, azacyclohexan-1-yl, azacyclohexan-2-yl, tetrahydrfuran-2-yl; the $R_6$ and $R_7$ substituents are independently and optionally hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl or 2-(N-azacyclobutanyl)ethyl, or $R_6$ and $R_7$ are taken together to comprise an endocyclic 6-membered N-methylpyrazine, N-ethylpyrazine, or N-propylpyrazine ring.

In one embodiment, the disclosure provides the above composition, wherein the compound has the structure of Formula IV

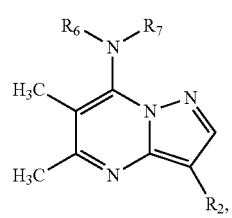

IV wherein, $R_2$ is independently phenyl, perdeuterophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxylphenyl, 3,4,5-trimethoxyphenyl, 2-ethoxyphenylcarbonyl, 3-ethoxyphenyl, 4-ethoxyphenyl, 2,3-diethoxyphenyl, 2,4-diethoxyphenyl, 2,5-diethoxyphenyl, 2,6-diethoxyphenyl, 3,4-diethoxyphenyl, 3,5-diethoxyphenyl, 2,3,4-triethoxyphenyl, 2,3,5-triethoxyphenyl, 2,3,6-triethoxyphenyl, 2,4,5-triethoxyphenyl, 2,4,6-triethoxylphenyl, 3,4,5-triethoxyphenyl, 2-methylphenyl, 3-methylphenyl, 4-methylphenylcarbonyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, perfluorophenyl, 2-cyanophenyl, 3-cyanophenyl, 4-cyanophenyl, 2-pyridyl, 3-pyridyl, 4-pyridyl, 2-pyrimidinyl, 2-oxazolyl, 2-thiazolyl, 2-oxazolinyl, 2-benzoxazolyl, 1,2,4-oxadiazol-5-yl, 1,2,4-oxadiazol-3-yl, 2-pyrazinyl, cyclopropyl, cyclobutyl, cyclopentyl, cyclohexyl, azacyclopropan-1-yl, azacyclopropan-2-yl, azacyclobutan-1-yl, azacyclobutan-2-yl, azacyclopentan-1-yl, azacyclopentan-2-yl, azacyclohexan-1-yl, azacyclohexan-2-yl, tetrahydrfuran-2-yl; the $R_6$ and $R_7$ substituents are independently and optionally hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, or 2-(N-azacyclobutanyl)ethyl; the $R_6$ and $R_7$ substituents are independently and optionally hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl or 2-(N-azacyclobutanyl)ethyl, or $R_6$ and $R_7$ are taken together to comprise an endocyclic 6-membered N-methylpyrazine, N-ethylpyrazine, or N-propylpyrazine ring.

In one embodiment, the disclosure provides the above composition, wherein the compound has the structure of Formula IVa

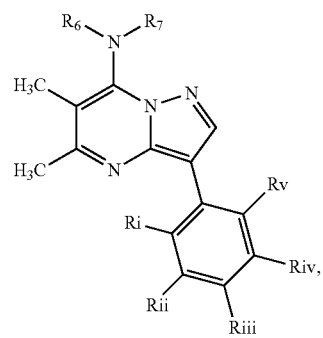

IVa wherein $R_6$ and $R_7$ are independently hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, 2-(N-azacyclobutanyl)ethyl, or $R_6$ and $R_7$ are both substituted to comprise an endocyclic 6-membered N-methylpyrazine, N-ethylpyrazine, or N-propylpyrazine ring; $R_6$ and $R_7$ are not both hydro; $R_i$, $R_{ii}$, $R_{iii}$, $R_{iv}$, and $R_v$ are independently and optionally comprised of deutero, methyl, ethyl, propyl, iso-propyl, butyl, sec-butyl, iso-butyl, tert-butyl, fluoro, chloro, cyano, trifluoromethyl, acetamido, nitro, methoxy, ethoxy, propyoxy, iso-propoxy, butoxy, sec-butoxy, iso-butoxy, tert-butoxy, 1,2,3-triazolyl, tetrazolyl.

In one embodiment, the disclosure provides the above composition, wherein the compound has the structure of Formula IVb

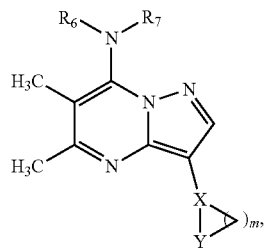

IVb wherein $R_6$ and $R_7$ are independently hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, 2-(N-azacyclobutanyl)ethyl, or $R_6$ and $R_7$ are taken together to comprise an endocyclic 6-membered N-methylpyrazine, N-ethylpyrazine, or N-propylpyrazine ring; $R_6$ and $R_7$ are not both hydro; X and Y are independently carbon, oxygen, or nitrogen; and m is 0-6.

The disclosure provides a composition comprising a compound and isolated cells capable of differentiating into bone cells and calcium phosphate matrix wherein the compound has the structure of Formula V

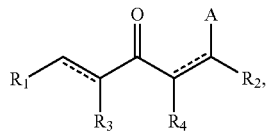

V wherein A is independently oxygen, nitrogen, sulfur, or hydrogen; $R_1$ and $R_2$ are independently hydro, alkyl, heteroalkyl, cycloalkyl, cycloheteroalkyl, alkenyl, arylalkenyl, (heteroaryl)alkenyl, aryl, heteroaryl, amino, N-alkylamino, N-(heteroalkyl)amino, N,N-dialkylamino, N-arylamino, N,N-diarylamino, N-amido, S-alkylthio, S-(heteroalkyl)thio, S-arylthio, or other moiety forming a salt or prodrug; $R_3$ and $R_4$ substituents are independently and optionally hydro, alkyl, heteroalkyl, cycloalkyl, cycloheteroalkyl, alkenyl, arylalkenyl, (heteroaryl)alkenyl, aryl, heteroaryl, halo, hydroxyl, cyano, alkoxy, aryloxy, amino, N-alkylamino, N-(heteroalkyl)amino, N,N-dialkylamino, N-arylamino, N,N-diarylamino, N-amido, S-alkylthio, S-(heteroalkyl)thio, S-arylthio, alkylcarbonyl, cycloalkylcarbonyl, (cycloheteroalkyl)carbonyl, arylcarbonyl, heteroarylcarbonyl, alkoxycarbonyl, aminocarbonyl, alkylthionyl, arylthionyl, alkylsulfonyl, heteroalkylsulfonyl, cycloalkylsulfonyl, (cycloheteroalkyl)sulfonyl, arylsulfonyl, aminosulfonyl, alkylphosphonyl, arylphosphonyl, aminophosphonyl, phosphonate, or sulfonate.

In one embodiment, the disclosure provides the above composition, wherein the compound has the structure of Formula VI

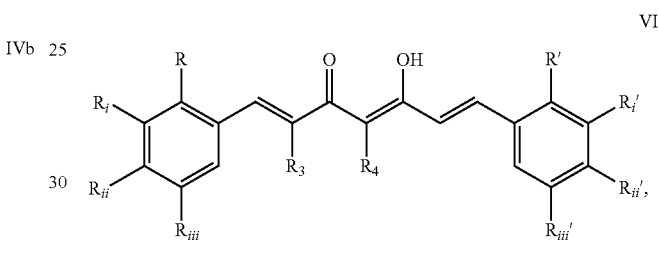

VI wherein R, $R_i$, $R_{ii}$, $R_{iii}$, R', $R_i'$, $R_{ii}'$, and $R_{iii}'$ are independently hydro, methoxy, ethoxy, 2,2,2-trifluoroethoxy, propoxy, iso-proxy, butoxy, sec-butoxy, iso-butoxy, tert-butoxy, pentoxy, 2-pentoxy, 3-pentoxy, 1,1-dimethylpropoxy, 1,2-dimethylpropoxy, methyl, trideuteromethyl, trifluoromethyl, ethyl, 2,2,2-trifluoroethyl, propyl, isopropyl, 1,1,1,3,3,3-hexafluoro-2-propyl, butyl, sec-butyl, iso-butyl, tert-butyl, cyclopropyl, cyclobutyl, cyclopentyl, cyclohexyl, fluoro, cyano, glycine-O-carboxylate, sarcosine-O-carboxylate, alanine-O-carboxylate, valine-O-carboxylate, leucine-O-carboxylate, isoleucine-O-carboxylate, phenylalanine-O-carboxylate, tyrosine-O-carboxylate, tryptophan-O-carboxylate, asparagine-O-carboxylate, glutamine-O-carboxylate, lysine-O-carboxylate, proline-O-carboxylate, 2-amino-2-methyl-propionate, 1-aminocyclopropylcarboxylate, 1-aminocyclobutanecarboxylate, amino, dimethylamino, diethylamino, dipropylamino, diisopropylamino, dibutylamino, N-azacyclopropyl, N-azacyclobutyl, N-pyrrolidino, N-piperidino, N-piperazinyl, N-methylpiperazinyl, N-ethylpiperazinyl, or N-propylpiperazinyl; $R_3$ and $R_4$ are independently hydro, methyl, trideuteromethyl, trifluoromethyl, ethyl, propyl, isopropyl, butyl, sec-butyl, iso-butyl, tert-butyl, cyclopropyl, cyclobutyl, cyclopentyl, cyclohexyl, or $R_3$ and $R_4$ taken together with an alkyl chain define a 5-membered or 6-membered ring.

In one embodiment, the disclosure provides the above composition, wherein the compound has the structure of Formula VIa

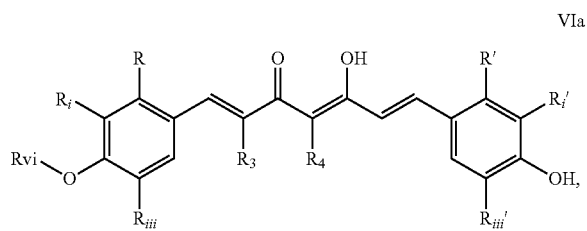

VIa wherein R, R$_{iii}$, R' and R$_{iii}$' are independently hydro, hydroxyl, methoxy, ethoxy, propoxy, iso-propoxy, butoxy, sec-butoxy, iso-butoxy, tert-butoxy, methyl, ethyl, propyl, iso-propyl, butyl, sec-butyl, iso-butyl, tert-butyl, fluoro, chloro, cyano, N,N-dimethylamino, N,N-diethylamino, N,N-dipropylamino, N,N-diisopropylamino; R$_i$ and R$_i$' substituents are independently hydro, methyl, ethyl, propyl, fluoro, chloro, cyano, N,N-dimethylamino, N,N-diethylamino, N,N-dipropylamino, or N,N-diisopropylamino; R$_3$ and R$_4$ are independently hydro, methyl, ethyl, propyl, iso-propyl, butyl, sec-butyl, iso-butyl, or R$_i$ and R$_i$' are taken together with an alkyl chain to define a 5-membered or 6-membered ring; R$_{vi}$ substituent is glycinoyl, sarcosinoyl, alaninoyl, valinoyl, leucinoyl, isoleucinoyl, phenylalaninoyl, tyrosinoyl, tryptophanoyl, asparaginoyl, glutaminoyl, lysinoyl, aspartoyl, glutamoyl, serinoyl, threoninoyl, methioninoyl, prolinoyl, (2-amino-2-methyl)propanoyl, (2-aminocyclopropylmethanoyl, or (1-aminocyclobutane) carbonoyl, 2-amino-3-methylpentanoyl, 2-amino-4-methylpentanoyl.

In one embodiment, the disclosure provides all of the above composition, wherein the isolated cells capable of differentiating into bone cells are isolated human bone marrow-derived mesenchymal stem cells, human mesenchymal stem cells of adipose tissue, human mesenchymal stem cells of blood, human mesenchymal stem cells of bone allograft or autograft tissues, human mesenchymal stem cells of dental pulp, human pericytes, human myoblasts, and human chondrocytes, human osteoprogenitor cells, urine stem cells, or their respective progenitor cells such as stem cell isolated from amniotic fluid or cord blood, embryonic stem cells, and induced pluripotent stem cells.

In one embodiment, the disclosure provides the above compositions, wherein the calcium phosphate matrix is a tricalcium phosphate ceramic or is oseoinductive.

In one embodiment, the disclosure provides compositions of any of the above compositions further comprising a calcium phosphate matrix, wherein the compound is covalently or non-covalently associated with the calcium phosphate matrix or is osteoinductive.

The disclosure provides a composition of cis-1-acetyl-2,6-dimethyl-N-(p-methylphenyl)-1,2,3,4-tetrahydroquinolin-4-amine, isolated cells are human bone marrow-derived mesenchymal stem cells, and a tricalcium phosphate ceramic.

The disclosure provides a composition of 3-phenyl-5,6-dimethyl-7-[N-(2-N,N-dimethylaminoethyl)amino]-pyrazolo[1,5-a]pyrimidine, isolated cells are human bone marrow-derived mesenchymal stem cells, and a tricalcium phosphate ceramic.

The disclosure provides a composition of (2S,2'S)—O,O'-(3-hydroxy-5-oxohepta-1,3,6-triene-1,7-diyl)bis(4,1-phenylene) bis(2-amino-3-methylbutanoate) HCl salt, isolated cells are human bone marrow-derived mesenchymal stem cells, and a tricalcium phosphate ceramic.

The disclosure provides a composition of 4-((1E,3Z)-3-(3-((E)-4-((L-valyl)oxy)benzylidene)-2-oxocyclohexylidene)-3-hydroxyprop-1-en-1-yl)phenyl L-valinate HCl salt, isolated cells are human bone marrow-derived mesenchymal stem cells, and a tricalcium phosphate ceramic.

In one embodiment, the disclosure provides the above compositions wherein the compound is covalently or non-covalently associated with the calcium phosphate matrix.

In one embodiment, the disclosure provides the above compositions further comprising bone morphogenetic proteins, fibroblast growth factors, platelet-derived growth factors, Wnt proteins, transforming growth factors, stromal derived factor-1, parathyroid growth hormone, vitamin D, 1,25-dihydroxy vitamin D, deoxycholic acid, teriparatide, ascorbic acid, ascorbic acid 2-phosphate, beta-glycerol phosphate, dexamethasone, or their respective salts, prodrugs, or a combination thereof.

The disclosure provides a method of inducing bone formation comprising:
(a) treating isolated cells capable of differentiating into bone cells with a compound having the structure of Formula II, the structure of Formula IV or the structure of Formula VI and
(b) administering the treated cells from step (a) to a subject.

The disclosure provides the above method further comprising the step of seeding the cells from step (a) onto a calcium phosphate matrix prior to administering the cells to a subject.

The disclosure provides a method of inducing bone formation comprising:
(a) treating isolated cells capable of differentiating into bone cells with a compound having the structure of Formula II, the structure of Formula IV or the structure of Formula VI, and
(b) administering the treated cells from step (a) to a subject, or
(b') administering the treated cells from step (a) and a calcium phosphate matrix to a subject, or
(a') administering isolated cells capable of differentiating into bone cells cells, a calcium phosphate matrix, and a compound having the structure of Formula II, the structure of Formula IV or the structure of Formula VI to a subject.

The disclosure provides a bone graft material prepared by combining isolated cells capable of differentiating into bone cells cells, a calcium phosphate matrix, and a compound having the structure of Formula II, the structure of Formula IV or the structure of Formula VI into a surgical cage.

The disclosure provides a method for increasing adherence of cells to calcium phosphate materials by treatment of cells in the presence of a calcium phosphate material with a compound of Formula II, IV, or VI.

The disclosure provides a method of inducing bone formation comprising:
(a) combining the compositions of the disclosure with a bioadhesive, and
(b) administering the composition of step (a) to a subject, or
(c) adding the composition of step (a) to a surgical cage and implantation in a subject.

The disclosure provides a method of cryopreserving the compositions of disclosure by:
(a) combining the compositions of the disclosure with a cryopreservative in a sealable tube, and
(b) freezing the tube in liquid nitrogen, and
(c) maintaining the tube in liquid nitrogen.

The disclosure provides a method of identifying new compounds that stimulate bone formation in the presence of matrices, comprising:

(a) adding test compound to cell incubations in the presence of calcium phosphate materials, and
(b) determining alkaline phosphatase functional activity in the cells of step (a), or
(c) determining Toll-like Receptor expression in the cells of step (a), or
(d) determining Runx2 and BMP2 mRNA tandem expression in the cells of step (a).

In one aspect the disclosure provides compositions of a compound and a matrix; suitable for bone growth and repair.

In another aspect the disclosure provides compositions of a compound, matrix, and isolated cells capable of differentiating to bone cells.

In another aspect the disclosure provides compositions of a compound and isolated cells capable of differentiating to bone cells.

In another aspect the disclosure provides compositions of multiple compounds and/or multiple matrices that increase osteogenesis.

In another aspect the disclosure provides compositions of multiple compounds and/or multiple matrices and isolated cell capable of differentiating to bone cells.

In another aspect the disclosure provides compositions of a compound, matrix, and a bioadhesive material.

In another aspect the disclosure provides compositions of a compound, matrix, isolated cells capable of differentiating to bone cells, and a bioadhesive material.

In another aspect the disclosure provides compositions of a compound, isolated cells capable of differentiating to bone cells, and a bioadhesive material.

In another aspect the disclosure provides any one of the above compositions wherein the compound is of Formula I to VI as defined herein.

In another aspect the disclosure provides any one of the above compositions wherein the compound is a small molecule capable of modulating the Toll like receptor (TLR) signaling pathway.

In another aspect the disclosure provides any one of the above compositions wherein the compound is a small molecule capable of modulating the Wnt signaling pathway.

In another aspect the disclosure provides any one of the above compositions wherein the compound is a small molecule capable of modulating the function and expression of the vitamin D receptor.

In another aspect the disclosure provides any one of the above compositions wherein the compound is a small molecule capable of promoting phenotypic markers of osteogenesis such as alkaline phosphatase functional activity.

In another aspect the disclosure provides any one of the above compositions wherein the matrix is an osteoinductive material.

In another aspect the disclosure provides any one of the above compositions wherein the matrix is an osteoconductive material.

In another aspect the disclosure provides any one of the above compositions wherein the matrix is a tricalcium phosphate ceramic.

In another aspect the disclosure provides any one of the above compositions wherein the matrix is synthetic or natural polymers.

In another aspect the disclosure provides any one of the above compositions wherein the isolated cells are animal stem cells.

In another aspect the disclosure provides any one of the above compositions wherein the isolated cells are of human adult stem cells.

In another aspect the disclosure provides any one of the the above compositions wherein the isolated cells are human mesenchymal stem cells.

In another aspect the disclosure provides any one of the above compositions wherein serum is present.

In another aspect the disclosure provides any one of the above compositions wherein biological growth factors are added.

In another aspect the disclosure provides a composition of cell culture media supplemented with a compound of Formula I to VI defined herein that is a new osteogenic media.

In another aspect the disclosure provides a compound of Formula II.

In another aspect the disclosure provides a compound of Formula IV.

In another aspect the disclosure provides a compound of Formula VI.

In one embodiment, the disclosure provides a composition comprising a compound and isolated cells capable of differentiating into bone cells and a calcium phosphate matrix wherein the compound has the structure of Formula I wherein A, B, E is Carbon or Nitrogen; D is Carbon; F is Nitrogen; $R_1$, $R_6$ and $R_7$ substituents are independently and optionally methylcarbonyl, trideuteromethylcarbonyl, trifluoromethylcarbonyl, 2,2,2-trifluoroethylcarbonyl, propylcarbonyl, iso-propylcarbonyl, butylcarbonyl, sec-butylcarbonyl, iso-butylcarbonyl, tert-butylcarbonyl, pentylcarbonyl, 2-pentylcarbonyl, 3-pentylcarbonyl, 1,1-dimethylpropylcarbonyl, 1,2-dimethylpropylcarbonyl, 2-methoxyethylcarbonyl, 2-ethoxylethylcarbonyl, cyclopropylcarbonyl, cyclobutylcarbonyl, cyclopentylcarbonyl, cyclohexylcarbonyl, azacycloprop-2-ylcarbonyl, azacyclobut-2-ylcarbonyl, azacyclopent-2-ylcarbonyl, azacyclohex-2-ylcarbonyl, tetrahydrofuran-2-yl, tetrahydrofuran-3-yl, tetrahydrothien-2-yl, tetrahydrothien-3-yl, 2,3-dimethoxyphenylcarbonyl, 2,4-dimethoxyphenylcarbonyl, 2,5-dimethoxyphenylcarbonyl, 2,6-dimethoxyphenylcarbonyl, 3,5-dimethoxyphenylcarbonyl, 2,3,4-trimethoxyphenylcarbonyl, 2,3,5-trimethoxyphenylcarbonyl, 2,3,6-trimethoxyphenylcarbonyl, 2,4,5-trimethoxyphenylcarbonyl, 2,4,6-trimethoxylphenylcarbonyl, 3,4,5-trimethoxyphenylcarbonyl, 2-ethoxyphenylcarbonyl, 3-ethoxyphenylcarbonyl, 4-ethoxyphenylcarbonyl, 2,3-diethoxyphenylcarbonyl, 2,4-diethoxyphenylcarbonyl, 2,5-diethoxyphenylcarbonyl, 2,6-diethoxyphenylcarbonyl, 3,4-diethoxyphenylcarbonyl, 3,5-diethoxyphenylcarbonyl, 2,3,4-triethoxyphenylcarbonyl, 2,3,5-triethoxyphenylcarbonyl, 2,3,6-triethoxyphenylcarbonyl, 2,4,5-triethoxyphenylcarbonyl, 2,4,6-triethoxylphenylcarbonyl, 3,4,5-triethoxyphenylcarbonyl, 2,3-dimethylphenylcarbonyl, 2,4-dimethylphenylcarbonyl, 2,5-dimethylphenylcarbonyl, 2,6-dimethylphenylcarbonyl, 3,4-dimethylphenylcarbonyl, 3,5- dimethylphenylcarbonyl, 2-ethylphenylcarbonyl, 3-ethylphenylcarbonyl, 2,3-diethylphenylcarbonyl, 2,4-diethylphenylcarbonyl, 2,5-diethylphenylcarbonyl, 2,6-diethylphenylcarbonyl, 3,4-diethylphenylcarbonyl, 3,5-diethylphenylcarbonyl, 2,3-difluorophenylcarbonyl, 2,4-difluorophenylcarbonyl, 2,5-difluorophenylcarbonyl, 2,6-difluorophenylcarbonyl, 3,5-difluorophenylcarbonyl, perfluorophenylcarbonyl; the $R_2$, $R_3$, $R_4$, $R_5$, $R_8$, $R_9$, $R_{10}$, and $R_{11}$ substituents are independently and optionally hydro, methyl, trideuteromethyl, ethyl, 2,2,2-trifluoroethyl, propyl, 2-propyl, butyl, sec-butyl, iso-butyl, tert-butyl, pentyl, 2-pentyl, 3-pentyl, 1,1-dimethylpropyl, 1,2-dimethylpropyl, cyclopropyl, cyclobutyl, cyclopentyl, cyclohexyl, methoxy, ethoxy, propyloxy, 2-propyloxy, butoxy, sec-butoxy, iso-butoxy, tert-butoxy, pentoxy, 2-pentoxy, 3-pentoxy, 1,1-dimethylpropoxy, 1,2-dimethylpropoxy, fluoro, amino, dimethylamino, diethylamino, dipropylamino, diisopropylamino, dibutylamino, N-azacycloprop-1-yl, N-azacyclobut-1-yl, N-pyrrolidino, N-piperidino, N-piperazinyl, N-methylpiperazinyl, N-ethylpiperazinyl, N-propylpiperazinyl.

In one embodiment, the disclosure provides the above composition, wherein the compound has the structure of Formula II

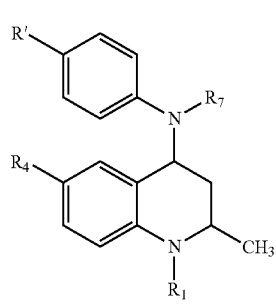

wherein $R_1$ and $R_7$ substituents are independently and optionally methylcarbonyl, trideuteromethylcarbonyl, trifluoromethylcarbonyl, 2,2,2-trifluoroethylcarbonyl, propylcarbonyl, iso-propylcarbonyl, butylcarbonyl, sec-butylcarbonyl, iso-butylcarbonyl, tert-butylcarbonyl, pentylcarbonyl, 2-pentylcarbonyl, 3-pentylcarbonyl, 1,1-dimethylpropylcarbonyl, 1,2-dimethylpropylcarbonyl, 2-methoxyethylcarbonyl, 2-ethoxyethylcarbonyl, cyclopropylcarbonyl, cyclobutylcarbonyl, cyclopentylcarbonyl, cyclohexylcarbonyl, azacycloprop-2-ylcarbonyl, azacyclobut-2-ylcarbonyl, azacyclopent-2-ylcarbonyl, azacyclohex-2-ylcarbonyl, tetrahydrofuran-2-yl, tetrahydrofuran-3-yl, tetrahydrothien-2-yl, tetrahydrothien-3-yl, 2,3-dimethoxyphenylcarbonyl, 2,4-dimethoxyphenylcarbonyl, 2,5-dimethoxyphenylcarbonyl, 2,6-dimethoxyphenylcarbonyl, 3,5-dimethoxyphenylcarbonyl, 2,3,4-trimethoxyphenylcarbonyl, 2,3,5-trimethoxyphenylcarbonyl, 2,3,6-trimethoxyphenylcarbonyl, 2,4,5-trimethoxyphenylcarbonyl, 2,4,6-trimethoxylphenylcarbonyl, 3,4,5-trimethoxyphenylcarbonyl, 2-ethoxyphenylcarbonyl, 3-ethoxyphenylcarbonyl, 4-ethoxyphenylcarbonyl, 2,3-diethoxyphenylcarbonyl, 2,4-diethoxyphenylcarbonyl, 2,5-diethoxyphenylcarbonyl, 2,6-diethoxyphenylcarbonyl, 3,4-diethoxyphenylcarbonyl, 3,5-diethoxyphenylcarbonyl, 2,3,4-triethoxyphenylcarbonyl, 2,3,5-triethoxyphenylcarbonyl, 2,3,6-triethoxyphenylcarbonyl, 2,4,5-triethoxyphenylcarbonyl, 2,4,6-triethoxylphenylcarbonyl, 3,4,5-triethoxyphenylcarbonyl, 2,3-dimethylphenylcarbonyl, 2,4-dimethylphenylcarbonyl, 2,5-dimethylphenylcarbonyl, 2,6-dimethylphenylcarbonyl, 3,4-dimethylphenylcarbonyl, 3,5-dimethylphenylcarbonyl, 2-ethylphenylcarbonyl, 3-ethylphenylcarbonyl, 2,3-diethylphenylcarbonyl, 2,4-diethylphenylcarbonyl, 2,5-diethylphenylcarbonyl, 2,6-diethylphenylcarbonyl, 3,4-diethylphenylcarbonyl, 3,5-diethylphenylcarbonyl, 2,3-difluorophenylcarbonyl, 2,4-difluorophenylcarbonyl, 2,5-difluorophenylcarbonyl, 2,6-difluorophenylcarbonyl, 3,5-difluorophenylcarbonyl, perfluorophenylcarbonyl; $R_4$ and R' substituents are independently and optionally hydro, methyl, trideuteromethyl, ethyl, 2,2,2-trifluoroethyl, propyl, 2-propyl, butyl, sec-butyl, iso-butyl, tert-butyl, pentyl, 2-pentyl, 3-pentyl, 1,1-dimethylpropyl, 1,2-dimethylpropyl, cyclopropyl, cyclobutyl, cyclopentyl, cyclohexyl, methoxy, ethoxy, propyloxy, 2-propyloxy, butoxy, sec-butoxy, iso-butoxy, tert-butoxy, pentoxy, 2-pentoxy, 3-pentoxy, 1,1-dimethylpropoxy, 1,2-dimethylpropoxy, fluoro, chloro, amino, dimethylamino, diethylamino, dipropylamino, diisopropylamino, dibutylamino, N-azacycloprop-1-yl, N-azacyclobut-1-yl, N-pyrrolidino, N-piperidino, N-piperazinyl, N-methylpiperazinyl, N-ethylpiperazinyl, N-propylpiperazinyl.

In one embodiment, the disclosure provides the above composition, wherein the compound has the structure of Formula IIa

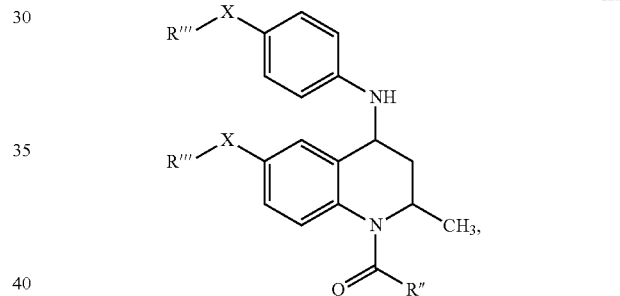

wherein R" is independently and optionally cyclopropyl, cyclobutyl, cyclopentyl, cyclohexyl, tetrahydrofuran-2-yl, tetrahydrofuran-3-yl, tetrahydrothien-2-yl, tetrahydrothien-3-yl; X is independently and optionally oxygen or sulfur; R'" substituents are independently and optionally cyclopropyl, cyclobutyl, cyclopentyl, cyclohexyl.

The disclosure provides a composition comprising a compound and isolated cells capable of differentiating into bone cells and calcium phosphate matrix wherein the compound has the structure of Formula III

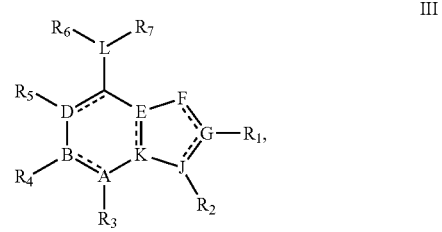

wherein A, E, F, G, J, K and L are independently and optionally Carbon or Nitrogen; B and D are Carbon; $R_1$, $R_3$, $R_4$ and $R_5$ substituents are independently and optionally hydro, methyl, trideuteromethyl, trifluoromethyl, ethyl, propyl, iso-propyl, cyclopropyl, cyclobutyl, cyclopentyl, cyclohexyl, amino, N,N-dimethylamino, N,N-diethylamino, N-phenylamino, or unsubstituted; $R_2$ substituent is independently and optionally phenyl, perdeuterophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxylphenyl, 3,4,5-trimethoxyphenyl, 2-ethoxyphenylcarbonyl, 3-ethoxyphenyl, 4-ethoxyphenyl, 2,3-diethoxyphenyl, 2,4-diethoxyphenyl, 2,5-diethoxyphenyl, 2,6-diethoxyphenyl, 3,4-diethoxyphenyl, 3,5-diethoxyphenyl, 2,3,4-triethoxyphenyl, 2,3,5-triethoxyphenyl, 2,3,6-triethoxyphenyl, 2,4,5-triethoxyphenyl, 2,4,6-triethoxylphenyl, 3,4,5-triethoxyphenyl, 2-methylphenyl, 3-methylphenyl, 4-methylphenylcarbonyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, perfluorophenyl, 2-cyanophenyl, 3-cyanophenyl, 4-cyanophenyl, 2-pyridyl, 3-pyridyl, 4-pyridyl, 2-pyrimidinyl, 2-oxazolyl, 2-thiazolyl, 2-oxazolinyl, 2-benzoxazolyl, 1,2,4-oxadiazol-5-yl, 1,2,4-oxadiazol-3-yl, 2-pyrazinyl, cyclopropyl, cyclobutyl, cyclopentyl, cyclohexyl, azacyclopropan-1-yl, azacyclopropan-2-yl, azacyclobutan-1-yl, azacyclobutan-2-yl, azacyclopentan-1-yl, azacyclopentan-2-yl, azacyclohexan-1-yl, azacyclohexan-2-yl, tetrahydrfuran-2-yl; the $R_6$ and $R_7$ substituents are independently and optionally hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, 2-(N-azacyclobutanyl)ethyl, or $R_6$ and $R_7$ are both substituted to comprise an endocyclic 6-membered N-methylpyrazine, N-ethylpyrazine, or N-propylpyrazine ring.

In one embodiment, the disclosure provides the above composition, wherein the compound has the structure of Formula IV

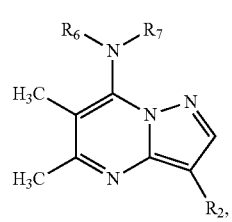

IV wherein, $R_2$ substituent is independently and optionally phenyl, perdeuterophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxylphenyl, 3,4,5-trimethoxyphenyl, 2-ethoxyphenylcarbonyl, 3-ethoxyphenyl, 4-ethoxyphenyl, 2,3-diethoxyphenyl, 2,4-diethoxyphenyl, 2,5-diethoxyphenyl, 2,6-diethoxyphenyl, 3,4-diethoxyphenyl, 3,5-diethoxyphenyl, 2,3,4-triethoxyphenyl, 2,3,5-triethoxyphenyl, 2,3,6-triethoxyphenyl, 2,4,5-triethoxyphenyl, 2,4,6-triethoxylphenyl, 3,4,5-triethoxyphenyl, 2-methylphenyl, 3-methylphenyl, 4-methylphenylcarbonyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, perfluorophenyl, 2-cyanophenyl, 3-cyanophenyl, 4-cyanophenyl, 2-pyridyl, 3-pyridyl, 4-pyridyl, 2-pyrimidinyl, 2-oxazolyl, 2-thiazolyl, 2-oxazolinyl, 2-benzoxazolyl, 1,2,4-oxadiazol-5-yl, 1,2,4-oxadiazol-3-yl, 2-pyrazinyl, cyclopropyl, cyclobutyl, cyclopentyl, cyclohexyl, azacyclopropan-1-yl, azacyclopropan-2-yl, azacyclobutan-1-yl, azacyclobutan-2-yl, azacyclopentan-1-yl, azacyclopentan-2-yl, azacyclohexan-1-yl, azacyclohexan-2-yl, tetrahydrfuran-2-yl; the $R_6$ and $R_7$ substituents are independently and optionally hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, 2-(N-azacyclobutanyl)ethyl; the $R_6$ and $R_7$ substituents are independently and optionally hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, 2-(N-azacyclobutanyl)ethyl, or $R_6$ and $R_7$ are both substituted to comprise an endocyclic 6-membered N-methylpyrazine, N-ethylpyrazine, or N-propylpyrazine ring.

In one embodiment, the disclosure provides the above composition, wherein the compound has the structure of Formula IVa

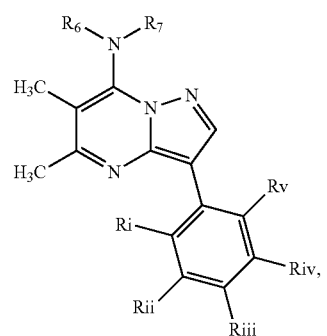

IVa wherein R₆ and R₇ are independently and optionally comprised of hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, 2-(N-azacyclobutanyl)ethyl, or R₆ and R₇ are both substituted to comprise an endocyclic 6-membered N-methylpyrazine, N-ethylpyrazine, or N-propylpyrazine ring; R₆ and R₇ are not both hydro; $R_i$, $R_{ii}$, $R_{iii}$, $R_{iv}$, and $R_v$ are independently and optionally comprised of deutero, methyl, ethyl, propyl, iso-propyl, butyl, sec-butyl, iso-butyl, tert-butyl, fluoro, chloro, cyano, trifluoromethyl, acetamido, nitro, methoxy, ethoxy, propyoxy, iso-propoxy, butoxy, sec-butoxy, iso-butoxy, tert-butoxy, 1,2,3-triazolyl, tetrazolyl.

In one embodiment, the disclosure provides the above composition, wherein the compound has the structure of Formula IVb

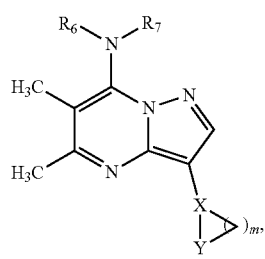

IVb wherein R₆ and R₇ are independently and optionally comprised of hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, 2-(N-azacyclobutanyl)ethyl, or R₆ and R₇ are both substituted to comprise an endocyclic 6-membered N-methylpyrazine, N-ethylpyrazine, or N-propylpyrazine ring; R₆ and R₇ are not both hydro; X and Y are independently and optionally Carbon, Oxygen, or Nitrogen; m is 0-6.

The disclosure provides a composition comprising a compound and isolated cells capable of differentiating into bone cells and calcium phosphate matrix wherein the compound has the structure of Formula V

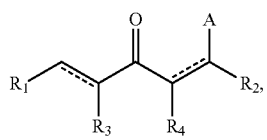

V

In one embodiment, the disclosure provides the above composition, wherein the compound has the structure of Formula VI

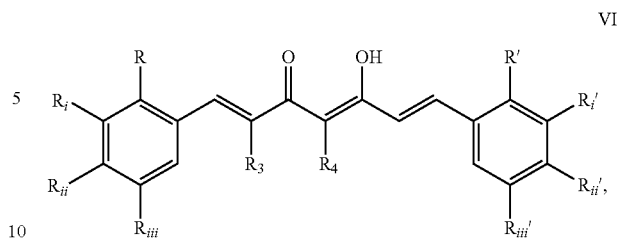

VI wherein A is independently and optionally Oxygen, Nitrogen, Sulfur, or Hydrogen; R₁ and R₂ substituents are independently and optionally hydro, alkyl, heteroalkyl, cycloalkyl, cycloheteroalkyl, alkenyl, arylalkenyl, (heteroaryl)alkenyl, aryl, heteroaryl, amino, N-alkylamino, N-(heteroalkyl)amino, N,N-dialkylamino, N-arylamino, N,N-diarylamino, N-amido, S-alkylthio, S-(heteroalkyl)thio, S-arylthio, or other moiety forming a salt or prodrug; R₃ and R₄ substituents are independently and optionally hydro, alkyl, heteroalkyl, cycloalkyl, cycloheteroalkyl, alkenyl, arylalkenyl, (heteroaryl)alkenyl, aryl, heteroaryl, halo, hydroxyl, cyano, alkoxy, aryloxy, amino, N-alkylamino, N-(heteroalkyl)amino, N,N-dialkylamino, N-arylamino, N,N-diarylamino, N-amido, S-alkylthio, S-(heteroalkyl)thio, S-arylthio, alkylcarbonyl, cycloalkylcarbonyl, (cycloheteroalkyl)carbonyl, arylcarbonyl, heteroarylcarbonyl, alkoxycarbonyl, aminocarbonyl, alkylthionyl, arylthionyl, alkylsulfonyl, heteroalkylsulfonyl, cycloalkylsulfonyl, (cycloheteroalkyl)sulfonyl, arylsulfonyl, aminosulfonyl, alkylphosphonyl, arylphosphonyl, aminophosphonyl, phosphonate, or sulfonate.

In one embodiment, the disclosure provides the above composition, wherein the compound has the structure of Formula VIa

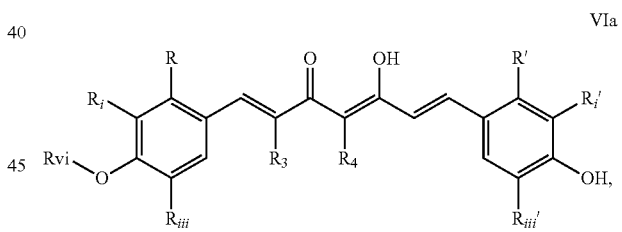

VIa wherein R, $R_{iii}$, R', $R_{iii}'$ substituents are independently and optionally hydro, hydroxyl, methoxy, ethoxy, propoxy, iso-propoxy, butoxy, sec-butoxy, iso-butoxy, tert-butoxy, methyl, ethyl, propyl, iso-propyl, butyl, sec-butyl, iso-butyl, tert-butyl, fluoro, chloro, cyano, N,N-dimethylamino, N,N-diethylamino, N,N-dipropylamino, N,N-diisopropylamino; $R_i$ and $R_i'$ substituents are independently and optionally hydro, methyl, ethyl, propyl, fluoro, chloro, cyano, N,N-dimethylamino, N,N-diethylamino, N,N-dipropylamino, N,N-diisopropylamino; the R₃ and R₄ substituents are independently and optionally hydro, methyl, ethyl, propyl, iso-propyl, butyl, sec-butyl, iso-butyl, or are both substituted with an alkyl chain to comprise a 5-membered or 6-membered ring; $R_{vi}$ substituent is glycinoyl, sarcosinoyl, alaninoyl, valinoyl, leucinoyl, isoleucinoyl, phenylalaninoyl, tyrosinoyl, tryptophanoyl, asparaginoyl, glutaminoyl, lysinoyl, aspartoyl, glutamoyl, serinoyl, threoninoyl, methioninoyl, prolinoyl, (2-amino-2-methyl)propanoyl, (2-aminocyclopropylmethanoyl, (1-aminocyclobutane)carbonoyl, 2-amino-3-methylpentanoyl, 2-amino-4-methylpentanoyl.

In one embodiment, the disclosure provides all of the above composition, wherein the isolated cells capable of differentiating into bone cells are isolated human bone marrow-derived mesenchymal stem cells, human mesenchymal stem cells of adipose tissue, human mesenchymal stem cells of blood, human mesenchymal stem cells of bone allograft or autograft tissues, human mesenchymal stem cells of dental pulp, human pericytes, human myoblasts, and human chondrocytes, human osteoprogenitor cells, urine stem cells, or their respective progenitor cells such as stem cell isolated from amniotic fluid or cord blood, embryonic stem cells, and induced pluripotent stem cells.

In one embodiment, the disclosure provides the above compositions, wherein the calcium phosphate matrix is a tricalcium phosphate ceramic or is oseoinductive.

In one embodiment, the disclosure provides compositions of any of the above compositions further comprising a calcium phosphate matrix, wherein the compound is covalently associated with the calcium phosphate matrix or is osteoinductive.

The disclosure provides a composition of cis-1-acetyl-2,6-dimethyl-N-(p-methylphenyl)-1,2,3,4-tetrahydroquinolin-4-amine, isolated cells are human bone marrow-derived mesenchymal stem cells, and a tricalcium phosphate ceramic.

The disclosure provides a composition of 3-phenyl-5,6-dimethyl-7-[N-(2-N,N-dimethylaminoethyl)amino]-pyrazolo[1,5-a]pyrimidine, isolated cells are human bone marrow-derived mesenchymal stem cells, and a tricalcium phosphate ceramic.

The disclosure provides a composition of (2S,2'S)—O,O'-(3-hydroxy-5-oxohepta-1,3,6-triene-1,7-diyl)bis(4,1-phenylene) bis(2-amino-3-methylbutanoate) HCl salt, isolated cells are human bone marrow-derived mesenchymal stem cells, and a tricalcium phosphate ceramic.

4-((1E,3Z)-3-(3-((E)-4-((L-valyl)oxy)benzylidene)-2-oxocyclohexylidene)-3-hydroxyprop-1-en-1-yl)phenyl L-valinate HCl salt.

In one embodiment, the disclosure provides the above compositions wherein the compound is covalently associated with the calcium phosphate matrix.

In one embodiment, the disclosure provides the above compositions further comprising bone morphogenetic proteins, fibroblast growth factors, platelet-derived growth factors, Wnt proteins, transforming growth factors, stromal derived factor-1, parathyroid growth hormone, vitamin D, 1,25-dihydroxy vitamin D, deoxycholic acid, teriparatide, ascorbic acid, ascorbic acid 2-phosphate, beta-glycerol phosphate, dexamethasone, or their respective salts, prodrugs, or a combination thereof.

The disclosure provides a method of inducing bone formation comprising:
(a) treating isolated cells capable of differentiating into bone cells with a compound having the structure of Formula II, the structure of Formula IV or the structure of Formula VI and
(b) administering the treated cells from step (a) to a subject.

The disclosure provides the above method further comprising the step of seeding the cells from step (a) onto a calcium phosphate matrix prior to administering the cells to a subject.

The disclosure provides a method of inducing bone formation comprising:

(a) treating isolated cells capable of differentiating into bone cells with a compound having the structure of Formula II, the structure of Formula IV or the structure of Formula VI, and
(b) administering the treated cells from step (a) to a subject, or
(b') administering the treated cells from step (a) and a calcium phosphate matrix to a subject, or
(a') administering isolated cells capable of differentiating into bone cells cells, a calcium phosphate matrix, and a compound having the structure of Formula II, the structure of Formula IV or the structure of Formula VI to a subject.

The disclosure provides a bone graft material prepared by combining isolated cells capable of differentiating into bone cells cells, a calcium phosphate matrix, and a compound having the structure of Formula II, the structure of Formula IV or the structure of Formula VI into a surgical cage.

The disclosure provides a method for increasing adherence of cells to calcium phosphate materials by treatment of cells in the presence of a calcium phosphate material with a compound of Formula II, IV, or VI.

The disclosure provides a method of inducing bone formation comprising:
(a) combining the compositions of the disclosure with a bioadhesive, and
(b) administering the composition of step (a) to a subject, or
(c) adding the composition of step (a) to a surgical cage and implantation in a subject.

The disclosure provides a method of cryopreserving the compositions of disclosure by:
(a) combining the compositions of the disclosure with a cryopreservative in a sealable tube, and
(b) freezing the tube in liquid nitrogen, and
(c) maintaining the tube in liquid nitrogen.

The disclosure provides a method of identifying new compounds that stimulate bone formation in the presence of matrices, comprising:
(a) adding test compound to cell incubations in the presence of calcium phosphate materials, and
(b) determining alkaline phosphatase functional activity in the cells of step (a), or
(c) determining Toll-like Receptor expression in the cells of step (a), or
(d) determining Runx2 and BMP2 mRNA tandem expression in the cells of step (a).

The compositions of the invention comprise the matrix (pretreated or otherwise), isolated animal cells (pretreated or otherwise), small molecules of general Formula I to VI, serum, a bioadhesive substance, as further described herein and all combinations of components.

The matrix can be further described by the following non-limiting terms:

The matrix is independently and optionally comprised of synthetic or naturally-occurring substances in a two-dimensional or three-dimensional framework that may extend in size from nanometer to multiple meters and so may consist of nanoparticles, microparticles, macroparticles and other macro objects such as sheets, planes, beds, blocks, fibers, meshes, gels, networks, and lattices, including calcium or TCP-derived materials, calcium carbonates, aragonite, calcium sulfates, Plaster of Paris, Bioglass, silicon dioxide, fluorosilicates, colloidal silica, aluminum oxide, aluminum metal alloys, titanium dioxide, titanium metal alloys, coral, sponge skeletons, processed algae, coralline hydroxyapatite, chitosan, porous or solid carbon, graphite, wood, carbonized wood, synthetic or naturally occurring polymers, poly(lactic acid), poly(glycolic acid), poly(hydroxybutyrate), poly(ε- caprolactone), poly(β-malic acid), poly(dioxanones), poly (sebacic acid), poly(adipic acid), poly(terphthalic acid), poly (imino carbonates), polyamino acids, polyphosphates, polyphosphonates, polyphosphazenes, poly(cyano acrylates), polyurethanes, polyortho esters, polydihydropyrans, polydimethylsiloxane, polymethacrylates, poly(methyl methacrylate), poly (hydroxyethyl methacrylate), polyvinyl pyrrolidone, ethyl vinyl acetate, poly(vinyl acetate); poloxamers; poloxamines, polyacetals, carbohydrate polymers, hydroxypropyl methyl cellulose, carboxymethyl cellulose, ethyl cellulose, cellulose acetate, cellulose acetate propionate, hyaluronic acid, pentosan polysulfate, starch, sucrose, lactose, fructose, agar, agarose, proteins, collagen, albumin, gelatin, glycoproteins, glycosylaminoglycans, heparin sulfate, chondroitin-4-sulfate, chondroitin-6-sulfate, keratin sulfate, poly- or oligo-(ethyleneglycol)-derivatized synthetic or natural polymers, cell-excreted biological matrix, demineralized bone matrix, devitalized bone matrix, devitalized muscle tissue, autologous bone, allogeneic bone, xenogeneic bone, cancellous bone, freeze-dried bone, cadaver bone, boneswax, beeswax, bone cement, or combinations thereof.

In another aspect the matrix may be further independently and optionally modified to modulate macroscopic shape, porosity and microporosity by chemical or physical methods, including etching, sonication, 3D printing, laser ablation, osmotic shock, electrolysis, or electroplating as applicable to a particular matrix.

In another aspect the matrix may be further independently and optionally doped with salts such as sodium chloride, sodium fluoride, sodium phosphates, sodium sulfate, lithium chloride, lithium fluoride, potassium chloride, potassium fluoride, potassium phosphates, potassium sulfate, magnesium(II) chloride, magnesium(II) fluoride, magnesium phosphates, magnesium(II) sulfate, calcium chloride, calcium fluoride, calcium phosphates, calcium sulfate, calcium oxide, as well as metal, ammonium, or organic cation salts of nitrates, carbonates, phosphates, sulfates, halides, boronates, oxides, or other salts of lithium, sodium, magnesium, potassium, calcium, rubidium, strontium, cesium, barium, scandium, titanium, zirconium, hafnium, vanadium, chromium, manganese, iron, cobalt, nickel, copper, silver, gold, zinc, aluminum, silicon, germanium, fluorine, lanthanum, europium, gadolinium, or combinations thereof.

In another aspect matrix may be further independently and optionally coated on their surface with synthetic or naturally-occurring polymers such as poly(lactic acid), poly (glycolic acid), poly(hydroxybutyrate), poly(ε-caprolactone), poly(β-malic acid), poly(dioxanones), poly(sebacic acid), poly(adipic acid), poly(terphthalic acid), poly(imino carbonates), polyamino acids, polyphosphates, polyphosphonates, polyphosphazenes, poly(cyano acrylates), polyurethanes, polyortho esters, polydihydropyrans, polydimethylsiloxane, colloidal silica, polymethacrylates, poly(methyl methacrylate), poly (hydroxyethyl methacrylate), polyvinyl pyrrolidone, ethyl vinyl acetate, poly(vinyl acetate), poloxamers, poloxamines, polyacetals, carbohydrate polymers, carboxymethyl cellulose, ethyl cellulose, cellulose acetate, cellulose acetate propionate, hydroxypropyl methyl cellulose, starch, hyaluronic acid, hyaluronic acid derivatives, pentosan polysulfate, agar, agarose, proteins, chitosan, collagen, albumin, gelatin, glycoproteins, glycosylaminoglycans, heparin sulfate, chondroitin-4-sulfate, chondroitin-6-sulfate, keratin sulfate, poly- or oligo-ethyleneglycol derived synthetic or natural polymers, cell excreted biological matrix, including mixtures or co-polymers thereof.

In another aspect the matrix may be further independently and optionally coated on their surface with biologically active proteins, including post-translationally modified proteins, recombinant proteins, or peptides and bioactive segments of said proteins, whether isolated from natural sources or synthetically prepared, as substances that are recognized to promote osteogenesis. Examples of biologically active proteins include growth factors and biologics such as the bone morphogenetic proteins, osteocalcin, osteonectin, osteopontin, thrombospondin, bone sialoprotein, osteoprotegerin, fibroblast growth factors, epidermal growth factors, vascular endothelial growth factors, platelet-derived growth factors, transforming growth factors, stromal derived growth factors, stromal derived growth factor-1, parathyroid hormone, teriparatide, leukemia inhibitory factor, insulin-like growth factor, insulin, Wnt proteins, frizzled proteins, frazzled proteins, hedgehog proteins, chordin proteins, noggin proteins, cerberus proteins, follistatin proteins, erythropoietin, collagen, fibronectin, elastin, laminin, heparin sulfate, chondroitin sulfate, keratin sulfate, albumin, or cytokines such as TNF alpha, interleukins (IL), IL-1, IL-1B, IL-2, IL-6, IL-10, IFN, SDF-1, cell excreted biological matrix, or combinations thereof.

In another aspect the matrix may be further independently and optionally absorbed with small molecules such as bisphosphonates, bisphosphonates tethered to other bioactive agents, vitamins, vitamin D, 1,25-dihydroxy vitamin D, deoxycholic acid, steroids and derivatives, antibiotics, immunosuppressive pharmacological agents, peptides, peptidomimetics, carbohydrates, oligosaccharides, glycosylamino acids, small molecules that modulate the TLR or Wnt signaling pathways, or any combination of pharmaceutical agents, drugs, or mixtures thereof;

In one embodiment, the matrix is optionally comprised of a calcium phosphate material, such as hydroxyapatite, biphasic calcium phosphate, or TCP, or mixtures thereof.

In a further embodiment, a calcium phosphate-derived matrix further comprises those calcium phosphates that are independently and optionally prepared as ceramics with different sintering temperatures, including sintering temperatures typically between 900 to 1500 degrees Celsius.

In a further embodiment, a calcium phosphate-derived ceramic matrix is independently and optionally comprised of calcium phosphate-derived ceramics with different lattice structures, such as the alpha- or beta-lattice forms of TCP.

In a further embodiment, a calcium phosphate-derived matrix is independently and optionally comprised of biphasic mixtures of calcium phosphate-derived materials, such as beta-TCP with hydroxyapatite.

In a further embodiment, a calcium phosphate-derived matrix further comprises ceramics that are independently and optionally prepared with microporosity that when defined as a percentage of micropores smaller than 10 micrometers are within the range of 0.5 and 95%.

In a further embodiment, a calcium phosphate-derived matrix further comprises ceramics that are independently and optionally prepared with various particle sizes, typically those between 100 micrometers to 10 millimeters in size.

In a preferred embodiment, the matrix comprises a calcium phosphate ceramic consisting of 90% or greater beta-tricalcium phosphate with hydroxyapatite, sintered at 1100 degrees Celsius, and ground and sieved to particle sizes of 500-1000 micrometer.

The small molecules of Formula I to VI may be defined by the following non-limiting terms:

In one aspect, the disclosure provides a compound of Formula I or a pharmaceutically acceptable salt, N-oxide, stereoisomer, or solvate thereof:

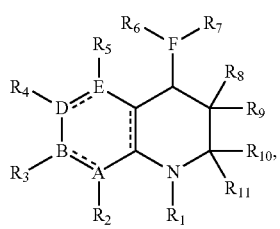

where Formula I is defined as:

A, B, E is Carbon or Nitrogen; D is Carbon; F is Nitrogen; $R_1$, $R_6$ and $R_7$ substituents are independently and optionally methylcarbonyl, trideuteromethylcarbonyl, trifluoromethylcarbonyl, 2,2,2-trifluoroethylcarbonyl, propylcarbonyl, butylcarbonyl, sec-butylcarbonyl, iso-butylcarbonyl tert-butylcarbonyl, pentylcarbonyl, 2-pentylcarbonyl, 3-pentylcarbonyl, 1,1-dimethylpropylcarbonyl, 1,2-dimethylpropylcarbonyl, 2-methoxyethylcarbonyl, 2-ethoxylethylcarbonyl, cyclopropylcarbonyl, cyclobutylcarbonyl, cyclopentylcarbonyl, cyclohexylcarbonyl, azacycloprop-2-ylcarbonyl, azacyclobut-2-ylcarbonyl, azacyclopent-2-ylcarbonyl, azacyclohex-2-ylcarbonyl, tetrahydrofuran-2-yl, tetrahydrofuran-3-yl, tetrahydrothien-2-yl, tetrahydrothien-3-yl, 2,3-dimethoxyphenylcarbonyl, 2,4-dimethoxyphenylcarbonyl, 2,5-dimethoxyphenylcarbonyl, 2,6-dimethoxyphenylcarbonyl, 3,5-dimethoxyphenylcarbonyl, 2,3,4-trimethoxyphenylcarbonyl, 2,3,5-trimethoxyphenylcarbonyl, 2,3,6-trimethoxyphenylcarbonyl, 2,4,5-trimethoxyphenylcarbonyl, 2,4,6-trimethoxylphenylcarbonyl, 3,4,5-trimethoxyphenylcarbonyl, 2-ethoxyphenylcarbonyl, 3-ethoxyphenylcarbonyl, 4-ethoxyphenylcarbonyl, 2,3-diethoxyphenylcarbonyl, 2,4-diethoxyphenylcarbonyl, 2,5-diethoxyphenylcarbonyl, 2,6-diethoxyphenylcarbonyl, 3,4-diethoxyphenylcarbonyl, 3,5-diethoxyphenylcarbonyl, 2,3,4-triethoxyphenylcarbonyl, 2,3,5-triethoxyphenylcarbonyl, 2,3,6-triethoxyphenylcarbonyl, 2,4,5-triethoxyphenylcarbonyl, 2,4,6-triethoxylphenylcarbonyl, 3,4,5-triethoxyphenylcarbonyl, 2,3-dimethylphenylcarbonyl, 2,4-dimethylphenylcarbonyl, 2,5-dimethylphenylcarbonyl, 2,6-dimethylphenylcarbonyl, 3,4-dimethylphenylcarbonyl, 3,5-dimethylphenylcarbonyl, 2-ethylphenylcarbonyl, 3-ethylphenylcarbonyl, 2,3-diethylphenylcarbonyl, 2,4-diethylphenylcarbonyl, 2,5-diethylphenylcarbonyl, 2,6-diethylphenylcarbonyl, 3,4-diethylphenylcarbonyl, 3,5-diethylphenylcarbonyl, 2,3-difluorophenylcarbonyl, 2,4-difluorophenylcarbonyl, 2,5-difluorophenylcarbonyl, 2,6-difluorophenylcarbonyl, 3,5-difluorophenylcarbonyl, perfluorophenylcarbonyl; the $R_2$, $R_3$, $R_4$, $R_5$, $R_8$, $R_9$, $R_{10}$, and $R_{11}$ substituents are independently and optionally hydro, methyl, trideuteromethyl, ethyl, 2,2,2-trifluoroethyl, propyl, 2-propyl, butyl, sec-butyl, iso-butyl, tert-butyl, pentyl, 2-pentyl, 3-pentyl, 1,1-dimethylpropyl, 1,2-dimethylpropyl, cyclopropyl, cyclobutyl, cyclopentyl, cyclohexyl, methoxy, ethoxy, propyloxy, 2-propyloxy, butoxy, sec-butoxy, iso-butoxy, tert-butoxy, pentoxy, 2-pentoxy, 3-pentoxy, 1,1-dimethylpropoxy, 1,2-dimethylpropoxy, fluoro, amino, dimethylamino, diethylamino, dipropylamino, diisopropylamino, dibutylamino, N-azacyclopropyl, N-azacyclobutyl, N-pyrrolidino, N-piperidino, N-piperazinyl, N-methylpiperazinyl, N-ethylpiperazinyl, N-propylpiperazinyl.

$R_1$, $R_2$, $R_3$, $R_4$, $R_5$, $R_6$, $R_7$, $R_8$, $R_9$, $R_{10}$, and $R_{11}$ substituents of Formula I defined above are further independently and optionally substituted with hydro, halo, $CF_3$, $C_2F_5$, hydroxyl, cyano, $(C_1-C_{12})$alkyl, $(C_1-C_{12})$heteroalkyl, alkenyl, arylalkenyl, (heteroaryl)alkenyl, $(C_3-C_{12})$cycloalkyl, $(C_3-C_{12})$cycloheteroalkyl, aryl, heteroaryl, alkoxy, aryloxy, alkanoate, aminoalkanoate, (heteroalkyl)carboxylate, arylcarboxylate, amino, N-alkylamino, N-(heteroalkyl)amino, N,N-dialkylamino, N-arylamino, N,N-diarylamino, N-amido, S-alkylthio, S-(heteroalkyl)thio, S-arylthio, alkylcarbonyl, heteroalkylcarbonyl, cycloalkylcarbonyl, (cycloheteroalkyl)carbonyl, (aminoalkyl)carbonyl, (aminoheteroalkyl)carbonyl, arylcarbonyl, heteroarylcarbonyl, alkoxycarbonyl, aryloxycarbonyl, aminocarbonyl, alkylthionyl, arylthionyl, alkylsulfonyl, heteroalkylsulfonyl, cycloalkylsulfonyl, arylsulfonyl, heteroarylsulfonyl, aminosulfonyl, alkylphosphonyl, arylphosphonyl, aminophosphonyl, phosphonate, sulfonate, or other moiety forming a salt or prodrug.

$R_2$ and $R_3$ are optionally both substituted to comprise a vicinally fused ring system, including cycloalkyl, cycloheteroalkyl, aryl, or heteroaryl fused systems.

$R_3$ and $R_4$ are optionally both substituted to comprise a vicinally fused ring system, including cycloalkyl, cycloheteroalkyl, aryl, or heteroaryl fused systems.

$R_4$ and $R_5$ are optionally both substituted to comprise a vicinally fused ring system, including cycloalkyl, cycloheteroalkyl, aryl, or heteroaryl fused systems.

$R_6$ and $R_7$ are optionally both substituted to comprise a ring system, including cycloalkyl, cycloheteroalkyl, aryl, or heteroaryl fused systems.

$R_8$ and $R_9$ are optionally taken together as oxo (=O), thiono (=S), or alkenyl (=$CR_2$) functional groups.

$R_{10}$ and $R_{11}$ are optionally taken together as oxo (=O), thiono (=S), or alkenyl (=CR2) functional groups.

$R_8$ and $R_{10}$ or $R_{11}$ are optionally substituted to comprise a ring system including cycloalkyl, cycloheteroalkyl, aryl, or heteroaryl systems.

$R_9$ and $R_{10}$ or $R_{11}$ are optionally substituted to comprise a ring system including cycloalkyl, cycloheteroalkyl, aryl, or heteroaryl systems.

$R_8$ and $R_9$, $R_{10}$ and $R_{11}$, and F are independently and optionally substituted to comprise S and R stereoisomers.

$R_1$, $R_2$, $R_3$, $R_4$, $R_5$, $R_6$, $R_7$, $R_8$, $R_9$, $R_{10}$, and $R_{11}$ are independently and optionally substituted with functional groups that contain stereoisomers, including racemic forms.

Isotopic variants of the atoms listed above where Carbon, Hydrogen, Nitrogen, Oxygen, Phosphorous, and Sulfur atoms are independently and optionally replaced with stable or radioactive isotopes, such as replacing hydrogen for deuterium, carbon-12 for carbon-13, or nitrogen-14 for nitrogen-15.

A preferred embodiment of Formula I is the substructure designated by Formula II:

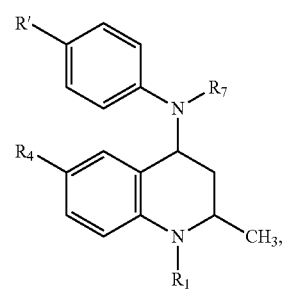

where Formula II is defined as:

$R_1$ and $R_7$ substituents are independently and optionally methylcarbonyl, trideuteromethylcarbonyl, trifluoromethylcarbonyl, 2,2,2-trifluoroethylcarbonyl, propylcarbonyl, butylcarbonyl, sec-butylcarbonyl, iso-butylcarbonyl tert-butylcarbonyl, pentylcarbonyl, 2-pentylcarbonyl, 3-pentylcarbonyl, 1,1-dimethylpropylcarbonyl, 1,2-dimethylpropylcarbonyl, 2-methoxyethylcarbonyl, 2-ethoxylethylcarbonyl, cyclopropylcarbonyl, cyclobutylcarbonyl, cyclopentylcarbonyl, cyclohexylcarbonyl, azacycloprop-2-ylcarbonyl, azacyclobut-2-ylcarbonyl, azacyclopent-2-ylcarbonyl, azacyclohex-2-ylcarbonyl, tetrahydrofuran-2-ylcarbonyl, tetrahydrofuran-3-ylcarbonyl, tetrahydrothien-2-ylcarbonyl, tetrahydrothien-3-ylcarbonyl, 2,3-dimethoxyphenylcarbonyl, 2,4-dimethoxyphenylcarbonyl, 2,5-dimethoxyphenylcarbonyl, 2,6-dimethoxyphenylcarbonyl, 3,5-dimethoxyphenylcarbonyl, 2,3,4-trimethoxyphenylcarbonyl, 2,3,5-trimethoxyphenylcarbonyl, 2,3,6-trimethoxyphenylcarbonyl, 2,4,5-trimethoxyphenylcarbonyl, 2,4,6-trimethoxylphenylcarbonyl, 3,4,5-trimethoxyphenylcarbonyl, 2-ethoxyphenylcarbonyl, 3-ethoxyphenylcarbonyl, 4-ethoxyphenylcarbonyl, 2,3-diethoxyphenylcarbonyl, 2,4-diethoxyphenylcarbonyl, 2,5-diethoxyphenylcarbonyl, 2,6-diethoxyphenylcarbonyl, 3,4-diethoxyphenylcarbonyl, 3,5-diethoxyphenylcarbonyl, 2,3,4-triethoxyphenylcarbonyl, 2,3,5-triethoxyphenylcarbonyl, 2,3,6-triethoxyphenylcarbonyl, 2,4,5-triethoxyphenylcarbonyl, 2,4,6-triethoxylphenylcarbonyl, 3,4,5-triethoxyphenylcarbonyl, 2,3-dimethylphenylcarbonyl, 2,4-dimethylphenylcarbonyl, 2,5-dimethylphenylcarbonyl, 2,6-dimethylphenylcarbonyl, 3,4-dimethylphenylcarbonyl, 3,5-dimethylphenylcarbonyl, 2-ethylphenylcarbonyl, 3-ethylphenylcarbonyl, 2,3-diethylphenylcarbonyl, 2,4-diethylphenylcarbonyl, 2,5-diethylphenylcarbonyl, 2,6-diethylphenylcarbonyl, 3,4-diethylphenylcarbonyl, 3,5-diethylphenylcarbonyl, 2,3-difluorophenylcarbonyl, 2,4-difluorophenylcarbonyl, 2,5-difluorophenylcarbonyl, 2,6-difluorophenylcarbonyl, 3,5-difluorophenylcarbonyl, perfluorophenylcarbonyl; $R_4$ and R' substituents are independently and optionally hydro, methyl, trideuteromethyl, ethyl, 2,2,2-trifluoroethyl, propyl, 2-propyl, butyl, sec-butyl, iso-butyl, tert-butyl, pentyl, 2-pentyl, 3-pentyl, 1,1-dimethylpropyl, 1,2-dimethylpropyl, cyclopropyl, cyclobutyl, cyclopentyl, cyclohexyl, methoxy, ethoxy, propyloxy, 2-propyloxy, butoxy, sec-butoxy, iso-butoxy, tert-butoxy, pentoxy, 2-pentoxy, 3-pentoxy, 1,1-dimethylpropoxy, 1,2-dimethylpropoxy, fluoro, amino, dimethylamino, diethylamino, dipropylamino, diisopropylamino, dibutylamino, N-azacyclopropyl, N-azacyclobutyl, N-pyrrolidino, N-piperidino, N-piperazinyl, N-methylpiperazinyl, N-ethylpiperazinyl, N-propylpiperazinyl.

In a further preferred embodiment of Formula II, R is methyl, R' is cyclopropylcarbonyl, and R" is hydro.

In a further preferred embodiment of Formula II, R is methoxy, R' is isopropylcarbonyl, and R" is hydro.

In a further preferred embodiment of Formula II, R is methyl, R' is methylcarbonyl, and R" is hydro.

In a preferred embodiment of Formula II, the two stereocenters at the C2 and C4 have cis relative stereochemistry such that C2 and C4 can be of either R and S configuration respectively, or S and R configuration respectively, or a single enantiomer.

A preferred embodiment of Formula II is the substructure designated by Formula IIa:

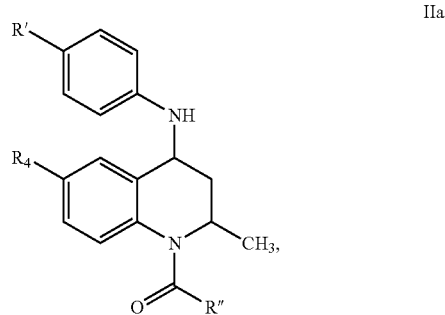

where Formula IIa is defined as:

R" is independently and optionally comprised of methyl, trideuteromethyl, trifluoromethyl, propyl, butyl, sec-butyl, iso-butyl tert-butyl, pentyl, 2-pentyl, 3-pentyl, 1,1-dimethylpropyl, 1,2-dimethylpropyl, 2-methoxyethyl, 2-ethoxylethyl, cyclopropyl, cyclobutyl, cyclopentyl, cyclohexyl, tetrahydrofuran-2-yl, tetrahydrofuran-3-yl, tetrahydrothien-2-yl, tetrahydrothien-3-yl, 2,3-dimethoxyphenyl, 2,4-dimethoxyphenyl, 2,5-dimethoxyphenyl, 2,6-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxylphenyl, 3,4,5-trimethoxyphenyl, 2-ethoxyphenyl, 3-ethoxyphenyl, 4-ethoxyphenyl, 2,3-diethoxyphenyl, 2,4-diethoxyphenyl, 2,5-diethoxyphenyl, 2,6-diethoxyphenyl, 3,4-diethoxyphenyl, 3,5-diethoxyphenyl, 2,3,4-triethoxyphenyl, 2,3,5-triethoxyphenyl, 2,3,6-triethoxyphenyl, 2,4,5-triethoxyphenyl, 2,4,6-triethoxylphenyl, 3,4,5-triethoxyphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-ethylphenylcarbonyl, 3-ethylphenyl, 2,3-diethylphenyl, 2,4-diethylphenyl, 2,5-diethylphenyl, 2,6-diethylphenyl, 3,4-diethylphenyl, 3,5-diethylphenyl, 2,3-difluorophenyl, 2,4-difluorophenyl, 2,5-difluorophenyl, 2,6-difluorophenyl, 3,5-difluorophenyl, perfluorophenyl; the $R_4$ and R' substituents are independently and optionally hydro, deuterio, methyl, trideuteromethyl, ethyl, 2,2,2-trifluoroethyl, propyl, 2-propyl, butyl, sec-butyl, iso-butyl, tert-butyl, pentyl, 2-pentyl, 3-pentyl, 1,1-dimethylpropyl, 1,2-dimethylpropyl, cyclopropyl, cyclobutyl, cyclopentyl, cyclohexyl, methoxy, ethoxy, propyloxy, 2-propyloxy, butoxy, sec-butoxy, iso-butoxy, tert-butoxy, pentoxy, 2-pentoxy, 3-pentoxy, 1,1-dimethylpropoxy, or 1,2-dimethylpropoxy.

In a further preferred embodiment of Formula IIa, $R_4$ and R' are methyl, R" is cyclopropylcarbonyl, and $R_7$ is hydro.

In a further preferred embodiment of Formula IIa, $R_4$ and R' are methoxy, R" is isopropylcarbonyl, and $R_7$ is hydro.

In a preferred embodiment of Formula IIa, the two stereocenters at the C2 and C4 have cis relative stereochemistry such that C2 and C4 can be of either R and S configuration respectively, or S and R configuration respectively, or a single enantiomer.

A preferred embodiment of Formula II is the substructure designated by Formula IIa:

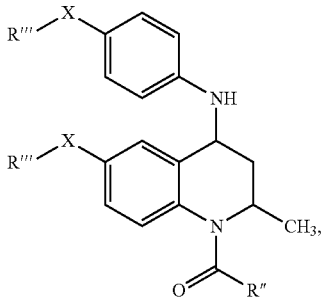

IIa wherein Formula IIa is defined as:

R″ is independently and optionally cyclopropyl, cyclobutyl, cyclopentyl, cyclohexyl, tetrahydrofuran-2-yl, tetrahydrofuran-3-yl, tetrahydrothien-2-yl, tetrahydrothien-3-yl; X is independently and optionally oxygen or sulfur; R‴ substituents are independently and optionally cyclopropyl, cyclobutyl, cyclopentyl, cyclohexyl.

In another aspect, the disclosure provides a compound of Formula III or a pharmaceutically acceptable salt, N-oxide or solvate thereof:

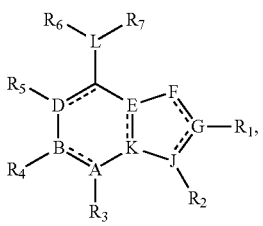

III wherein Formula III is defined as:

A, E, F, G, J, K and L are independently and optionally Carbon or Nitrogen; B and D are Carbon; $R_1$, $R_3$, $R_4$ and $R_5$ substituents are independently and optionally hydro, methyl, trideuteromethyl, ethyl, propyl, cyclopropyl, cyclobutyl, cyclopentyl, cyclohexyl, amino, N,N-dimethylamino, N,N-diethylamino, N-phenylamino; $R_2$ substituent is independently and optionally phenyl, perdeuterophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxyphenyl, 3,4,5-trimethoxyphenyl, 2-ethoxyphenylcarbonyl, 3-ethoxyphenyl, 4-ethoxyphenyl, 2,3-diethoxyphenyl, 2,4-diethoxyphenyl, 2,5-diethoxyphenyl, 2,6-diethoxyphenyl, 3,4-diethoxyphenyl, 3,5-diethoxyphenyl, 2,3,4-triethoxyphenyl, 2,3,5-triethoxyphenyl, 2,3,6-triethoxyphenyl, 2,4,5-triethoxyphenyl, 2,4,6-triethoxyphenyl, 3,4,5-triethoxyphenyl, 2-methylphenyl, 3-methylphenyl, 4-methylphenylcarbonyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, perfluorophenyl, 2-cyanophenyl, 3-cyanophenyl, 4-cyanophenyl, 2-pyridyl, 3-pyridyl, 4-pyridyl, 2-pyrimidinyl, 2-oxazolyl, 2-thiazolyl, 2-oxazolinyl, 2-benzoxazolyl, 5-(1,2,4-oxadiazolyl), 3-(1,2,4-oxadiazolyl), 2-pyrazinyl, cyclopropyl, cyclobutyl, cyclopentyl, cyclohexyl, azacyclopropan-1-yl, azacyclopropan-2-yl, azacyclobutan-1-yl, azacyclobutan-2-yl, azacyclopentan-1-yl, azacyclopentan-2-yl, azacyclohexan-1-yl, azacyclohexan-2-yl, tetrahydrfuran-2-yl; the $R_6$ and $R_7$ substituents are independently and optionally hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, or 2-(N-azacyclobutanyl)ethyl.

$R_1$, $R_2$, $R_3$, $R_4$, $R_5$, $R_6$ and $R_7$ substituents of Formula III defined above are further independently and optionally substituted with hydro, halo, $CF_3$, $C_2F_5$, hydroxyl, cyano, $(C_1-C_{12})$alkyl, $(C_1-C_{12})$heteroalkyl, alkenyl, arylalkenyl, (heteroaryl)alkenyl, $(C_3-C_{12})$cycloalkyl, $(C_3-C_{12})$cycloheteroalkyl, aryl, heteroaryl, alkoxy, aryloxy, alkanoate, aminoalkanoate, (heteroalkyl)carboxylate, arylcarboxylate, amino, N-alkylamino, N-(heteroalkyl)amino, N,N-dialkylamino, N-arylamino, N,N-diarylamino, N-amido, S-alkylthio, S-(heteroalkyl)thio, S-arylthio, alkylcarbonyl, heteroalkylcarbonyl, cycloalkylcarbonyl, (cycloheteroalkyl)carbonyl, (aminoalkyl)carbonyl, (aminoheteroalkyl)carbonyl, arylcarbonyl, heteroarylcarbonyl, alkoxycarbonyl, aryloxycarbonyl, aminocarbonyl, alkylthionyl, arylthionyl, alkylsulfonyl, heteroalkylsulfonyl, cycloalkylsulfonyl, arylsulfonyl, heteroarylsulfonyl, aminosulfonyl, alkylphosphonyl, arylphosphonyl, aminophosphonyl, phosphonate, sulfonate, or other moiety forming a salt or prodrug.

$R_1$ and $R_2$ are optionally both substituted to comprise a vicinally fused ring system, including cycloalkyl, cycloheteroalkyl, aryl, or heteroaryl fused systems;

$R_2$ and $R_3$ are optionally both substituted to comprise a fused ring system, including cycloalkyl, cycloheteroalkyl, aryl, or heteroaryl fused systems.

$R_3$ and $R_4$ are optionally both substituted to comprise a vicinally fused ring system, including cycloalkyl, cycloheteroalkyl, aryl, or heteroaryl fused systems.

$R_4$ and $R_5$ are optionally both substituted to comprise a vicinally fused ring system, including cycloalkyl, cycloheteroalkyl, aryl, or heteroaryl fused systems.

$R_6$ and $R_7$ are optionally both substituted to form a ring system, including cycloalkyl, cycloheteroalkyl, aryl, or heteroaryl systems.

$R_1$, $R_2$, $R_3$, $R_4$ and $R_5$ are oxo (=O), thiono (=S), or alkenyl (=CR_2) functional groups or corresponding tautomers.

$R_1$, $R_2$, $R_3$, $R_4$, $R_5$, $R_6$ and $R_7$ are independently and optionally substituted with functional groups imparting stereoisomers that include S and R stereoisomers, or racemic forms.

Isotopic variants of the above atoms where Carbon, Hydrogen, Nitrogen, Oxygen, Phosphorous, and Sulfur atoms are independently and optionally replaced with stable or radioactive isotopes, such as replacing hydrogen for deuterium, carbon-12 for carbon-13, or nitrogen-14 for nitrogen-15.

A preferred embodiment of Formula III is the substructure designated by Formula IV:

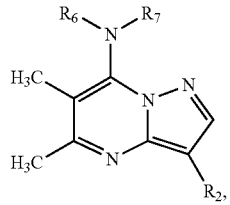

IV wherein $R_2$ substituent is independently and optionally phenyl, perdeuterophenyl, 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxylphenyl, 3,4,5-trimethoxyphenyl, 2-ethoxyphenylcarbonyl, 3-ethoxyphenyl, 4-ethoxyphenyl, 2,3-diethoxyphenyl, 2,4-diethoxyphenyl, 2,5-diethoxyphenyl, 2,6-diethoxyphenyl, 3,4-diethoxyphenyl, 3,5-diethoxyphenyl, 2,3,4-triethoxyphenyl, 2,3,5-triethoxyphenyl, 2,3,6-triethoxyphenyl, 2,4,5-triethoxyphenyl, 2,4,6-triethoxylphenyl, 3,4,5-triethoxyphenyl, 2-methylphenyl, 3-methylphenyl, 4-methylphenylcarbonyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 3,5-diethylphenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, perfluorophenyl, 2-cyanophenyl, 3-cyanophenyl, 4-cyanophenyl, 2-pyridyl, 3-pyridyl, 4-pyridyl, 2-pyrimidinyl, 2-oxazolyl, 2-thiazolyl, 2-oxazolinyl, 2-benzoxazolyl, 5-(1,2,4-oxadiazolyl), 3-(1,2,4-oxadiazolyl), or 2-pyrazinyl; the $R_6$ and $R_7$ substituents are independently and optionally hydro, 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl)ethyl, or 2-(N-azacyclobutanyl)ethyl.

In another preferred embodiment of Formula IV, the $R_6$ and $R_7$ substituents are both substituted to comprise a nitrogen-containing ring system of 4-(N-methylpyrazinyl), 4-(N-ethylpyrazinyl), 4-(N-propylpyrazinyl), 4-(N-butylpyrazinyl), N-piperadinyl, N-pyrrolidinyl, N-azacyclobutyl, or N-azacyclopropanyl wherein the nitrogen-containing ring system is named as a substituent.

In a further preferred embodiment of Formula IV, $R_2$ is 4-fluorophenyl, $R_6$ is 2-(dimethylamino)ethyl, and $R_7$ is hydro.

In a further preferred embodiment of Formula IV, $R_2$ is phenyl, $R_6$ is 2-(dimethylamino)ethyl, and $R_7$ is hydro.

A preferred embodiment of Formula III is the substructure designated by Formula IVa:

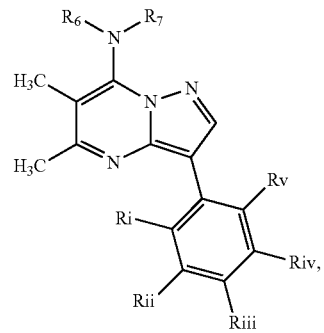

IVa wherein $R_6$ is independently and optionally comprised of 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl) ethyl, or 2-(N-azacyclobutanyl)ethyl; $R_7$ is hydro; $R_i$, $R_{ii}$, $R_{iii}$, $R_{iv}$, and $R_v$ are independently and optionally comprised of deutero, methyl, ethyl, propyl, iso-propyl, butyl, sec-butyl, iso-butyl, tert-butyl, fluoro, chloro, cyano, trifluoromethyl, acetamido, nitro, methoxy, ethoxy, propyoxy, isopropoxy, butoxy, sec-butoxy, iso-butoxy, tert-butoxy, 1,2,3-triazolyl, tetrazolyl.

In another preferred embodiment of Formula IVa, the $R_6$ and $R_7$ substituents are both substituted to comprise a nitrogen-containing ring system of 4-(N-methylpyrazinyl), 4-(N-ethylpyrazinyl), 4-(N-propylpyrazinyl), 4-(N-butylpyrazinyl), N-piperadinyl, N-pyrrolidinyl, N-azacyclobutyl, or N-azacyclopropanyl wherein the nitrogen-containing ring system is named as a substituent.

A preferred embodiment of Formula III is the substructure designated by Formula IVb:

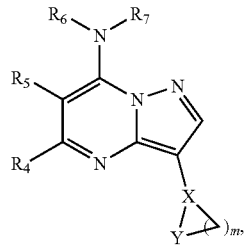

IVb wherein Formula IVb is defined as:

$R_6$ is independently and optionally comprised of 2-(dimethylamino)ethyl, 2-(diethylamino)ethyl, 2-(dipropylamino)ethyl, 3-(dimethylamino)propyl, 3-(diethylamino)propyl, 3-(dipropylamino)propyl, 2-(dimethylamino)propyl, 2-(diethylamino)propyl, 2-(dipropylamino)propyl, 2-(pyrrolidinyl)ethyl, 2-(piperadinyl)ethyl, 2-(piperazinyl)ethyl, 2-(N-methyl-piperazinyl)ethyl, 2-(N-ethyl-piperazinyl)ethyl, 2-(N-propyl-piperazinyl)ethyl, 2-(N-azacyclopropanyl) ethyl, or 2-(N-azacyclobutanyl)ethyl; $R_7$ is hydro; X and Y are independently and optionally Carbon, Oxygen, or Nitrogen; m is 0-6.

In another preferred embodiment of Formula IVb, the the $R_6$ and $R_7$ substituents are both substituted to comprise a nitrogen-containing ring system of 4-(N-methylpyrazinyl), 4-(N-ethylpyrazinyl), 4-(N-propylpyrazinyl), 4-(N-butylpyrazinyl), N-piperadinyl, N-pyrrolidinyl, N-azacyclobutyl, or N-azacyclopropanyl wherein the nitrogen-containing ring system is named as a substituent.

In another embodiment, the disclosure provides a compound of Formula V or a pharmaceutically acceptable salt, N-oxide or solvate thereof:

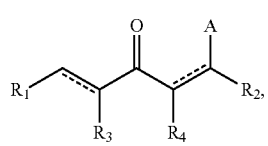

V wherein Formula V is defined as:

A is independently and optionally Oxygen, Nitrogen, Sulfur, or Hydrogen; $R_1$ and $R_2$ substituents are independently and optionally hydro, alkyl, heteroalkyl, cycloalkyl, cycloheteroalkyl, alkenyl, arylalkenyl, (heteroaryl)alkenyl, aryl, heteroaryl, amino, N-alkylamino, N-(heteroalkyl) amino, N,N-dialkylamino, N-arylamino, N,N-diarylamino, N-amido, S-alkylthio, S-(heteroalkyl)thio, S-arylthio, or other moiety forming a salt or prodrug; $R_3$ and $R_4$ substituents are independently and optionally hydro, alkyl, heteroalkyl, cycloalkyl, cycloheteroalkyl, alkenyl, arylalkenyl, (heteroaryl)alkenyl, aryl, heteroaryl, halo, hydroxyl, cyano, alkoxy, aryloxy, amino, N-alkylamino, N-(heteroalkyl) amino, N,N-dialkylamino, N-arylamino, N,N-diarylamino, N-amido, S-alkylthio, S-(heteroalkyl)thio, S-arylthio, alkylcarbonyl, cycloalkylcarbonyl, (cycloheteroalkyl)carbonyl, arylcarbonyl, heteroarylcarbonyl, alkoxycarbonyl, aminocarbonyl, alkylthionyl, arylthionyl, alkylsulfonyl, heteroalkylsulfonyl, cycloalkylsulfonyl, (cycloheteroalkyl)sulfonyl, arylsulfonyl, aminosulfonyl, alkylphosphonyl, arylphosphonyl, aminophosphonyl, phosphonate, sulfonate, or other moiety forming a salt or prodrug.

$R_1$, $R_2$, $R_3$ and $R_4$ substituents of Formula V defined above are further independently and optionally substituted with hydro, halo, $CF_3$, $C_2F_5$, hydroxyl, cyano, $(C_1-C_{12})$ alkyl, $(C_1-C_{12})$heteroalkyl, alkenyl, arylalkenyl, (heteroaryl) alkenyl, $(C_3-C_{12})$cycloalkyl, $(C_3-C_{12})$cycloheteroalkyl, aryl, heteroaryl, alkoxy, aryloxy, alkanoate, aminoalkanoate, (heteroalkyl)carboxylate, arylcarboxylate, amino, N-alkylamino, N-(heteroalkyl)amino, N,N-dialkylamino, N-arylamino, N,N-diarylamino, N-amido, S-alkylthio, S-(heteroalkyl)thio, S-arylthio, alkylcarbonyl, heteroalkylcarbonyl, cycloalkylcarbonyl, (cycloheteroalkyl)carbonyl, (aminoalkyl)carbonyl, (aminoheteroalkyl)carbonyl, arylcarbonyl, heteroarylcarbonyl, alkoxycarbonyl, aryloxycarbonyl, aminocarbonyl, alkylthionyl, arylthionyl, alkylsulfonyl, heteroalkylsulfonyl, cycloalkylsulfonyl, arylsulfonyl, heteroarylsulfonyl, aminosulfonyl, alkylphosphonyl, arylphosphonyl, aminophosphonyl, phosphonate, sulfonate, or other moiety forming a salt or prodrug.

$R_1$, $R_2$, $R_3$ and $R_4$ substituents of Formula V defined above are further independently and optionally substituted with carboxylates of naturally-occurring amino acids.

$R_3$ and $R_4$ are optionally both substituted to comprise a ring system, such as cycloalkyl, cycloheteroalkyl, aryl, or heteroaryl fused systems.

$R_1$, $R_2$, $R_3$ and $R_4$ are independently and optionally substituted with functional groups imparting stereoisomers that include S and R stereoisomers, or racemic forms.

Isotopic variants of the atoms listed above where Carbon, Hydrogen, Nitrogen, Oxygen, Phosphorous, and Sulfur atoms are independently and optionally replaced with stable or radioactive isotopes, such as replacing hydrogen for deuterium, carbon-12 for carbon-13, or nitrogen-14 for nitrogen-15.

A preferred embodiment of Formula V is the substructure designated by Formula VI:

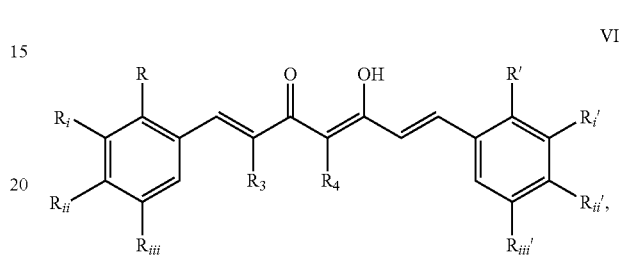

VI wherein Formula VI is defined as:

R, $R_i$, $R_{ii}$, $R_{iii}$, R', $R_i'$, $R_{ii}'$, $R_{iii}'$, $R_3$ and $R_4$ are substituents independently and optionally comprised of hydro, alkyl, heteroalkyl, cycloalkyl, cycloheteroalkyl, alkenyl, arylalkenyl, (heteroaryl)alkenyl, aryl, heteroaryl, halo, hydroxyl, cyano, alkoxy, aryloxy, alkanoate, aminoalkanoate, (heteroalkyl)carboxylate, arylcarboxylate, amino, N-alkylamino, N-(heteroalkyl)amino, N,N-dialkylamino, N-arylamino, N,N-diarylamino, N-amido, S-alkylthio, S-(heteroalkyl)thio, S-arylthio, alkylcarbonyl, cycloalkylcarbonyl, (cycloheteroalkyl)carbonyl, (aminoalkyl)carbonyl, (aminoheteroalkyl)carbonyl, arylcarbonyl, heteroarylcarbonyl, alkoxycarbonyl, aminocarbonyl, alkylthionyl, arylthionyl, alkylsulfonyl, arylsulfonyl, aminosulfonyl, alkylphosphonyl, arylphosphonyl, aminophosphonyl, phosphonate, sulfonate, or other moiety forming a salt or prodrug.

$R_3$ and $R_4$ are optionally both substituted to comprise a ring system, including 5- and 6-membered ring systems such as substituted cycloalkyl, cycloheteroalkyl, aryl, or heteroaryl systems.

In a preferred embodiment of Formula VI, R, $R_i$, $R_{ii}$, $R_{iii}$, R', $R_i'$, $R_{ii}'$, $R_{iii}'$ substituents are independently and optionally hydro, methoxy, ethoxy, 2,2,2-trifluoroethoxy, propoxy, butoxy, sec-butoxy, iso-butoxy, tert-butoxy, pentoxy, 2-pentoxy, 3-pentoxy, 1,1-dimethylpropoxy, 1,2-dimethylpropoxy, methyl, trideuteromethyl, trifluoromethyl, ethyl, 2,2,2-trifluoroethyl, propyl, isopropyl, 1,1,1,3,3,3-hexafluoro-2-propyl, butyl, sec-butyl, iso-butyl, tert-butyl, cyclopropyl, cyclobutyl, cyclopentyl, cyclohexyl, fluoro, cyano, glycine carboxylate, sarcosine carboxylate, alanine carboxylate, valine carboxylate, leucine carboxylate, isoleucine carboxylate, phenylalanine carboxylate, tyrosine carboxylate, tryptophan carboxylate, asparagine carboxylate, glutamine carboxylate, lysine carboxylate, proline carboxylate, 2-amino-2-methyl-propionate, 1-aminocyclopropylcarboxylate, 1-aminocyclobutanecarboxylate, amino, dimethylamino, diethylamino, dipropylamino, diisopropylamino, dibutylamino, N-azacyclopropyl, N-azacyclobutyl, N-pyrrolidino, N-piperidino, N-piperazinyl, N-methylpiperazinyl, N-ethylpiperazinyl, N-propylpiperazinyl; $R_3$ and $R_4$ are independently and optionally hydro, methyl, trideuteromethyl, trifluoromethyl, ethyl, propyl, isopropyl, butyl, sec-butyl, iso-butyl, tert-butyl, cyclopropyl, cyclobutyl, cyclopentyl, cyclohexyl; $R_3$ and $R_4$ substituents are independently and optionally hydro, methyl, ethyl, propyl, butyl.

In the preferred embodiment of Formula VI above, $R_3$ and $R_4$ are optionally both substituted to together constitute a —$C_3H_6$— alkyl chain that provides a 6-membered cyclohexanone ring system.

In a further preferred embodiment of Formula VI, R, $R_i$, $R_{iii}$, R', $R_i'$, $R_{ii}'$, $R_{iii}'$ substituents are hydro (H), $R_3$ and $R_4$ substituents are both substituted to form a 6-membered ring system through a —$C_3H_6$— alkyl chain, and $R_{iii}$, and $R_{ii}'$ substituents are both L-valine carboxylate hydrochloride salt.

In a further preferred embodiment of Formula VI, R, $R_i$, $R_{iii}$, R', $R_i'$, $R_{iii}'$, $R_{iv}$ and $R_v$ substituents are hydro (H), $R_{ii}$, and $R_{ii}'$ substituents are both O-L-valine carboxylate hydrochloride salt.

In a further preferred embodiment of Formula VI, R, $R_i$, $R_{iii}$, R', $R_i'$, $R_{ii}'$, $R_{iii}'$, $R_{iv}$ and $R_v$ substituents are hydro (H), R substituent is O-L-valine carboxylate hydrochloride salt.

In a further preferred embodiment of Formula V is the substructure designated by Formula VIa:

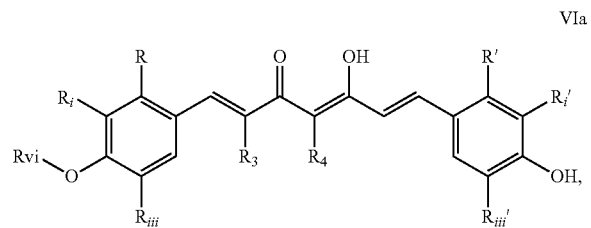

VIa wherein Formula VIa is defined as:

R, $R_{iii}$, R', $R_{iii}'$ substituents are independently and optionally hydro, hydroxyl, methoxy, ethoxy, propoxy, isopropoxy, butoxy, sec-butoxy, iso-butoxy, tert-butoxy, methyl, ethyl, propyl, iso-propyl, butyl, sec-butyl, iso-butyl, tert-butyl, fluoro, chloro, cyano, N,N-dimethylamino, N,N-diethylamino, N,N-dipropylamino, N,N-diisopropylamino; $R_i$ and $R_i'$ substituents are independently and optionally hydro, methyl, ethyl, propyl, iso-propyl, butyl, sec-butyl, iso-butyl, tert-butyl, fluoro, chloro, cyano, N,N-dimethylamino, N,N-diethylamino, N,N-dipropylamino, N,N-diisopropylamino; $R_3$ and $R_4$ substituents are independently and optionally hydro, methyl, ethyl, propyl, iso-propyl, butyl, sec-butyl, iso-butyl, tert-butyl; substituent is glycinoyl, sarcosinoyl, alaninoyl, valinoyl, leucinoyl, isoleucinoyl, phenylalaninoyl, tyrosinoyl, tryptophanoyl, asparaginoyl, glutaminoyl, lysinoyl, aspartoyl, glutamoyl, serinoyl, threoninoyl, methioninoyl, prolinoyl, (2-amino-2-methyl)propanoyl, (2-aminocyclopropylmethanoyl, (1-aminocyclobutane)carbonoyl, 2-amino-3-methylpentanoyl, 2-amino-4-methylpentanoyl.

In the preferred embodiment of Formula VIa above, $R_3$ and $R_4$ are optionally both substituted to together constitute a —$C_3H_6$— or $C_2H_4$— alkyl chain that provides either a 6-membered or 5-membered cyclohexanone ring system.

The compositions of the invention comprising a biologically active small molecule and matrix and/or cells were described in the following non-limiting terms:

Wherein the compositions of a compound and matrix were obtained by mixing the compound and matrix as a solution, suspension, biphasic solid-liquid mixture, dry powder, gel, putty, or by mixing independent preparations of the compound and matrix by, for example, adding a solution of compound to a matrix, or by adding a solution of compound to a suspension of matrix in another solution, as non-limiting examples of the compositions of the invention, or Wherein the compositions of compound and matrix and isolated cells were obtained by adding matrix to isolated cells that are present either as a suspension in a suitable liquid phase or adherent cells in a container, such as cell culture dishes, plates, a bioreactor, or a matrix, followed by the addition of a compound solution to the resulting mixture, as a non-limiting example of how to prepare the compositions of the disclosure, or Wherein the compositions of a compound of Formula I to VI and matrix (i.e. a pre-treated matrix) was obtained by adsorbing the small molecule to the surface of the matrix by either physisorption or chemisorption as a non-limiting example of the compositions of the invention, or Wherein the compositions of a pre-treated matrix and isolated cells was obtained by adding a matrix that has been adsorbed with a compound of Formula I to VI to isolated cells that are present either as a suspension in a suitable liquid phase or adherent cells in a container, such as cell culture dishes, plates, a bioreactor, a matrix, as non-limiting examples of how to prepare the compositions of the invention, or Wherein the compositions of a compound and matrix and/or cells were mixed at different times, including the introduction or removal of either component at a different times as a non-limiting example of the compositions of the invention, or Wherein the compositions of the invention can be considered to encompass the use of a known osteogenic small molecule and animal cells in the presence of matrix, such that the combination of agents increases cell differentiation, or cell proliferation, or cell migration in excess of either agent used independently, or Wherein the compositions of a compound of Formula I to VI and matrix that are in the presence of isolated cells included bone marrow-derived stromal cells or mesenchymal stem cells, mesenchymal stem cells of adipose tissue, mesenchymal stem cells of blood, mesenchymal stem cells of bone allograft or autograft tissues, mesenchymal stem cells of dental pulp, pericytes, myoprogenitor cells, myoblasts, chondrocytes, osteoprogenitor cells, osteochondroprogenitor cells, hematopoietic stem cells, monocytes, lymphocytes, or T-cells, urine stem cells, or their respective progenitor cells such as stem cells isolated from amniotic fluid or cord blood, embryonic stem cells, and induced pluripotent stem cells, as non-limiting examples, or Wherein the above compositions further comprise cells from allogeneic, autologous, or xenologous sources, including allogeneic bone tissue, allogeneic cells of the bone marrow, allogeneic cells of the bone marrow aspirates, allogeneic cells of the blood, allogeneic cells of cartilage, allogeneic osteoblasts, devitalized allogeneic bone tissue, demineralized allogeneic bone tissue, induced pluripotent stem cells that are derived from allogeneic cells or tissue, allogeneic embryonic stem cells, autologous bone, autologous cells of the bone marrow, autologous cells of the bone marrow aspirates, autologous cells of the blood, autologous cells of cartilage, autologous osteoblasts, devitalized autologous bone tissue, demineralized autologous bone tissue, induced pluripotent stem cells that are derived from autologous cells or tissue, autologous embryonic stem cells, xenologous bone tissue, xenologous cells of the bone marrow, xenologous cells of the bone marrow aspirates, xenologous cells of the blood, xenologous osteoblasts, devitalized xenologous bone tissue, demineralized xenologous bone tissue, xenologous cells of cartilage, induced pluripotent stem cells that are derived from xenologous cells or tissue, xenologous embryonic stem cells, as non-limiting examples, or Wherein the above compositions optionally included the addition of bioadhesive agents that can bind the compounds of Formula I to VI and/or matrix and/or cells, such as the use of a Fibrin gel by way of a non-limiting example, or Wherein the compositions of Formula I to VI and matrix and cells were independently or optionally combined with a carrier substance, such as gels, putties, osteoconductive materials, other osteoinductive materials, bone cements, and synthetic or naturally-occurring polymeric materials used in medicinal applications and medical implant procedures, including synthetic polymers such as alkylene oxide polymers and its copolymers, poloxamers comprised of triblock copolymers of polyoxypropylene and polyoxyethylene for example, as well as boneswax, beeswax, gelatin, laminin, calcium alginate, agarose, collagen(s), fibrin, fibronectin, carbohydrate polymers, hyaluronic acid and derivatives, saccharides, gels, hydrogels, supramolecular gels, supramolecular polymers, putties, demineralized or devitalized tissues, other matrices, or blood and serum that congeals to provide an implantable cohesive mixture, as non-limiting examples, or Wherein the compositions of the invention are added to a surgical implant device in the form of a surgical cage or injectable syringe, or Wherein the compositions of Formula I to VI and matrix are independently or optionally combined with cells and/or carrier substance in a surgical device, surgical cage, or with surgical instrumentation for use in bone repair, including surgical cages for use in spinal fusion procedures that are comprised of titanium alloys or titanium dioxide and poly (ether etherketones) polymers, or with bone graft substances for implantation in bone fractures or defects, or for injection by medical syringe at or near the site of a bone defect, or Wherein the compositions of Formula I to VI and matrix that are optionally combined with cells, carrier substance, or surgical implant device as described above, is further combined with a substance that facilitates medical implantation, including antibiotics or immunosuppressive agents used for such purposes, or Wherein the above compositions of the invention that are optionally combined with a carrier substance, were further combined with a substance that facilitates cryopreservation, or In a preferred embodiment of the composition of the invention, the isolated cells were human adult stem cells, such as human bone marrow-derived mesenchymal stem cells. Isolated human bone marrow-derived mesenchymal stem cells were cultured in the presence of a compound of Formula I to VI and a tricalcium phosphate ceramic matrix for 8 days. The induced cell-matrix composition was harvested then combined with a Fibrin gel and cryopreserved.

In another aspect the disclosure provides a method used to culture cells in the presence of a compound and matrix to increase osteogenesis of the cells.

In another aspect the disclosure provides a method used to culture cells in the presence of a compound and matrix that increases cellular migration onto the matrix.

In another aspect the disclosure provides a method used to culture cells in the presence of a compound to increase osteogenesis of the cells.

In another aspect the disclosure provides a method that was used to prepare osteogenic cell implants for in vivo administration, wherein isolated cells were cultured in the presence of a compound and matrix.

In another aspect the disclosure provides a method that was used to prepare osteogenic cell implants for in vivo administration, wherein isolated cells were cultured in the presence of a compound and matrix and then the cell and matrix composition was combined with a bioadhesive.

In another aspect the disclosure provides a method that was used to prepare osteogenic cell implants for in vivo administration, wherein isolated cells were cultured in the presence of a compound and matrix and then the cell and matrix and compound composition was combined with a bioadhesive.

In another aspect the disclosure provides a method for preparing osteogenic cell implants for in vivo administration, wherein isolated cells are cultured in the presence of a compound and then, in an independent step, the cells are combined with a matrix.

In another aspect the disclosure provides a method for preparing osteogenic cell implants for in vivo administration, wherein isolated cells are cultured in the presence of a compound and then, in an independent step, the cells are combined with a matrix and bioadhesive.

In another aspect the disclosure provides a method that was used for preparing osteogenic cell implants for in vivo administration, wherein isolated cells were cultured in the presence of a compound and matrix and then, in an independent step, the cell and matrix composition was combined with a bioadhesive.

In another aspect the disclosure provides a method that was used for preparing osteogenic cell implants for in vivo administration, wherein isolated cells have been cultured in the presence of a compound and matrix, prior to removal of the compound for in vivo administration.

In another aspect the disclosure provides the above methods wherein the compound is a small molecule capable of modulating the Toll like receptor signaling pathway.

In another aspect the disclosure provides the above methods wherein the compound is a small molecule capable of modulating the Wnt signaling pathway.

In another aspect the disclosure provides the above methods wherein the compound is a small molecule capable of promoting the function and expression of the vitamin D receptor.

In another aspect the disclosure provides the above methods wherein the compound is a small molecule capable of promoting biomarkers of osteogenesis such as alkaline phosphatase functional activity.

In one embodiment the disclosure provides the above methods using compounds of Formula I to VI increased osteogenesis.

In one embodiment the disclosure provides the above methods wherein the matrix was an osteoinductive material.

In one embodiment the disclosure provides the above methods wherein the matrix was an osteoconductive material.

In one embodiment the disclosure provides the above methods wherein the matrix was tricalcium phosphate ceramic granules.

In another aspect the disclosure provides a method that was used for testing compound-matrix combinations by administering compounds to isolated cells in the presence of matrix and determining alkaline phosphatase functional activity.

In another aspect the disclosure provides a method that was used for testing compound-matrix combinations by administering compounds to isolated cells in the presence of matrix and determining mRNA biomarkers of osteogenesis such as Runx2 and BMP2, or Toll-like receptor expression.

In another aspect the disclosure provides a method that was used for adsorbing compounds onto a matrix that represents a non-limiting example of the small-molecule and matrix composition and methods of preparation.

In another aspect the disclosure provides a method that was used for implanting the compositions of the invention into an animal to promote bone formation and/or repair of bone defects, bone fractures, or bone disease.

In another aspect the disclosure provides a method for implanting surgical cages containing the compositions of the invention into an animal to effect spinal fusion.

In another aspect the disclosure provides a method for deriving new cell lines of the osteogenic lineage by culturing cells in the presence of the compound and/or matrix.

In another aspect, the disclosure provides a method that was used for inducing cell differentiation of multipotent, pluripotent, and totipotent cells into the osteogenic cell lineage by culturing cells in the presence of the compound and/or matrix.

In another aspect the disclosure provides a method that was used for culturing cells in the presence of a compound and/or matrix to change the cell-lineage commitment of cells that are pre-committed to another lineage.

In another aspect the disclosure provides a method that was used for ex vivo expansion of animal cells by co-culturing cells in the presence of the compound and/or matrix.

In another aspect the disclosure provides a method that was used for cryopreservation of the compositions of the disclosure.

In another aspect the disclosure provides a process that was used for preparing the compositions of the invention.

In another aspect the disclosure provides a method of using osteogenic compounds of general Formula I to VI to treat osteoporosis, or other diseases of bone in animals.

In another aspect the disclosure provides a method for administering osteogenic compounds of general Formula I to VI to an animal that, in an independent step, receives an implant of matrix at a site where new bone formation, bone fusion, or bone repair is desired.

In another aspect, the disclosure provides a method for attracting cells to the site of an injury or its vicinity by implanting the compositions of the invention in the vicinity of a bone defect, bone fracture, or bone injury in animals.

In another aspect the disclosure provides a method for repairing bone injuries in an animal by increasing cell recruitment to the injured site by implanting a matrix at the site of injury and systemic or local administration of cells in an independent step.

In another aspect the disclosure provides a method for repairing bone injuries in an animal by increasing cell recruitment to the injured site by implanting a matrix at the site of injury and systemic or local administration of a compound of general Formula I to VI in an independent step.

The disclosure also provides articles of manufacture comprising packaging material and a pharmaceutical composition contained within said packaging material, wherein said packaging material comprises a label which indicates that said pharmaceutical composition comprises a compound and matrix according to this disclosure.

The disclosure also provides compositions comprising at least one compound and matrix that may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds of the disclosure may be formulated with use of excipients. Excipients which are contemplated for use in the practice of the disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the compounds are included in the disclosure.

The disclosed compositions may be administered by any suitable means, for example, by surgical implantation to a bone defect, bone fracture, or void volume, by placement in a surgical cage for subsequent implantation, or by injection techniques (e.g., as sterile injectable suspensions in pharmaceutically-acceptable carrier formulation). Alternatively, the compounds and matrices of the invention can be administered separately wherein the matrix is surgically implanted or injected to the site of bone defect, fracture or void volume and the compounds can be administered orally, such as in the form of tablets, capsules, granules or powders; intravenously; by infusion; or by local or systemic injection. In such a form, the compounds of the invention can be administered in pharmaceutically acceptable formulations including liposomal formulations. Alternatively, the compounds of the invention can be administered orally, intravenously, locally by injection or infusion, or by implantation.

In addition to primates, such as humans, a variety of other animals can be treated according to the method of the disclosure. For instance, animals including, but not limited to, cows, sheep, goats, horses, dogs, cats, guinea pigs, rats or other bovine, ovine, equine, canine, feline, rodent or murine species can be treated.

The compositions of the compounds, compound-matrix, or compound-cell-matrix of this embodiment either alone or in combination with other agents, may conveniently be prepared by any of the methods well known in the art of pharmacy, cell therapies, or implantable devices and/or materials. Methods include the step of bringing the active compositions into association with the carrier or bioadhesive that constitutes one or more accessory ingredients. In general, compositions are prepared by uniformly and intimately bringing the active ingredient into association with a liquid carrier or a finely divided solid carrier, or a gel, and then, if necessary, shaping the product into the desired formulation. Pharmaceutical compositions containing the compounds of the invention may also be in a form suitable for oral use, for example, as tablets, troches, lozenges, aqueous or oily suspensions, dispersible powders or granules, emulsions, hard or soft capsules, or syrups or elixirs.

Compositions intended for oral use of the compounds of the disclosure may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

It will be understood, that the specific dose level of the compositions of the disclosure for any particular patient will be varied and will depend upon a variety of factors including the size of the bone defect, injury, or void volume, the location of the injury, and the identity or characteristics of surgical devices such as surgical cages for spinal fusion procedures. Primarily, the dose levels for a particular indication will be at the surgeon's discretion and guided by the techniques, instruments, and methods standard in the medical field.

EXAMPLES

Conventions and Techniques of the Field

Cell Differentiation in Osteogenesis. A common method for inducing differentiation of stem cells into cells of the bone lineage is to culture cells in osteogenic media. Osteogenic media consists of beta-glycerol phosphate, ascorbic acid-2-phosphate, and dexamethasone, although there are many variations on osteogenic media that use combinations of these agents or individual components such that a standard formulation of the osteogenic media is difficult to define. Typically, cells are cultured in osteogenic media for 7-21 days during which time cells, such as human mesenchymal stem cells, differentiate into cells of the bone lineage. A second method for inducing differentiation of stem cells into cells of the bone lineage is to culture cells in either normal media or osteogenic media, but with addition of bone morphogenetic protein-2 (BMP-2) that is a potent cell differentiation factor. Using BMP-2 at typical doses (25-300 ng/mL) human MSCs differentiate into cells of the bone lineage.

Characterization of Cell Differentiation during Osteogenesis. Cells, such as human mesenchymal stem cells, that differentiate into the bone lineage are characterized by multiple methods. One of the primary methods of observing osteogenesis in cell culture is by monitoring alkaline phosphatase that is an enzyme that hydrolyzes inorganic pyrophosphates to phosphates and promotes the formation of hydroxyapatite and deposited mineral matrix of the bone tissue. Protein levels of alkaline phosphatase (ALP) are determined by immunohistochemical staining, Western Blot, and ELISA. ALP functional activity determination is based on treating cell lysates with a pro-chromogenic or pro-fluorescent substrate of the enzyme and quantifying enzymatic activity as readout of fluorescent signal or UV/Vis absorbance/transmittance measurements. Generally, protein levels and the associated enzymatic activity of alkaline phosphatase increase as cells undergo osteogenesis, although the levels stabilize over time. In addition, there are also changes in mRNA expression that function as biomarkers for osteogenesis and signal a change in cell differentiation state. For example, increased mRNA expression of Runx2, ALP, Collagen I, Osteocalcin, Bone Morphogenetic Protein 2, Bone Sialoprotein, Osteopontin, and S100A4 are determined by the techniques of qPCR.

The compositions and methods of the present invention were used to promote bone formation and/or bone repair in animals through an unexpectedly robust way in which cells are induced to the osteogenic lineage by the effect of compounds of Formula I to VI acting on cells in the presence of a matrix. The compositions of the invention included (but are not limited to) either compounds of Formula I to VI and matrix, or compounds of Formula I to VI and matrix and isolated cells capable of differentiating to bone cells. Such compositions are implantable and are used to improve bone formation and repair in a variety of applications where natural bone repair processes are inefficient, or for spinal fusion procedures. The methods of the present invention likewise enabled (but are not limited to) the preparation of these compositions as well as their use to improve bone formation and bone repair in animals using surgical techniques or injectable techniques. The combination of pre-treated cells and/or matrix also induced unexpected cellular function including osteogenesis and increased migration.

One of the distinctions of the small molecule-treated cells and matrix was that these agents induce osteogenesis even in the absence of osteogenic media, osteogenic supplements, or BMP-2. Furthermore, the application of compounds of Formula I to VI in the presence of matrix induced osteogenesis in cells in excess of either compound or matrix used independently. Further conventions of the field pertaining to this invention are described below:

The compositions of the present invention were prepared ex vivo (i.e., using in vitro methods) for application to in vivo bone formation and repair. Thus, the induced osteogenesis in isolated cells of the compositions was detected by conventional methods that have been employed in the detection of osteogenesis (in vitro or in vivo), such as detection of expression of osteoblast-specific proteins, detection of bone tissue mineralization, and altered gene expression in cells. The osteoblast-specific proteins included alkaline phosphatase, collagen I, and osteocalcin.

1. Detection of ALP activity in vitro. ALP has been widely accepted as a molecular marker for differentiated osteoblasts. When bone progenitor cells differentiate into osteoblasts, the expression of ALP increases so that osteoblasts hydrolyze inorganic pyrophosphates to phosphates and promote the formation of hydroxyapatite or mineralized protein deposition in bone matrix. In another scenario, when cells that belong to a different lineage transdifferentiate into osteoblasts, expression of ALP is a molecular marker for osteogenesis. The activity of ALP in differentiated osteoblasts was analyzed in vitro using para-nitrophenolphosphate (pNPP) as the substrate. After incubating the cells on culture dishes with added pNPP for 10-30 minutes, cells were lysed by adding lysis buffer and analyzed by a colorimetric (or UV absorbance/transmittance) readout for ALP functional activity using a plate reader.

2. Detection of osteogenic markers by qPCR. In addition to changes in protein levels and function such as ALP activity, changes in osteoblast-specific genes expression occur including increased levels of collagen I, osteocalcin, Runx2, BMP-2, Osterix, or other genes. Altered gene expression was detected by analyzing mRNA levels by qPCR. In general, the cells of the compositions that are present with compound and/or matrix were lysed and their total RNA was extracted. After converting their mRNA into cDNA, the level of cDNA was analyzed by qPCR.

3. Detection of calcium deposition by Alizarin Red Staining. When osteoblasts mature, hard tissue of bone contains a large amount of hydroxyapatite and/or mineralized protein deposits. The calcium component of a mineralized deposit was analyzed by Alizarin Red Staining (ARS). ARS specifically stains calcium in the tissue so that the red color is an indicator of accumulated deposited calcium. Isolated cells capable of differentiating into bone cells in the presence of compound of Formula I to VI and/or matrix can therefore be characterized for calcium deposition using the techniques of the field.

4. Bone repair in animal models. The present invention was applied in animal models of bone injury and repair. Animal models include mouse, rat, rabbit, goat, sheep, dog, non-human primates, among others. In mouse and rat, the conventional models include muscle pouch implantation models, subcutaneous implantation models, or calvarial injury or mandible injury. The intramuscular implantation model in mice was used to assess the osteoinductive and osteogenic properties of the implant because the implant is placed outside of the normal bone environment that is recognized to promote bone formation. Therefore, the intramuscular implant model tested the intrinsic ability of the implant to form bone and its progenitor tissue in vivo and is less likely to be biased by implantation in a natural bone environment. Also, the availability of immunodeficient rodent strains permitted the investigation of human cells without resorting to co-administration of immunosuppressive drugs. In the present invention, implantable compositions that used different combinations of cells, matrix, and compounds were applied to in vivo bone formation, such as implanting compositions of isolated, cultured cells treated in the presence of compound(s) and matrix. The present invention also describes i) implanting compositions of isolated, cultured cells treated in the presence of compound(s) and later combined with an implantable matrix, ii) implanting compositions of matrix that has been coated or adsorbed with compound(s), iii) administering compounds alone, or iv) implanting the matrix in an animal and administering the compound in a separate step. Most importantly, the composition of isolated cells capable of differentiating into bone cells in the presence of compound and matrix gave robust osteogenesis not predicted by the use of either compound or matrix used separately. The routes of administration were primarily by surgical implantation or injection of the compositions of the invention that are optionally combined with a bioadhesive, a cell carrier, osteoconductive scaffold, or surgical device. Alternatively, the compounds of Formula I to VI are administered to an animal orally, intravenously, by ointment, or by local injection or infusion as a method to promote bone formation in an animal. Furthermore, the administration of compound by oral, intravenous, or injection/infusion are coupled with surgical implantation of the matrix and/or cells, such that the effects of compound and matrix on osteogenesis are re-constituted in vivo using different routes of administration of each entity. As such, many of the conventions of pharmaceutical formulation and administration also apply to this invention as understood by one skilled in the art. Assessment of the efficiency of osteogenesis in animal models was done by assessing new bone formation, bone repair and bone union histomorphometrically by analyzing the results from histological assessment of the implanted material periodically.

5. Measurement of bone density. Bone density is measured by bone density detectors that are widely available on the market. After administration of the present invention to the patients, bone density is periodically measured to monitor the progress of bone repair. In general, the bone density detector is an x-ray imaging system that can assess the whole-body bone image and analyze the changes of bone density in images.

6. Medical application. The present invention is used to treat human bone injury and promote bone repair, as well as to promote spinal fusion by implanting surgical cages using standard techniques in the field wherein the surgical cages contain the compositions of the invention. Human bone diseases include osteoporosis, rickets, osteomalacia, McCune-Albright syndrome, Paget's disease, cervical disc degeneration, lumbar degenerative disc disease, degenerative coliosis, and degenerative spondylolithesis. Bone diseases are often a complicating factor in repairing bone fractures or injuries, since the pre-existing bone disease compromises the fidelity of the bone repair process or therapeutic interventions. In some cases, a bone disorder may be related to cancer, such as osteosarcoma or other cancers that has disseminated to bone. Some bone injury is from a fracture or bone break resulting from osteogenesis imperfecta, cranial injury, or trauma. Similar to animal models, the administration of the present invention occurs through multiple formulations and through multiple routes, including i) implanting compositions of isolated cells that were cultured in the presence of compound(s) and matrix, ii) implanting compositions of isolated cell that were cultured in the presence of compound(s) and later combined with an implantable matrix, iii) implanting compositions of matrix that has been coated or adsorbed with compound(s), iv) administering compounds alone, or v) implanting the matrix in an animal and administering the compound in a separate step. Most importantly, the composition of isolated cells capable of differentiating into bone cells in the presence of compound and matrix gives robust osteogenesis not predicted by the use of either compound or matrix used separately. The routes of administration are primarily by surgical implantation or injection of the compositions of the invention that are optionally combined with a bioadhesive, a cell carrier, osteoconductive scaffold, or surgical device. Alternatively, the compounds of Formula I to VI are administered to an animal orally, intravenously, by ointment, or by local injection or infusion as a method to promote bone formation in an animal. Furthermore, the administration of compound by oral, intravenous, or injection/infusion is coupled with surgical implantation of the matrix and/or cells, such that the effects of compound and matrix on osteogenesis are re-constituted in vivo using different routes of administration of each entity. As such, many of the conventions of pharmaceutical formulation and administration also apply to this invention as understood by one skilled in the art. A preferred embodiment of the present invention involved isolated cells capable of differentiating to bone that were cultured under conditions of 1%-30% of serum at a cell density of 100-500,000 per $cm^2$, in the presence of compound of Formula I to VI (0.5-500 nM) and matrix (5 mg/mL-100 mg/mL) for 8 days or at the conclusion of a suitable cell culture time. After 1 to 25 days of culturing, the induced cell-matrix composition was surgically implanted at the desired site in vivo, or is added to a surgical cage for use in a spinal fusion procedure using the techniques standard in the field. Assessment of the efficiency of osteogenesis was done by assessing new bone formation, bone repair and bone union/fusion radiographically and by patient outcome criterion such as the Oswestry Disability Index as a non-limiting example.

The embodiments of the disclosure may be further illustrated by the following non-limiting examples:

Example 1

General Synthetic Procedures for Obtaining Compounds of Formula II and their Characterization The structures of general Formula II:

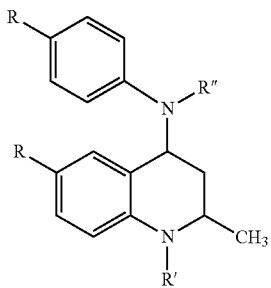

II were synthesized according to the following scheme.

Scheme 1. General procedure for preparing Formula II compounds.

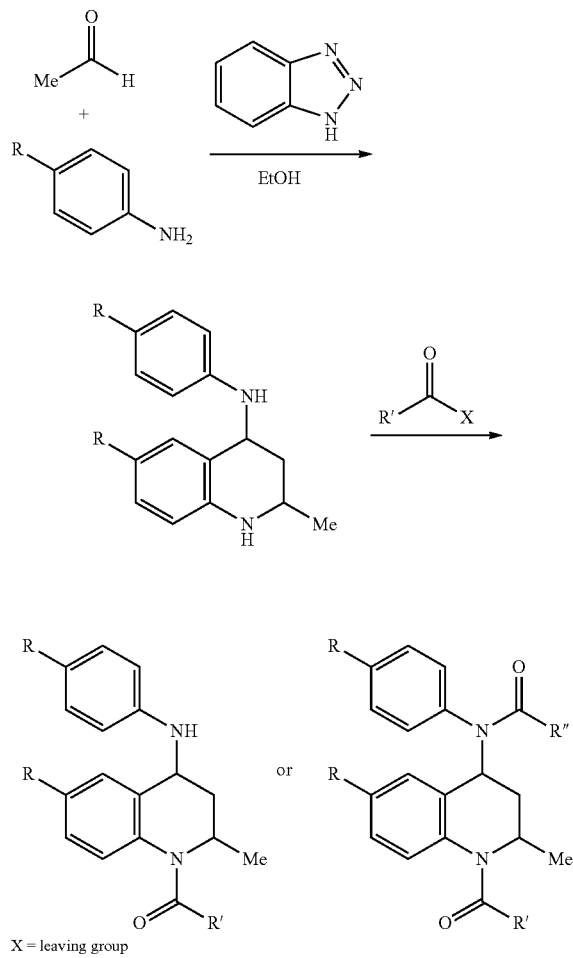

X = leaving group

General procedure for synthesis of both 2,4-cis and 2,4-trans stereoisomers of 2-methyl-N-aryl-1,2,3,4-tetrahydroquinolin-4-amines from substituted anilines and acetaldehyde (Scheme 1). 1-H-benzotriazole (0.4 equiv) was added to a solution of acetaldehyde (2 equiv, 1M) and aniline (2.0 equiv, 1M) in ethanol at 21° C., stirred in a sealed flask, and after 3-7 days, concentrated. The crude product was purified by silica gel column chromatography (diethyl ether in hexanes) to yield cis-2-methyl-N-aryl-1,2,3,4-tetrahydroquinolin-4-amine and trans-2-methyl-N-aryl-1,2,3,4-tetrahydroquinolin-4-amine and mixed fractions of both stereoisomers. In some cases, tetrahydroquinolines are recrystalized from hot hexanes/diethyl ether (~2/1).

General procedure for synthesis of cis-1-acetyl-2-methyl-N-aryl-1,2,3,4-tetrahydroquinolin-4-amine (Scheme 1). Acetic anhydride (1.8 equiv.) and 4-(N,N-dimethylamino)pyridine (0.15 equiv.) were added to a solution of cis-2-methyl-N-aryl-1,2,3,4-tetrahydroquinolin-4-amine (1.0 equiv., 0.1 M) and triethylamine (3.3 equiv.) in $CHCl_3$ at 21° C. After 24 hours, the reaction was diluted with $CH_2Cl_2$, washed with sat. $NaHCO_{3(aq)}$ and sat. $NaCl_{(aq)}$, dried ($Na_2SO_4$), filtered, concentrated and purified by silica gel flash column chromatography (hexanes/ethyl acetate) to provide cis-1-acetyl-2-methyl-N-aryl-1,2,3,4-tetrahydroquinolin-4-amines.

General procedure for synthesis of trans-1-acetyl-2-methyl-N-aryl-1,2,3,4-tetrahydroquinolin-4-amine and trans-1-acetyl-2-methyl-N-aryl-N-acetyl-1,2,3,4-tetrahydroquinolin-4-amine (reaction 2 in Scheme 1). Acetic anhydride (2.6 equiv.) was added to a solution of trans-2-methyl-N-aryl-1,2,3,4-tetrahydroquinolin-4-amine (1.0 equiv., 0.09 M) and triethylamine (3.3 equiv.) in $CHCl_3$ at 21° C. After 1-2 hours, the reaction mixture was diluted with $CH_2Cl_2$, washed with sat. $NaHCO_{3(aq)}$ and sat. $NaCl_{(aq)}$, dried ($Na_2SO_4$), filtered, concentrated and purified by silica gel flash column chromatography (hexanes/ethyl acetate) to provide the trans-1-acetyl-2-methyl-N-aryl-1,2,3,4-tetrahydroquinolin-4-amine and trans-1-acetyl-2-methyl-N-aryl-N-acetyl-1,2,3,4-tetrahydroquinolin-4-amine.

Alternative procedure for synthesis of 1-benzoyl-2-methyl-N-aryl-1,2,3,4-tetrahydroquinolin-4-amine (reaction 2 in Scheme 1). Benzoyl chloride (1.3 equiv.) was added to a solution of cis or trans 2-methyl-N-aryl-1,2,3,4-tetrahydroquinolin-4-amine (1.0 equiv., 0.09 M) and triethylamine (3.3 equiv.) in $CH_2Cl_2$ at 21° C. Following 1-16 hours, the reaction was worked-up as above to provide the title compound.

Examples of compounds of Formula II synthesized are given in Table 1 and comprise all possible stereoisomers of the compounds. Other compounds encompassed by Formula I and Formula II are prepared by appropriate adapatations of Scheme 1 and the synthetic methods described herein. Characterization data for compounds of general Formula II as shown in Scheme 1 are the following:

cis-1-acetyl-2,6-dimethyl-N-(p-methylphenyl)-1,2,3,4-tetrahydroquinolin-4-amine, Compound 1.

ESI/MS m/z=331.2 ($MNa^+$); Rf=0.44 (6/4 hexanes/EtOAc); $^1H$ NMR (300 MHz, $CDCl_3$): δ 7.27 (b, 1H), 7.11-7.01 (m, 4H), 6.59 (m, 2H), 4.90 (b, 1H), 4.17 (dd, J=11.5, 4.1 Hz, 1H), 2.65 (ddd, J=12.4, 8.8, 4.4 Hz, 1H), 2.34 (s, 3H), 2.28 (s, 3H), 2.20 (s, 3H), 1.24 (overlapping with neighboring signal, 1H), 1.17 (d, J=6.4 Hz, 3H) ppm.

TABLE 1

Compounds of General Formula II.

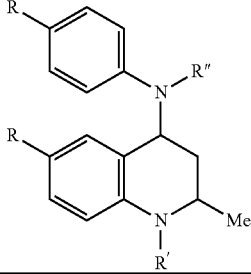

| Compound | R | R' | R'' | Stereochemistry* |
|---|---|---|---|---|
| 1 | CH₃ | (O)CCH₃ | H | cis |
| 5 | CH₃ | H | H | cis |
| 6 | CH₃ | H | H | trans |
| 7 | H | H | H | cis |
| 8 | H | H | H | trans |
| 9 | F | H | H | cis |
| 10 | F | H | H | trans |
| 11 | —OCH₃ | H | H | cis |
| 12 | —OCH₃ | H | H | trans |
| 13 | CH₃ | —(O)CCH₃ | H | trans |
| 14 | CH₃ | —(O)CCH(CH₃)₂ | H | cis |
| 15 | CH₃ | —(O)CCH(CH₃)₂ | H | trans |
| 16 | CH₃ | —(O)C-cyclopropyl | H | cis |
| 17 | CH₃ | —(O)C-cyclopropyl | H | trans |
| 18 | CH₃ | —(O)CPh | H | cis |
| 19 | CH₃ | —(O)CPh | H | trans |
| 20 | H | —(O)CCH₃ | H | cis |
| 21 | F | —(O)CCH₃ | H | cis |
| 22 | F | —(O)CCH₃ | H | trans |
| 23 | F | —(O)CPh | H | cis |
| 24 | F | —(O)CPh | H | trans |
| 25 | F | —(O)C(Ph-4-OMe) | H | cis |
| 26 | F | —(O)C(Ph-4-OMe) | H | trans |
| 27 | CH₃ | —(O)CCH₃ | —(O)CCH₃ | trans |
| 28 | CH₃ | —(O)CPh | —(O)CPh | trans |
| 29 | F | —(O)CPh | —(O)CPh | trans |
| 30 | F | —(O)C(Ph-4-OMe) | —(O)C(Ph-4-OMe) | trans |

*Stereochemistry designates relative configuration of the 2- and 4- substituents about the tetrahydroquinoline ring cis-2,6-dimethyl-N-(p-methylphenyl)-1,2,3,4-tetrahydroquinolin-4-amine, Compound 5

ESI/MS m/z=267.2 (MH⁺); Rf=0.35 (10% diethyl ether/hexanes); ¹H NMR (300 MHz, CDCl₃): δ 7.08-7.06 (m, 3H), 6.94 (dd, J=8.0, 1.9 Hz, 1H), 6.63 (d, J=8.5 Hz, 2H), 6.53 (d, J=8.2 Hz, 1H), 4.51 (b, 1H), 3.83 (b, 2H), 3.46 (m, 1H), 2.31 (s, 3H), 2.25-2.17 (m, 4H), 1.58 (ddd, J=12.9, 11.3, 3.9 Hz, 1H), 1.26 (d, J=6.3 Hz, 3H) ppm.

trans-2,6-dimethyl-N-(p-methylphenyl)-1,2,3,4-tetrahydroquinolin-4-amine, Compound 6

ESI/MS m/z=267.2 (MH⁺); Rf=0.26 (10% diethyl ether/hexanes); ¹H NMR (300 MHz, CDCl₃): δ 7.26 (s, 1H), 7.03 (m, 2H), 6.88 (dd, J=8.0, 2.0 Hz, 1H), 6.63 (m, 2H), 6.46 (d, J=7.9 Hz, 1H), 4.78 (dd, J=11.3, 5.5 Hz, 1H), 3.67 (b, 2H), 3.59 (m, 1H), 2.41 (ddd, J=12.7, 5.5, 2.5 Hz, 1H), 2.30 (s, 3H), 2.24 (s, 3H), 1.49 (app q, J=11.3, 1H), 1.23 (d, J=6.1 Hz, 3H) ppm.

cis-2-methyl-N-phenyl-1,2,3,4-tetrahydroquinolin-4-amine, Compound 7

ESI/MS m/z=239.2 (MH⁺); Rf=0.35 (20% diethyl ether/hexanes); ¹H NMR (300 MHz, CDCl₃): δ 7.26-7.20 (m, 3H), 7.10 (m, 1H), 6.77-6.67 (m, 4H), 6.58 (dd, J=8.0, 1.1 Hz, 1H), 4.58 (dd, J=3.8, 2.5 Hz, 1H), 3.94 (b, 2H), 3.48 (m, 1H), 2.23 (dt, J=13.2, 2.5 Hz, 1H), 1.60 (ddd, J=12.9, 11.3, 3.8 Hz, 1H), 1.26 (d, J=6.3 Hz, 3H) ppm.

trans-2-methyl-N-phenyl-1,2,3,4-tetrahydroquinolin-4-amine, Compound 8

ESI/MS m/z=261.1 (MNa⁺); Rf=0.26 (20% diethyl ether/hexanes); ¹H NMR (300 MHz, CDCl₃): δ 7.40 (dt, J=7.7, 1.1 Hz, 1H), 7.26-7.19 (m, 2H), 7.06 (m, 1H), 6.77-6.66 (m, 4H), 6.53 (dd, J=8.0, 1.1 Hz, 1H), 4.85 (dd, J=11.5, 5.5 Hz, 1H), 3.81 (b, 2H), 3.65 (m, 1H), 2.38 (ddd, J=12.7, 5.5, 2.5 Hz, 1H), 1.53 (app q, J=11.3 Hz, 1H), 1.26 (d, J=6.3 Hz, 3H) ppm.

cis-2-methyl-6-fluoro-N-(p-fluorophenyl)-1,2,3,4-tetrahydroquinolin-4-amine, Compound 9

Rf=0.53 (40% diethyl ether/hexanes); ¹H NMR (300 MHz, CDCl₃): δ 6.93 (m, 3H), 6.83 (td, J=8.5, 2.7 Hz, 1H), 6.60 (m, 2H), 6.52 (dd, J=8.8, 4.7 Hz, 1H), 4.45 (dd, J=4.4, 3.0 Hz, 1H), 3.79 (b, 2H), 3.41 (m, 1H), 2.14 (dt, J=13.5, 2.2 Hz, 1H), 1.57 (ddd, J=13.2, 11.3, 4.1 Hz, 1H), 1.59 (ddd, J=13.0, 11.6, 3.9 Hz, 1H), 1.25 (d, J=6.1 Hz, 3H) ppm.

trans-2-methyl-6-fluoro-N-(p-fluorophenyl)-1,2,3,4-tetrahydroquinolin-4-amine, Compound 10

Rf=0.47 (40% diethyl ether/hexanes); ¹H NMR (300 MHz, CDCl₃): δ 7.13 (ddd, J=9.6, 3.8, 0.8 Hz, 1H), 6.92 (m, 2H), 6.77 (tdd, J=8.8, 3.0, 0.8 Hz, 1H), 6.62 (m, 2H), 6.45 (dd, J=8.8, 4.6 Hz, 1H), 4.71 (dd, J=11.9, 5.2 Hz, 1H), 3.7-3.4 (b, 1H), 3.58 (m, 1H), 2.34 (ddd, J=12.6, 5.5, 2.2 Hz, 1H), 1.49 (app q, J=11.6, 1H), 1.24 (d, J=6.3 Hz, 3H) ppm.

cis-2-methyl-6-methoxy-N-(p-methoxyphenyl)-1,2,3,4-tetrahydroquinolin-4-amine, Compound 11

Rf=0.30 (40% diethyl ether/hexanes); ¹H NMR (300 MHz, CDCl₃): δ 6.85-6.78 (m, 4H), 6.69-6.65 (m, 2H), 6.50 (m, 1H), 4.74 (m, 1H), 3.78 (s, 3H), 3.72 (s, 3H), 3.50 (q, 1H), 2.38 (m, 1H), 1.48 (m, 1H), 1.23 (d, J=6.1 Hz, 3H) ppm.

trans-2-methyl-6-methoxy-N-(p-methoxyphenyl)-1,2,3,4-tetrahydroquinolin-4-amine, Compound 12

Rf=0.35 (40% diethyl ether/hexanes); ¹H NMR (300 MHz, CDCl₃): δ 6.86-6.81 (m, 2H), 6.80 (m, 1H), 6.73 (m, 1H), 6.68-6.63 (m, 2H), 6.55 (m, 1H), 4.46 (dd, J=1.9 Hz, 1H), 3.79 (s, 3H), 3.73 (s, 3H), 3.42 (m, 1H), 2.16 (dt, J=12.9, 2.2 Hz, 1H), 1.57 (m, 1H), 1.23 (d, J=6.1 Hz, 3H) ppm.

trans-1-acetyl-2,6-dimethyl-N-(p-methylphenyl)-1,2,3,4-tetrahydroquinolin-4-amine, Compound 13

ESI/MS m/z=331.0 (MNa⁺); Rf=0.24 (7/3 hexanes/EtOAc); ¹H NMR (300 MHz, CDCl₃): δ 7.20 (b, 1H), 7.08 (b, 1H), 6.99 (dd, J=8.5, 0.6 Hz, 1H), 6.58 (m, 2H), 4.90 (b, 1H), 4.53 (app t, J=4.7 Hz, 1H), 2.52 (ddd, J=13.2, 7.2, 4.7 Hz, 1H), 2.36 (s, 3H), 2.25 (s, 3H), 2.18 (s, 3H), 1.74 (m, 1H), 1.20 (d, J=6.3 Hz, 3H) ppm.

cis-1-(2-propylcarbonyl)-2,6-dimethyl-4-(4-methylphenylamino)-1,2,3,4-tetrahydroquinoline, Compound 14

ESI/MS m/z=358.9 (MNa⁺); Rf=0.55 (7/3 hexanes/EtOAc); ¹H NMR (300 MHz, CDCl₃): δ 7.17 (s, 1H), 7.10 (m, 1H), 7.02 (m, 3H), 6.56 (m, 2H), 4.92 (b, 1H), 4.08 (dd, J=11.3, 4.4 Hz, 1H), 3.10 (app septet, J=6.9 Hz, 1H), 2.66 (ddd, J=12.1, 8.8, 4.4 Hz, 1H), 2.34 (s, 3H), 2.28 (s, 3H), 1.26 (m, 4H), 1.12 (d, J=6.6 Hz, 3H), 0.9 (d, J=6.6 Hz, 3H) ppm.

trans-1-(2-propylcarbonyl)-2,6-dimethyl-4-(4-methylphenylamino)-1,2,3,4-tetrahydroquinoline, Compound 15

ESI/MS m/z=359.0 (MNa⁺); Rf=0.54 (7/3 hexanes/EtOAc); ¹H NMR (300 MHz, CDCl₃): δ 7.22 (b, 1H), 7.08 (m, 1H), 6.99 (m, 3H), 6.56 (d, J=8.5 Hz, 2H), 4.87 (b, 1H), 4.51 (app t, J=4.4 Hz, 1H), 3.06 (app septet, J=6.9 Hz, 1H), 2.55 (ddd, J=13.2, 7.4, 4.1 Hz, 1H), 2.37 (s, 3H), 2.25 (s, 3H), 1.68 (b, 1H), 1.26 (d, J=6.9 Hz, 3H), 1.18 (d, J=6.6 Hz, 3H), 1.01 (d, J=6.6 Hz, 3H) ppm.

cis-1-(cyclopropylcarbonyl)-2,6-dimethyl-4-(4-methylphenylamino)-1,2,3,4-tetrahydroquinoline, Compound 16

ESI/MS m/z=334.5 (MH⁺); Rf=0.46 (7/3 hexanes/ethyl acetate); ¹H NMR (300 MHz, CDCl₃): δ 7.25 (d, J=3.5 Hz, 1H), 7.18 (s, 1H), 7.09 (dd, J=7.9, 1.9 Hz, 1H), 7.02 (m, 2H), 6.61 (m, 2H), 4.82 (m, 1H), 4.24 (m, 1H), 3.68 (b, 1H), 2.67 (ddd, J=13.0, 8.6, 4.2 Hz, 1H), 2.34 (s, 3H), 2.29 (s, 3H), 1.88 (m, 1H), 1.27 (m, 2H), 1.16 (d, J=6.3 Hz, 3H), 1.03 (m, 1H), 0.88 (m, 1H), 0.70 (m, 1H) ppm.

trans-1-(cyclopropylcarbonyl)-2,6-dimethyl-4-(4-methylphenylamino)-1,2,3,4-tetrahydroquinoline, Compound 17

ESI/MS m/z=334.5 (MH⁺); Rf=0.65 (7/3 hexanes/ethyl acetate); ¹H NMR (300 MHz, CDCl₃): δ 7.22 (m, 2H), 7.08 (dd, J=8.0, 1.4 Hz, 1H), 6.99 (d, J=7.7 Hz, 2H), 6.59 (m, 2H), 4.89 (app sextet, J=6.8 Hz, 1H), 4.58 (t, J=4.4 Hz, 1H), 2.51 (m, 1H), 2.35 (s, 3H), 2.25 (s, 3H), 1.87 (m, 1H), 1.77 (m, 1H), 1.20 (d, J=6.6 Hz, 3H), 1.03 (m, 1H), 0.88 (m, 2H), 0.68 (m, 1H) ppm.

cis-1-benzoyl-2,6-dimethyl-N-(p-methylphenyl)-1,2,3,4-tetrahydroquinolin-4-amine, Compound 18

ESI/MS m/z=393.0 (MNa⁺); Rf=0.29 (8/2 hexanes/EtOAc); ¹H NMR (300 MHz, CDCl₃): δ 7.35-7.27 (m, 3H), 7.27-7.19 (m, 4H), 7.06 (m, 2H), 6.73 (m, 1H), 6.67 (b, 1H), 6.40 (m, 1H), 4.90 (m, 1H), 4.42 (m, 1H), 2.81 (m, 1H), 2.31 (s, 3H), 2.25 (s, 3H), 1.39 (m, 1H), 1.29 (d, J=6.0 Hz, 3H) ppm.

trans-1-benzoyl-2,6-dimethyl-N-(p-methylphenyl)-1,2,3,4-tetrahydroquinolin-4-amine, Compound 19

ESI/MS m/z=393.0 (MNa⁺); Rf=0.35 (8/2 hexanes/EtOAc); ¹H NMR (300 MHz, CDCl₃): δ 7.35-7.27 (m, 4H), 7.27-7.19 (m, 4H), 7.03 (m, 2H), 6.75 (m, 1H), 6.70 (b, 1H), 4.90 (m, 1H), 4.69 (m, 1H), 2.49 (m, 1H), 2.34 (s, 3H), 2.28 (s, 6H), 1.33 (d, J=6.0 Hz, 3H) ppm.

cis-1-acetyl-4-(phenylamino)-1,2,3,4-tetrahydroquinoline, Compound 20

ESI/MS m/z=281.9 (MH⁺); Rf=0.27 (7/3 hexanes/EtOAc); ¹H NMR (300 MHz, CDCl₃): δ 7.30 (m, 2H), 7.22-7.12 (m, 4H), 6.75 (app tt, J=7.4, 1.1 Hz, 1H), 6.64 (m, 2H), 4.91 (m, 1H), 4.22 (dd, J=11.9, 3.6 Hz, 1H), 3.88 (b, 1H), 2.66 (ddd, J=12.7, 8.5, 4.1 Hz, 1H), 2.20 (s, 3H), 1.30 (m, 1H), 1.17 (d, J=6.4 Hz, 3H) ppm.

cis-1-acetyl-2-methyl-6-fluoro-N-(p-fluorophenyl)-1,2,3,4-tetrahydroquinolin-4-amine, Compound 21

Rf=0.30 (6/4 hexanes/EtOAc); ¹H NMR (300 MHz, CDCl₃): δ 7.11 (b, 1H), 7.02 (m, 2H), 6.92 (m, 2H), 6.56 (m, 2H), 4.93 (b, 1H), 4.10 (dd, J=12.4, 3.8 Hz, 1H), 2.67 (ddd, J=12.4, 8.8, 4.4 Hz, 1H), 2.19 (s, 3H), 1.25 (m, 1H), 1.17 (d, J=6.4 Hz, 3H) ppm.

trans-1-acetyl-2-methyl-6-fluoro-N-(p-fluorophenyl)-1,2,3,4-tetrahydroquinolin-4-amine, Compound 22

Rf=0.24 (75/25 hexanes/EtOAc); ¹H NMR (300 MHz, CDCl₃): δ 7.19 (b, 1H), 7.10 (dd, J=8.5, 3.0 Hz, 1H), 6.98 (td, J=8.6, 3.1 Hz, 1H), 6.87 (m, 2H), 6.56 (m, 2H), 4.89 (b, 1H), 4.49 (t, J=4.7 Hz, 1H), 3.90 (b, 1H), 2.47 (m, 1H), 2.15 (s, 3H), 1.79 (m, 1H), 1.19 (d, J=6.6 Hz, 3H) ppm.

cis-1-benzoyl-2-methyl-6-fluoro-N-(p-fluorophenyl)-1,2,3,4-tetrahydroquinolin-4-amine, Compound 23

Rf=0.58 (6/4 hexanes/EtOAc); ¹H NMR (300 MHz, CDCl₃): δ 7.38-7.24 (m, 5H), 7.05 (ddd, J=8.8, 2.7, 1.8 Hz, 1H), 6.97 (m, 2H), 6.64 (m, 3H), 6.52 (dd, J=8.3, 4.7 Hz, 1H), 4.93 (app qd, J=6.4, 2.0 Hz, 1H), 4.37 (dd, J=11.6, 4.2 Hz, 1H), 3.79 (b, 1H), 2.83 (ddd, J=12.1, 8.5, 4.4 Hz, 1H), 1.25 (td, J=12.1, 8.2 Hz, 1H), 1.29 (d, J=6.3 Hz, 3H) ppm.

trans-1-benzoyl-2-methyl-6-fluoro-N-(p-fluorophenyl)-1,2,3,4-tetrahydroquinolin-4-amine, Compound 24

Rf=0.42 (75/25 hexanes/EtOAc); ¹H NMR (300 MHz, CDCl₃): δ 7.38-7.24 (m, 5H), 7.17 (m, 1H), 6.93 (m, 2H), 6.71 (m, 2H), 6.66 (m, 2H), 4.87 (m, 1H), 4.63 (app t, J=5.0 Hz, 1H), 2.45 (m, 1H), 2.00 (dt, J=13.3, 5.5 Hz, 1H), 1.36 (d, J=6.6 Hz, 3H) ppm.

cis-1-(p-methoxybenzoyl)-2-methyl-6-fluoro-N-(p-fluorophenyl)-1,2,3,4-tetrahydroquinolin-4-amine, Compound 25

ESI/MS m/z=430.8 (MNa⁺); Rf=0.17 (75/25 hexanes/EtOAc); ¹H NMR (300 MHz, CDCl₃): δ 7.22 (m, 2H), 7.06 (d, J=8.5 Hz, 2H), 6.97 (m, 2H), 6.77 (m, 2H), 6.71-6.52 (m, 4H), 4.89 (m, 1H), 4.36 (dd, J=11.8, 4.1 Hz, 1H), 3.82 (s, 3H), 2.83 (ddd, J=12.1, 8.8, 4.4 Hz, 1H), 1.39 (td, J=12.4, 8.8 Hz, 1H), 1.28 (d, J=6.3 Hz, 3H) ppm.

trans-1-(p-methoxybenzoyl)-2-methyl-6-fluoro-N-(p-fluorophenyl)-1,2,3,4-tetrahydroquinolin-4-amine, Compound 26

Rf=0.16 (1/5/94 acetic acid/acetonitrile/chloroform); ¹H NMR (300 MHz, CDCl₃): δ 7.24 (s, 1H), 7.15 (dd, J=8.5, 2.7

Hz, 1H), 6.92 (m, 2H), 6.74-6.64 (m, 7H), 4.87 (m, 1H), 4.62 (app t, J=5.2 Hz, 1H), 3.79 (s, 3H), 2.48 (dt, J=13.2, 6.6 Hz, 1H), 1.96 (dt, J=13.8, 5.5 Hz, 1H), 1.34 (d, J=6.4 Hz, 3H) ppm.

trans-1-acetyl-2,6-dimethyl-N-(p-methylphenyl)-N-acetyl-1,2,3,4-tetrahydroquinolin-4-amine, Compound 27

Rf=0.19 (6/4 hexanes/EtOAc); $^1$H NMR (300 MHz, CDCl$_3$): δ 7.28 (b, 1H), 7.02 (m, 3H), 6.81-6.70 (b, 2H), 6.16 (t, J=4.9 Hz, 1H), 4.93 (b, 1H), 2.37 (s, 3H), 2.28 (s, 3H), 2.21 (m, 1H), 1.85 (s, 3H), 1.69 (s, 3H), 1.07 (d, J=6.9 Hz, 3H) ppm.

trans-1-benzoyl-2,6-dimethyl-N-(p-methylphenyl)-N-benzoyl-1,2,3,4-tetrahydroquinolin-4-amine, Compound 28

Rf=0.15 (8/2 hexanes/EtOAc); $^1$H NMR (300 MHz, CDCl$_3$): δ 7.45 (s, 1H), 7.38-7.29 (m, 3H), 7.26-7.16 (m, 5H), 7.09 (m, 2H), 6.98-6.78 (AB q, J=8.2 Hz, 2H), 6.68 (d, J=8.6 Hz, 1H), 6.42 (m, 1H), 6.36 (m, 1H), 5.15 (b, 1H), 2.33 (s, 3H), 2.30-2.16 (m, 5H), 1.30 (d, J=6.9 Hz, 3H) ppm.

trans-1-benzoyl-2-methyl-6-fluoro-N-(p-fluorophenyl)-N-benzoyl-1,2,3,4-tetrahydroquinolin-4-amine, Compound 29

Rf=0.31 (75/25 hexanes/EtOAc); $^1$H NMR (300 MHz, CDCl$_3$): δ 7.39-7.33 (m, 4H), 7.26-7.18 (m, 4H), 7.11 (m, 2H), 6.91-6.87 (m, 4H), 6.66 (td, J=9.1 Hz, 2.5 Hz, 1H), 6.32 (t, J=9.7 Hz, 1H), 5.12 (b, 1H), 2.32 (td, J=12.7, 5.0, 1H), 2.20 (m, 1H), 1.32 (d, J=6.9 Hz, 3H) ppm.

trans-1-(p-methoxybenzoyl)-2-methyl-6-fluoro-N-(p-fluorophenyl)-N-(p-methoxybenzoyl)-1,2,3,4-tetrahydroquinolin-4-amine, Compound 30

Rf=0.31 (6/4 hexanes/EtOAc); $^1$H NMR (300 MHz, CDCl$_3$): δ 7.33-7.29 (m, 3H), 7.15 (d, J=8.8 Hz, 2H), 6.94-6.89 (m, 4H), 6.64 (dd, J=8.5, 2.7 Hz, 1H), 6.54 (dd, J=9.1, 5.2 Hz, 1H), 6.19 (dd, J=11.0, 8.0 Hz, 1H), 5.10 (b, 1H), 3.81 (s, 3H), 3.77 (s, 3H), 2.34 (td, J=13.2, 5.2 Hz, 1H), 2.17 (ddd, J=12.9, 8.0, 2.2 Hz, 1H), 1.31 (d, J=6.9 Hz, 3H) ppm.

Example 2

General Synthetic Procedures for Obtaining Compounds of Formula IV and their Characterization The structures of general Formula IV:

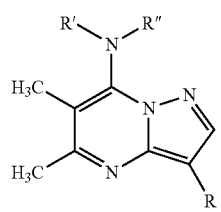

were synthesized according to the general synthetic procedure of Scheme 2:

Scheme 2. General synthetic procedure for preparing compounds of Formula IV.

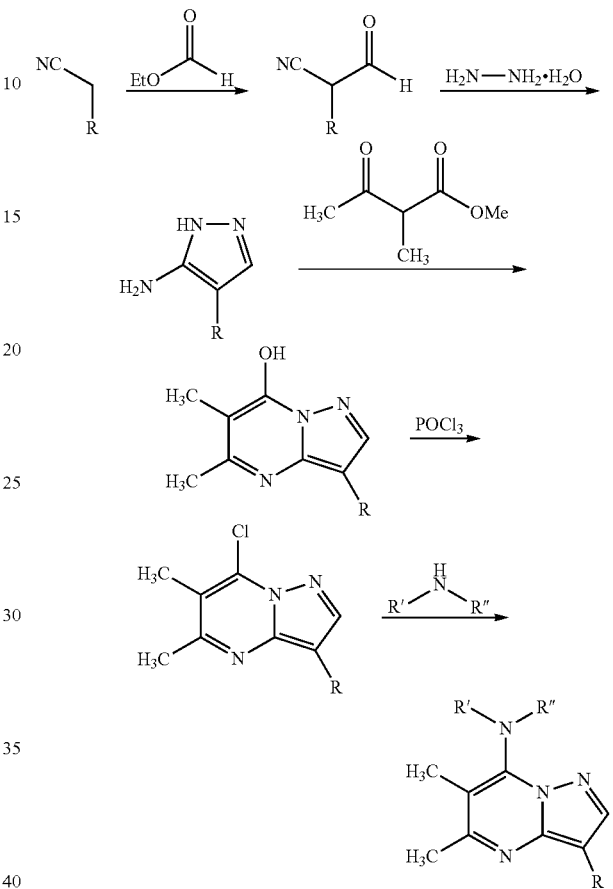

General procedure for reaction of alpha-substituted nitriles with ethyl carboxylates (first reaction in Scheme 2). A 2.2 M solution of NaOEt in ethanol (to deliver 1.2 equiv. of NaOEt) was added to a solution of the nitrile (1 equiv., 1M) at 21° C. The ethyl carboxylate was added and stirred at 40° C. for 2.5 hrs, cooled to 21° C., partitioned between water and benzene, vigorously stirred and brought to pH 2. The product was isolated by vacuum filtration.

General procedure for synthesis of 5-amino-substituted pyrazoles (reaction 2 in Scheme 2). Hydrazine monohydrate (2.4 equiv) was added to a solution of the alpha-substituted nitrile (1 equiv., 0.25 M) in 5% (v/v) acetic acid in toluene. The reaction mixture was brought to reflux for 6 hours, cooled to ambient temperature, and concentrated by rotary evaporation. 2N HCl$_{(aq)}$ was added to the residue thus obtained and washed with a 1/1 (v/v) mixture of ethyl acetate/hexanes. The acidic aqueous layer was treated with 28% NH$_4$OH$_{(aq)}$ until pH 10 and the product was extracted into ethyl acetate (4×), dried (Na$_2$SO$_4$), filtered, and concentrated to provide the amino-substituted pyrazole.

General procedure for synthesis of pyrazolopyridines (reaction 3 in Scheme 2). A beta-keto ester (1 equiv.) was added to a solution of the amino-substituted pyrazole (1 equiv. 0.5M) in acetic acid at 21° C. The reaction was brought to reflux for 12-18 hours, cooled to 21° C. and hexanes/diethyl ether (3/1) was added to the mixture to precipitate the product. The product was collected by vacuum filtration using hexanes/diethyl ether (3/1) to rinse.

General procedure for synthesis of 7-chloro-substituted pyrazolopyridines (reaction 4 in Scheme 2). Phosphorus oxychloride (5.4 equiv.) was added to a solution of 7-hydroxy-substituted pyrazolopyridine (1 equiv., 0.27 M) in toluene at 21° C., brought to reflux for 12 hours, cooled to 21° C., poured onto ice-water, extracted with EtOAc (3×), washed with sat. NaHCO$_{3(aq)}$ and sat. NaCl$_{(aq)}$, dried (Na$_2$SO$_4$), filtered, and concentrated to give the chloro-substituted pyrazolopyridine.

General procedure for synthesis of 7-amino-substituted pyrazolopyridines (reaction 5 in Scheme 2). Amine (5.5 equiv.) was added to a solution of the chloro-substituted pyrazolopyridine (1 equiv., 0.19 M) in 2-propanol at 21° C. The reaction was brought to reflux for 12-18 hours, cooled to 21° C., then stored in at −22° C. to precipitate the product.

Examples of compounds of general Formula IV synthesized are given in Table 2.

TABLE 2

Compounds of General Formula IV.

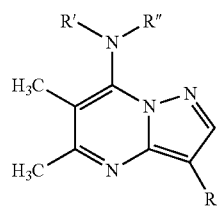

| Compound | R | R' | R'' |
|---|---|---|---|
| 2 | phenyl | —CH$_2$CH$_2$N(CH$_3$)$_2$ | H |
| 31 | phenyl | R', R'' = N-methylpiperazinyl | |
| 32 | phenyl | —CH$_2$CH$_2$CH(CH$_3$)$_2$ | H |
| 33 | phenyl | —CH$_2$CH$_2$CH$_2$N(CH$_3$)$_2$ | H |
| 34 | phenyl | —CH$_2$CH$_2$OCH$_3$ | H |
| 35 | phenyl | —CH$_2$C(CH$_3$)$_2$CH$_2$N(CH$_3$)$_2$ | H |
| 36 | phenyl | tetrahydropyran-7-yl | H |

Characterization of compounds of general Formula IV prepared by the procedure of Scheme 2 are the following:

3-phenyl-5,6-dimethyl-7-[N-(2-N,N-dimethylaminoethyl)amino]-pyrazolo[1,5-a]pyrimidine, Compound 2

ESI/MS m/z=310.0 (MH$^+$); $^1$H NMR (300 MHz, CDCl$_3$): δ 8.25 (s, 1H), 8.10-8.06 (m, 2H), 7.42 (m, 2H), 7.20 (m, 1H), 6.72 (b, 1H), 3.86 (m, 2H), 2.68 (m, 2H), 2.60 (s, 3H), 2.39 (m, 3H), 2.38 (s, 6H) ppm.

3-phenyl-5,6-dimethyl-7-(N-methyl-N-piperazinyl)-pyrazolo[1,5-a]pyrimidine, Compound 31

ESI/MS m/z=322.3 (MH$^+$); $^1$H NMR (300 MHz, CDCl$_3$): δ 8.27 (s, 1H), 8.08-8.05 (m, 2H), 7.43 (m, 2H), 7.22 (m, 1H), 3.64 (m, 4H), 2.70 (m, 4H), 2.61 (s, 3H), 2.45 (m, 3H), 2.31 (s, 3H) ppm.

3-phenyl-5,6-dimethyl-7-[N-(3-methylbutyl)amino]-pyrazolo[1,5-a]pyrimidine, Compound 32

ESI/MS m/z=309.2 (MH$^+$); $^1$H NMR (300 MHz, CDCl$_3$): δ 8.23 (s, 1H), 8.06 (m, 2H), 7.42 (m, 2H), 7.21 (m, 1H), 6.20 (b, 1H), 3.22 (q, J=6.9 Hz, 2H), 2.63 (m, 3H), 2.40 (s, 3H), 1.80 (m, 1H), 1.66 (q, J=7.1 Hz, 2H), 1.00 (d, J=6.3 Hz, 3H) ppm.

3-phenyl-5,6-dimethyl-7-[N-(2-N,N-dimethylaminopropyl)amino]-pyrazolo[1,5-a]pyrimidine, Compound 33

ESI/MS m/z=324.2 (MH$^+$); $^1$H NMR (300 MHz, CDCl$_3$): δ 8.23 (s, 1H), 8.08 (m, 2H), 7.42 (m, 2H), 7.19 (m, 1H), 3.91 (q, J=6.4 Hz, 2H), 2.59 (s, 3H), 2.50 (t, J=6.3 Hz, 2H), 2.34 (s, 3H), 2.31 (m, 6H), 1.89 (quintet, J=6.3 Hz, 2H) ppm.

3-phenyl-5,6-dimethyl-7-[N-(2-methoxyethyl)amino]-pyrazolo[1,5-a]pyrimidine, Compound 34

ESI/MS m/z=297.3 (MH$^+$); $^1$H NMR (300 MHz, CDCl$_3$): δ 8.25 (s, 1H), 8.08 (m, 2H), 7.42 (m, 2H), 7.21 (m, 1H), 6.34 (b, 1H), 3.92 (m, 2H), 3.66 (m, 2H), 3.45 (s, 3H), 2.60 (m, 3H), 2.36 (s, 3H) ppm.

7-((3-(N,N-dimethylamino)-2,2-dimethylpropane) amino)-5,6-dimethyl-3-phenylpyrazolo[1,5-a]pyrimidine, Compound 35

ESI/MS m/z=352.2 (MH$^+$); $^1$H NMR (300 MHz, CDCl$_3$): δ 8.22 (s, 1H), 8.15 (broad s, 1H), 8.09 (m, 2H), 7.41 (m, 2H), 7.18 (m, 1H), 3.83 (d, J=4.7 Hz, 2H), 2.58 (s, 3H), 2.40-2.39 (m, 8H), 2.32 (s, 3H), 1.05 (s, 6H) ppm.

7-((tetrahydropyran-4-yl)amino)-5,6-dimethyl-3-phenylpyrazolo[1,5-a]pyrimidine, Compound 36

ESI/MS m/z=323.3 (MH$^+$); $^1$H NMR (300 MHz, CDCl$_3$): δ 8.25 (s, 1H), 8.08 (m, 2H), 7.43 (m, 2H), 7.21 (m, 1H), 5.97 (d, J=9.1 Hz, 1H), 4.12 (m, 1H), 4.05 (dt, J=12.1, 4.1 Hz, 2H), 3.55 (td, J=11.1, 2.4 Hz, 2H), 2.62 (s, 3H), 2.35 (s, 3H), 2.05 (m, 2H), 1.79-1.66 (m, 2H) ppm.

2,5,6-trimethyl-7-[N-(2-N,N-dimethylaminoethyl) amino]-pyrazolo[1,5-a]pyrimidine Compound 37. ESI/MS m/z=248.1 (MH$^+$); $^1$H NMR (300 MHz, CDCl$_3$): δ 6.49 (m, 1H), 6.13 (s, 1H), 3.83 (m, 2H), 2.85 (m, 2H), 2.49 (s, 3H), 2.46 (m, 3H), 2.36 (s, 3H), 2.32 (s, 3H) ppm.

3-phenyl-2,5,6-trimethyl-7-[N-(2-N-methylaminoethyl)-N-methylamino]-pyrazolo[1,5-a]pyrimidine $^1$H NMR (300 MHz, CDCl$_3$): δ 10.92 (b, 2H), 7.68 (m, 2H), 7.48 (m, 2H), 7.33 (m, 1H), 3.70 (t, J=5.5 Hz, 2H), 3.24-3.22 (b, 6H), 2.84 (t, J=5.5 Hz, 2H), 2.60 (s, 6H), 2.31 (m, 3H) ppm.

3-phenyl-2,5,6-trimethyl-7-[N-(2-N-methylaminoethyl)-N-methylamino]-pyrazolo[1,5-a]pyrimidine ESI/MS m/z=324.0 (MH$^+$); $^1$H NMR (300 MHz, CDCl$_3$): δ 7.77 (m, 2H), 7.44 (m, 2H), 7.23 (m, 1H), 6.53 (t, J=5.3 Hz, 1H), 3.85 (q, J=5.2 Hz, 2H), 2.68 (q, 2H), 2.61 (s, 3H), 2.53 (m, 3H), 2.38 (s, 6H), 2.35 (s, 3H) ppm.

Example 3

General Synthetic Procedures for Obtaining Compounds of Formula VI and their Characterization The compounds of Formula VI:

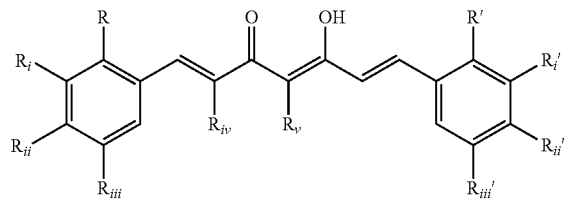

VI were synthesized according to the general synthetic procedure of Schemes 3 and 4:

Scheme 3. General synthetic procedures for preparing compounds of Formula VI.

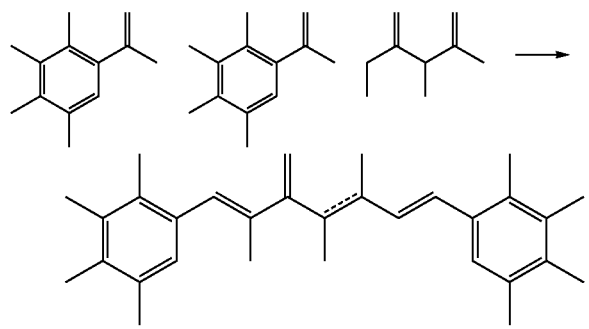

For Method A, boric anhydride (0.65 equiv.) was added to the 1,3-diketone (1 equiv, Scheme 3) or ketone (1 equiv., Scheme 4), stirred at room temperature for 1 h under Ar. Separately, the tri-n-butylborate (4.1 equiv.) was added to a solution of the aldehyde (2.0 equiv, 0.8 M) in ethyl acetate, the borate complex was added and n-butylamine (0.2 equiv) was added in 0.1 mL portions every 10 mins. The resulting mixture was stirred for 12-20 hrs, heated at 60° C., acidified with $HCl_{(aq)}$ (0.4 N, 1.5 mL per mmol of starting ketone or diketone) with stirring for 1 h, cooled and the organic layer was washed with water and brine, dried, filtered, concentrated to dryness, dissolved in EtOAc and MeOH (3/2) at −22° C. fridge overnight. The precipitate was collected by filtration, washed with cold MeOH, collected and dried to afford the product. For Method B of Schemes 3 and 4, the corresponding aldehyde (2 equiv.) was added to a mixture of either ketone or 1,3-diketone (1 equiv) and boric anhydride (1 equiv.). Morpholine (0.01 mL per mmol of ketone or 1,3-diketone) and acetic acid (0.01 mL per mmol of ketone or 1,3-diketone) was added, heated in a microwave at highest power for 1 min, cooled to room temperature, MeOH added and the precipitate filtered, washed with cold MeOH, dried and purified by silica gel flash column chromatography (hexane/EtOAc) to provide the desired product.

TABLE 3

Compounds of General Formula VI.

| Compound* | R, R' | $R_i$, $R_i'$ | $R_{ii}$, $R_{ii}'$ | $R_{iii}$, $R_{iii}'$ | $R_{iv}$ | $R_v$ |
|---|---|---|---|---|---|---|
| 38 | H | $OCH_3$ | OH | H | H | H |
| 39 | $OCH_3$ | H | $N(CH_3)_2$ | H | H | H |
| 40 | H | H | OH | H | H | $-CH_2CH_3$ |
| 41 | H | H | $N(CH_3)_2$ | H | H | $-CH_2CH_3$ |
| 42 | $OCH_3$ | H | H | F | H | $-CH_2CH_3$ |
| 43 | $OCH_3$ | H | $N(CH_3)_2$ | H | H | $-CH_2CH_3$ |
| 44 | H | H | $CF_3$ | H | H | H |
| 45 | H | H | $OCH_3$ | H | H | H |
| 46 | H | $OCH_3$ | H | H | H | H |
| 47 | H | H | $N(CH_3)_2$ | H | H | H |
| 48 | H | OH | $OCH_3$ | H | H | H |
| 49 | $OCH_3$ | H | OH | H | H | H |
| 50 | OH | H | $OCH_3$ | H | H | H |
| 51 | H | Cl | OH | H | H | H |
| 52 | $OCH_3$ | H | H | H | H | H |
| 53 | $OCH_3$ | H | H | F | H | H |
| 54 | H | H | OH | H | H | H |
| 55 | H | H | OH | H | $-CH_2CH_2CH_2-$ | |
| 56 | $OCH_3$ | H | H | F | $-CH_2CH_2CH_2-$ | |
| 57 | H | H | $N(CH_3)_2$ | H | $-CH_2CH_2CH_2-$ | |
| 58 | H | $OCH_3$ | OH | H | $-CH_2CH_2CH_2-$ | |
| 59 | $OCH_3$ | H | $N(CH_3)_2$ | H | $-CH_2CH_2CH_2-$ | |
| 60 | H | H | OH | H | $-CH_2CH_2-$ | |

*Single entries in the Table are degenerate for R, R' substituets; Cyclic groups are designated by alkyl chains that span two columns for $R_{iv}$ and $R_v$ 1,7-Bis(4-hydroxy-3-methoxyphenyl)-5-hydroxyhepta-1,4,6-trien-3-one (curcumin), Compound 38

Method A; ESI/MS m/z=369 (MH$^+$); $^1$H NMR (CDCl$_3$) δ 7.41 (d, J=15.6 Hz, 2H), 6.92 (m, 4H), 6.72 (m, 2H), 6.34 (d, J=15.6 Hz, 2H), 5.69 (s, 1H), 3.77 (s, 6H) ppm.

1,7-Bis(4-dimethylamino-2-methoxyphenyl)_5-hydroxy-hepta-1,4,6-trien-3-one, Compound 39

Method A; ESI/MS m/z=423 (MH$^+$); R$_f$=0.21 (2/1 hexanes/EtOAc); $^1$H NMR (CDCl$_3$): δ 7.90 (d, J=15.9 Hz, 2H), 7.43 (d, J=8.4 Hz, 2H), 6.54 (d, J=15.9 Hz, 2H), 6.40-6.19 (m, 4H), 5.76 (s, 1H) 3.90 (s, 6H), 3.05 (s, 12H) ppm.

4-Ethyl-5-hydroxy-1,7-bis(4-hydroxyphenyl)hepta-1,4,6-trien-3-one, Compound 40

Method A; ESI/MS m/z=335 (M$^-$); $^1$H NMR (DMSO): δ 7.77 (m, 6H), 7.14 (m, 2H), 6.84 (m, 4H), 2.75 (m, 2H), 1.08 (m, 3H) ppm.

1,7-Bis(4-dimethylaminophenyl)-4-ethyl-hepta-1,6-diene-3,5-dione, Compound 41

Method B; ESI/MS m/z=413 (MNa$^+$); R$_f$=0.8 (1/1 hexanes/EtOAc); $^1$H NMR (CDCl$_3$): δ 7.63 (d, J=15.3 Hz, 2H), 7.45 (m, 4H), 6.70-6.65 (m, 6H), 3.90 (t, J=7.8 Hz, 1H), 3.02 (m, 12H), 2.03 (m, 2H), 0.96 (t, J=6.0 Hz, 3H) ppm.

4-Ethyl-1,7-bis(5-fluoro-2-methoxyphenyl)-hepta-1,6-diene-3,5-dione, Compound 42

Method B; ESI/MS m/z=423 (MNa⁺); ¹H NMR (CDCl₃): δ 7.96-7.88 (m, J=16.2 Hz, 2H), 7.26-6.98 (m, 6H), 6.80 (d, J=16.2 Hz, 2H), 3.81 (d, J=9.6 Hz, 6H), 3.31 (m, 1H), 1.95 (m, 2H), 0.93 (m, 3H) ppm.

1,7-Bis(4-(dimethylamino)-2-methoxyphenyl)-4-ethyl-hepta-1,6-diene-3,5-dione, Compound 43

Method B; ESI/MS m/z=449 (MH⁻); $R_f$=0.19 (2/1 hexanes/EtOAc); ¹H NMR (CDCl₃): δ 8.00 (d, J=15.6 Hz, 2H), 7.44 (d, J=6.9 Hz, 2H), 6.80 (d, J=15.6 Hz, 2H), 6.25 (m, 4H), 4.03 (m, 1H), 3.88 (m, 6H), 3.05 (m, 12H), 2.01 (m, 2H), 0.95 (m, 3H) ppm.

1,7-Bis(4-(trifluoromethyl)phenyl)-5-hydroxyhepta-1,4,6-trien-3-one, Compound 44

Method B; ESI/MS m/z=411 (MH⁻); $R_f$=0.71 (8/1 hexanes/EtOAc); ¹H NMR (CDCl₃): δ 8.02 (m, 2H), 7.83 (m, 2H), 7.70 (m, 5H), 6.26 (m, 1H), 6.73 (d, J=16.2 Hz, 2H), 5.90 (s, 1H) ppm.

5-Hydroxy-1,7-bis-(4-methoxy-phenyl)-hepta-1,4,6-trien-3-one, Compound 45

Method A; ESI-MS m/z 335 (MH⁻); $R_f$=0.18 (5/1 hexanes/EtOAc); ¹H NMR (CD₃OD): δ 7.62 (d, J=15.9 Hz, 2H), 7.53 (m, 4H), 6.93 (m, 4H), 6.51 (d, J=15.9 Hz, 2H), 5.80 (s, 1H) ppm.

5-Hydroxy-1,7-bis-(3-hydroxyphenyl)-hepta-1,4,6-trien-3-one, Compound 46

Method A; ESI-MS m/z 309 (MH⁺); $R_f$=0.53 (1/1 hexanes/EtOAc); ¹H NMR (CDCl₃): δ 7.50 (d, J=15.9 Hz, 2H, Ph-CH), 7.16 (m, 2H, Ph), 7.00-6.95 (m, 4H, Ph), 6.78 (m, 2H, Ph), 6.53 (d, J=15.9 Hz, 2H, —CH—CO—), 5.80 (s, 1H, —CH—) ppm.

1,7-Bis-(4-dimethylaminophenyl)-5-hydroxy-hepta-1,4,6-trien-3-one, Compound 47

Method A; $R_f$=0.50 (2/1 hexanes/EtOAc); ¹H NMR (CDCl₃): δ 7.60 (d, J=15.6 Hz, 2H), 7.45 (m, 4H), 6.68 (m, 4H), 6.42 (d, J=15.6 Hz, 2H), 5.73 (s, 1H), 3.03 (s, 12H) ppm.

5-Hydroxy-1,7-bis-(3-hydroxy-4-methoxyphenyl)-hepta-1,4,6-trien-3-one, Compound 48

Method A; ESI-MS m/z 369 (MH⁺); $R_f$=0.43 (1/2 hexanes/EtOAc); ¹H NMR (CDCl₃): δ 7.40 (d, J=17.1 Hz; 2H), 6.99 (m, 2H), 6.91 (m, 2H), 6.73 (m, 2H), 6.34 (d, J=17.1 Hz, 2H), 5.70 (s, 1H), 3.78 (s, 6H) ppm.

5-Hydroxy-1,7-bis-(4-hydroxy-2-methoxyphenyl)-hepta-1,4,6-trien-3-one, Compound 49

Method A; ESI-MS m/z 367 (MH⁻); $R_f$=0.33 (2/1 hexanes/EtOAc); ¹H NMR (CDCl₃): δ 7.87 (d, J=16.2 Hz; 2H), 7.40 (m, 2H), 6.77 (m, 2H), 6.63 (m, 2H), 6.46 (m, 2H), 5.80 (s, 1H), 3.85 (s, 6H) ppm.

5-Hydroxy-1,7-bis-(2-hydroxy-4-methoxyphenyl)-hepta-1,4,6-trien-3-one, Compound 50

Method A; ESI-MS m/z 368 (MH⁺); $R_f$=0.30 (2/1 hexanes/EtOAc); ¹H NMR (CDCl₃): δ 8.08 (s, 2H), 7.05 (m, 4H), 6.38-6.30 (m, 4H), 3.80 (s, 6H) ppm.

1,7-Bis-(3-chloro-4-hydroxyphenyl)-5-Hydroxy-hepta-1,4,6-trien-3-one, Compound 51

Method A; ESI-MS m/z 376 (MH⁺); $R_f$=0.14 (2/1 hexanes/EtOAc); ¹H NMR (CDCl₃): δ 7.54 (d, J=15.9 Hz; 2H), 7.40-7.36 (m, 4H), 6.33 (s, 2H), 6.47 (d, J=15.9 Hz, 2H), 5.77 (s, 1H) ppm.

5-Hydroxy-1,7-bis-(2-methoxyphenyl)-hepta-1,4,6-trien-3-one, Compound 52

Method A; ESI-MS m/z 337 (MH⁺); $R_f$=0.38 (5/1 hexanes/EtOAc); ¹H NMR (CDCl₃): δ δ 8.05 (d, J=15.0 Hz, 2H), 7.85-7.60 (m, 4H), 7.11-6.70 (m, 4H), 6.66 (d, J=15.0 Hz, 2H) 6.00 (s, 1H), 3.90 (s, 6H) ppm.

1,7-Bis-(5-fluoro-2-methoxyphenyl)-5-Hydroxy-hepta-1,4,6-trien-3-one, Compound 53

Method A; ESI-MS m/z 371 (MH⁻); $R_f$=0.26 (5/1 hexanes/EtOAc); ¹H NMR (CDCl₃): δ 7.93 (d, J=15.0 Hz; 2H), 7.40 (m, 2H), 7.10-6.98 (m, 3H), 6.87-6.84 (m, 3H), 6.66 (d, J=15.0 Hz, 2H), 5.87 (s, 1H), 3.88 (s, 6H) ppm.

1,7-Bis(4-hydroxyphenyl)-5-hydroxy-hepta-1,4,6-trien-3-one (BDC), Compound 54

Method A; ESI-MS: m/z 309 (MH⁺); $R_f$=0.15 (2/1 hexanes/EtOAc); ¹H NMR (CD₃OD): δ 7.56 (d, J=16.2 Hz, 2H), 7.48 (m, 4H), 6.78 (m, 4H), 6.59 (d, J=15.7 Hz, 2H), 5.94 (s, 1H), ppm.

2-(4-Hydroxybenzylidene)-6-(3-(4-hydroxyphenyl)acryloyl)-cyclohexanone, Compound 55

Method A following recrystallization from EtOAc and MeOH. ESI/MS m/z=347 (M⁻); ¹H NMR (CDCl₃/CD₃OD, 9:1, v/v): δ 7.46 (m, 3H), 7.32 (d, J=9.3 Hz, 2H), 7.17 (d, J=9.3 Hz, 2H), 6.82 (d, J=15.9 Hz, 2H), 6.67 (m, 4H), 2.55 (m, 6H), 1.67 (m, 3H) ppm.

2-(5-Fluoro-2-methoxybenzylidene)-6-(3-(5-fluoro-2-methoxyphenyl)-1-hydroxyallylidene) cyclohexanone, Compound 56

Method B; ESI/MS m/z=411 (M⁻); ¹H NMR (CDCl₃): δ 8.05 (d, J=16.5 Hz, 1H), 7.81 (s, 1H), 7.17 (d, J=16.5 Hz, 1H), 7.05-6.96 (m, 3H), 6.88-6.81 (m, 3H), 3.86 (d, J=11.1 Hz, 6H), 2.67 (m, 2H), 2.60 (m, 2H), 1.80 (m, 2H) ppm.

2-(4-N,N-dimethylaminobenzylidene)-6-(3-(4-N,N-dimethylaminophenyl)acryloyl)cyclohexanone, Compound 57

Method A; ESI/MS: m/z=403 (MH⁺); $R_f$=0.67 (2/1 hexanes/EtOAc); ¹H NMR (CDCl₃): δ 7.72 (d, J=15.0 Hz, 1H), 7.65 (s, 1H), 7.50-7.38 (m, 4H), 6.92 (d, J=15.0 Hz, 1H), 6.70 (m, 4H), 3.03 (d, J=6.0 Hz, 12H), 2.67 (m, 2H), 2.65 (m, 2H), 1.79 (m, 2H) ppm.

2-(4-Hydroxy-3-methoxybenzylidene)-6-(3-(4-hydroxy-3-methoxyphenyl)acryloyl)cyclohexanone, Compound 58

Method A; ESI-MS m/z 407 (MH−); $R_f$=0.15 (3/2 hexanes/EtOAc); $^1$H NMR (CDCl$_3$) δ 7.73 (s, 1H), 7.67 (d, J=9 Hz, 1H), 7.16 (m, 1H), 7.06-6.93 (m, 6H), 3.96 (s, 3H), 3.92 (s, 3H), 2.77 (m, 2H), 2.67 (m, 2H), 1.81 (m, 2H) ppm.

2-(4-N,N-dimethylamino-2-methoxybenzylidene)-6-(3-(4-N,N-dimethylamino-2-methoxyphenyl)acryloyl)cyclohexanone, Compound 59

Method A; ESI-MS m/z 461 (MH−); $R_f$=0.72 (dichloromethane); $^1$H NMR (CDCl$_3$) δ 8.01 (d, J=15 Hz, 2H), 7.88 (s, 1H), 7.44 (m, 2H), 7.01 (d, J=15 Hz, 2H), 6.20 (m, 2H), 3.88 (d, J=6 Hz, 6H), 3.03 (d, J=6 Hz, 12H), 2.94 (m, 4H), 1.76 (m, 2H) ppm.

2-(1-Hydroxy-3-(4-hydroxyphenyl)allylidene)-5-(4-hydroxybenzyl idene) cyclopentanone, Compound 60

Method B; ESI-MS m/z=335 (MH+); $R_f$=0.48 (1/1 hexanes/EtOAc); $^1$H NMR (CD$_3$OD): δ 7.57 (d, J=16.5 Hz, 1H), 7.46-7.41 (m, 4H), 7.22 (m, 1H), 6.87-6.80 (m, 4H), 6.18 (d, J=16.5 Hz, 1H), 2.99 (m, 2H), 2.88 (m, 2H) ppm.

The following compounds were also prepared as examples of Formula VI of the invention:

1-(4-(dimethylamino)phenyl)-7-(5-fluoro-2-methoxyphenyl)hepta-1,6-diene-3,5-ione, Compound 61

Prepared by the following procedure: Boric anhydride (0.97 g, 14 mmol) was added to a solution of 2,4-pentadione (2 mL, 20 mmol) was dissolved in ethyl acetate (4 mL) and stirred at 70° C. for 40 min. 4-Dimethylaminobenzaldehyde (0.99 g, 6.7 mmol) and tributyl borate (1.8 mL, 6.7 mmol) was added to this solution. The resulting mixture was stirred at 70° C. for 30 min. Butylamine (0.66 mL, 6.7 mmol) was added dropwise over 20 min and then stirred at 100° C. for 1 h. To this mixture was added 1N HCl and the solution was stirred at 50° C. for 30 min. The solution was extracted with EtOAc and the resulting crude product was purified by chromatography (hexanes/EtOAc) to give 1-(4-(dimethylamino)phenyl)-5-hydroxyhexa-1,4-dien-3-one as a yellow solid. ESI-MS m/z 232 (MH+); $R_f$=0.27 (2/1 hexanes/EtOAc). This intermediate (100 mg, 0.43 mmol) and boric anhydride (21 mg, 0.3 mmol) were dissolved in ethyl acetate (4 mL) and stirred at 70° C. for 30 min. 5-fluoro-2-methoxybenzaldehyde (64.5 mg, 0.43 mmol) and tributylborate (0.23 mL, 0.86 mmol) were added. The reaction was stirred for 30 min at 70° C. Piperidine (0.04 mL, 0.43 mmol) was added dropwise and the mixture was stirred at 100° C. for 1 h then cooled to 60° C. and 1N HCl was added to reach pH 3-4. After 40 min and the reaction was cooled and extracted with ethyl acetate. The crude product was purified by preparative TLC (2/1 hexanes/EtOAc) to give compound 61. ESI-MS m/z 370 (MH+); $^1$H NMR (CDCl$_3$): δ 7.95 (d, J=18 Hz, 1H), 7.58-7.44 (m, J=15 Hz, 3H), 7.05 (m, 2H), 6.88 (m, 2H), 6.66 (m, 2H), 6.28 (d, J=15 Hz, 1H), 5.87 (s, 1H), 5.60 (s, 1H), 3.88 (s, 3H), 3.03 (s, 6H) ppm.

2-(4-Hydroxybenzyl)-6-(3-(4-hydroxyphenyl)propanoyl)cyclohexanone, Compound 62

Pd/C (6 mg) was added to compound 55 (30 mg, 0.086 mmol) in EtOAc (15 mL) and filled with H$_{2(g)}$, stirred at room temperature for 2 h, filtered and evaporated to give 62. ESI/MS: m/z=375 (MNa+); $^1$H NMR (CDCl$_3$): δ 7.04 (m, 4H), 6.75 (m, 4H), 3.14 (m, 1H), 2.84 (m, 2H), 2.70-2.57 (m, 4H), 2.18 (m, 2H), 1.63 (m, 4H) ppm.

5-Hydroxy-1,7-bis(4-hydroxyphenyl)hept-4-en-3-one, Compound 63

Pd/C (19 mg) was added to compound 54 (100 mg, 0.32 mmol) in EtOAc (15 mL) and filled with hydrogen. After 12 hours, the Pd/C was filtered off and the colorless solvent was removed to give the product 54. ESI/MS: m/z=311 (MH−); $^1$H NMR (CDCl$_3$): δ 7.00 (d, J=8.4 Hz, 4H), 6.66 (d, J=8.4 Hz, 4H), 5.50 (s, 1H), 2.77 (m, 4H), 2.52 (m, 4H) ppm.

2-(3-Cyclohexylacryloyl)-6-(cyclohexylmethylene) cyclohexanone, Compound 64

Method A; ESI/MS m/z=327 (MH−); $R_f$=0.1 (20/1 hexanes/ether); $^1$HNMR (CDCl$_3$): δ 6.53 (m, 2H), 4.96 (d, J=9.9 Hz, 1H), 3.79 (t, 1H), 2.5-2.28 (m, 6H), 1.71-1.04 (m, 22H) ppm.

3,5-bis(4-hydroxybenzyl idene)dihydro-2H-pyran-4(3H)-one, Compound 65

Method B; ESI/MS m/z=309 (MH+); $R_f$=0.42 (1/1 hexanes/EtOAc); $^1$H NMR (CDCl$_3$): δ 7.74 (m, 2H), 7.57 (m, 2H), 7.25 (m, 4H), 7.05 (m, 2H), 6.84 (m, 4H) ppm.

2-(4-N,N-Dimethylaminobenzylidene)-6-(3-(4-hydroxyphenyl)acryloyl)cyclohexanone, Compound 66

Prepared in 2 steps. Boric anhydride (571 mg, 8.2 mmol) was added to 2-acetylcyclohexanone (1.6 mL, 12.3 mmol) in EtOAc (2 mL) and then stirred at 70° C. for 40 min. 4-Hydroxybenzaldehyde (0.5 g, 4.1 mmol) and tributylborate (1.3 mL, 4.1 mmol) were added. After 30 min., n-butylamine (0.2 mL) was added dropwise and the solution was stirred at 100° C. for 1 h then cooled to 56° C. 0.4 N HCl (10 mL) was added and the mixture was stirred at 56° C. for 30 min, cooled to 56° C. extracted with EtOAc, washed with brine, dried, filtered and concentrated. The crude product was purified by flash chromatography (100% hexane to 50% EtOAc/hexane) to give 300 mg of the intermediate as yellow powder. ESI/MS m/z=243 (MH−), $^1$H NMR (CD$_3$OD/CDCl$_3$, 4/1, v/v): δ 7.60 (d, J=15.4 Hz, 1H), 7.46 (m, 2H), 6.85 (d, J=15.4 Hz, 1H), 6.79 (m, 2H), 2.54 (m, 2H), 2.37 (m, 2H), 1.74 (m, 4H). In step 2, boric anhydride (14.3 mg, 0.2 mmol) was added to the 2-(3-(4-hydroxyphenyl)acryloyl)cyclohexanone (50 mg, 0.2 mmol) from above, then 4-dimethylaminobenzaldehyde (30 mg, 0.2 mmol), morpholine (0.1 mL) and acetic acid (0.1 mL) were added. The reaction was heated in a microwave at the highest power for 1 min, MeOH added, sonicated, evaporated and the product was purified by flash chromatography (1/1 hexanes/EtOAc) to give 18 mg of the product as yellow solid. $R_f$=0.32; ESI-MS m/z=376 (MH+); $^1$H NMR (CDCl$_3$/CD$_3$OD, 30/1, v/v): δ 7.65 (s, 1H), 7.67 (m, 1H), 7.42 (m, 2H), 6.90 (m, 1H), 6.84-6.77 (m, 6H), 3.14 (s, 6H), 2.69 (m, 2H), 2.59 (m, 2H), 1.73 (m, 2H) ppm.

Additional compounds of general Formula VI of the invention were prepared following Scheme 4:

Scheme 4. Synthetic procedures for preparing additional compounds of Formula VI.

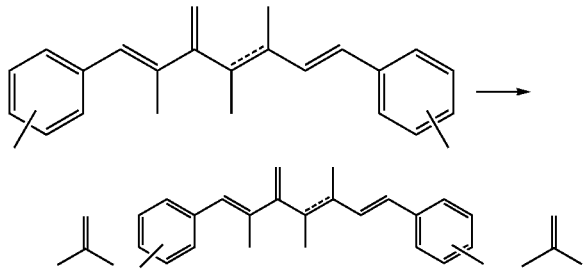

The synthesis of compounds according to Scheme 4 was performed using the general procedures of Method C or Method D.

was partitioned between $CH_2Cl_2$ and water, separated, dried ($Na_2SO_4$), filtered, concentrated, and purified using preparative TLC or silica gel flash column chromatography (hexanes/EtOAc). In step 2, HCl(g) was bubbled through the curcumin product above (1 equiv, 0.02 M) in EtOAc/$CH_2Cl_2$ (9/1) at 0° C. for 1-3 hours, evaporated, washed with ether to give the HCl salt.

Method D. A carboxylic acid chloride (2.1 equiv. per hydroxyl) was added to curcumin derivative (1 equiv., 0.01-0.1 M) and triethylamine (2.1 equiv. per hydroxyl) in $CH_2Cl_2$ After 2-16 h at 21° C., reaction was separated between $CH_2Cl_2$ and water, dried ($Na_2SO_4$), filtered, concentrated and purified using preparative TLC or silica gel flash column chromatography (hexanes/EtOAc) to give the esterified curcumin.

TABLE 4

Further Compounds of General Formula VI.

| Compound* | R, R' | $R_i$, $R_i'$ | $R_{ii}$, $R_{ii}'$ | $R_{iii}$, $R_{iii}'$ | $R_{iv}$ | $R_v$ |
|---|---|---|---|---|---|---|
| 67 | H | H | N-Boc-Valine- | H | H | H |
| 3 | H | H | Valine- | H | H | H |
| 68 | H | H | N,N'-diBoc-Lysine- | H | H | H |
| 69 | H | H | Lysine- | H | H | H |
| 70 | H | $OCH_3$ | N-Boc-Valine- | H | H | H |
| 71 | H | $OCH_3$ | Valine- | H | H | H |
| 72 | H | $OCH_3$ | N,N'-diBoc-Lysine- | H | H | H |
| 73 | H | $OCH_3$ | Lysine- | H | H | H |
| 74 | H | H | AcO- | H | H | H |
| 75 | H | H | $(CH_3)_3CC(O)O$— | H | H | H |
| 76 | H | H | N-Boc-Valine- | H | —$CH_2CH_2CH_2$— | |
| 4 | H | H | Valine- | H | —$CH_2CH_2CH_2$— | |
| 77 | H | $OCH_3$ | N-Boc-Valine- | H | —$CH_2CH_2CH_2$— | |
| 78 | H | $OCH_3$ | Valine- | H | —$CH_2CH_2CH_2$— | |
| 79 | H | $OCH_3$ | N,N'-diBoc-Lysine- | H | —$CH_2CH_2CH_2$— | |
| 80 | H | $OCH_3$ | Lysine- | H | —$CH_2CH_2CH_2$— | |
| 81 | H | H | N,N'-diBoc-Lysine- | H | —$CH_2CH_2CH_2$— | |
| 82 | H | H | Lysine- | H | —$CH_2CH_2CH_2$— | |
| 83 | H | H | $R_{ii}$ = OH, $R_{ii}'$ = N-Boc-Valine- | H | H | H |
| 84 | H | H | $R_{ii}$ = OH, $R_{ii}'$ = Valine- | H | H | H |

*Single entries in the Table are degenerate for R, R' substituets; Cyclic groups are designated by alkyl chains that span two columns for $R_{iv}$ and $R_v$; amino acid denotes the C-terminal ester, e.g. for Valine-:

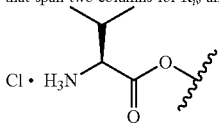

Method C. Dicyclohexylcarbodiimide (DCC, 1.25 equiv. per hydroxyl) or 1-[3-(dimethylamino)propyl]-3-ethylcarbodiimide hydrochloride (EDC, 1.25 equiv per hydroxyl) was added to the curcumin derivative (1 equiv., 0.012 M) and the carboxylic acid (2.0 equiv. per hydroxyl) in $CH_2Cl_2$/DMF (5/1). In some cases, 4-(N,N-dimethylamino)pyridine (DMAP, 0.2 equiv.) was added. After 2-16 hours at 21 CC, (2S,2'S)—O,O'-(3-hydroxy-5-oxohepta-1,3,6-triene-1,7-diyl)bis(4,1-phenylene) bis(2-(N-tert-butoxycarbonylamino)-3-methylbutanoate), Compound 67

Method C step 1 used DCC; ESI/MS: m/z=729.1 ($MNa^+$); $R_f$=0.3 (3/1 hexanes/EtOAc); $^1$H NMR ($CDCl_3$) δ 7.64 (d, J=16.5 Hz, 2H), 7.58 (d, J=9.3 Hz, 4H), 7.14 (d, J=9.3, 4H), 6.59 (d, J=16.5 Hz, 2H), 5.84 (s, 1H), 5.06 (m, 2H), 4.46 (m, 2H), 2.34 (m, 2H), 1.47 (s, 18H), 1.09 (d, J=6.9 Hz, 6H), 1.03 (d, J=6.9 Hz, 6H) ppm.

(2S,2'S)—O,O'-(3-hydroxy-5-oxohepta-1,3,6-triene-1,7-diyl)bis(4,1-phenylene) bis(2-amino-3-methylbutanoate) HCl salt, Compound 3

Method C step 2; ESI/MS: m/z=506.9 (MH$^+$); $^1$H NMR (CD$_3$OD): δ 7.76 (d, J=8.4 Hz, 4H), 7.69 (d, J=15.9 Hz, 2H), 7.26 (d, J=8.4 Hz, 4H), 6.85 (d, J=15.9 Hz, 2H), 6.10 (s, 1H), 4.25 (d, J=4.8 Hz, 2H), 2.5 (m, 2H), 1.22-1.19 (m, 12H) ppm.

(2S,2'S)—O,O'-(3,5-Dioxohepta-1,6-diene-1,7-diyl)bis(4,1-phenylene) bis(2,6-bis(tert-butoxycarbonylamino)hexanoate), Compound 68

Method C; ESI/MS: m/z=729 (MNa$^+$); R$_f$=0.3 (3/1 hexanes/EtOAc); $^1$H NMR (CDCl$_3$): δ 7.64 (d, J=16.5 Hz, 2H), 7.58 (d, J=9.3 Hz, 4H), 7.14 (d, J=9.3, 4H), 6.59 (d, J=16.5 Hz, 2H), 5.84 (s, 1H), 5.06 (m, 2H), 4.46 (m, 2H), 2.34 (m, 2H), 1.47 (s, 18H), 1.09 (d, J=6.9 Hz, 6H), 1.03 (d, J=6.9 Hz, 6H) ppm.

(2S,2'S)—O,O'-(3,5-Dioxohepta-1,6-diene-1,7-diyl)bis(4,1-phenylene) bis(2,6-bis-amino)hexanoate HCl salt, Compound 69

Method C; ESI/MS: m/z=565 (MH$^+$); $^1$H NMR (CD$_3$OD): δ 7.80 (m, 2H), 7.54 (m, 4H), 7.32 (m, 2H), 6.84 (m, 4H), 4.41 (m, 4H), 3.01 (m, 4H), 2.18 (m, 6H), 1.81 (m, 4H) ppm.

(2S,2'S)—O,O'-(3-hydroxy-5-oxohepta-1,3,6-triene-1,7-diyl)bis(2-methoxy-4,1-phenylene) bis(2-(N-tert-butoxycarbonylamino)-3-methylbutanoate), Compound 70

Method C and purified by preparative TLC (2/1 hexanes/EtOAc); ESI/MS: m/z=789.5 (MNa$^+$); R$_f$=0.4 (2/1 hexanes/EtOAc); $^1$H NMR (CDCl$_3$): δ 7.65 (d, J=15.3 Hz, 2H), 7.18-7.06 (m, 6H), 6.56 (d, J=15.3 Hz, 2H), 5.90 (s, 1H), 4.54 (m, 2H), 3.84 (s, 6H), 2.40 (m, 2H), 1.47 (s, 18H), 1.25 (m, 12H), 4.45 (m, 2H), 3.16 (m, 4H), 1.46 (s, 36H) ppm.

(2S,2'S)—O,O'-(3-hydroxy-5-oxohepta-1,3,6-triene-1,7-diyl)bis(2-methoxy-4,1-phenylene) bis(2-amino-3-methylbutanoate) HCl salt, Compound 71

Method C; ESI/MS: m/z=567 (MH$^+$); $^1$H NMR (CD$_3$OD): δ 7.70 (d, J=16.2 Hz, 2H), 7.43 (s, 2H), 7.30 (m, 2H), 7.18 (d, J=8.1 Hz, 2H), 6.88 (d, J=16.2 Hz, 2H), 6.10 (s, 1H), 4.27 (m, 2H), 3.91 (s, 6H), 2.50 (m, 2H), 1.24 (m, 12H) ppm.

(2S,2'S)—O,O'-(3,5-Dioxohepta-1,6-diene-1,7-diyl)bis(2-methoxy-4,1-phenylene) bis(2,6-bis(tert-butoxycarbonylamino)hexanoate), Compound 72

Method C and purified by preparative TLC (1/1 hexanes/EtOAc); ESI/MS: m/z=1048 (MNa$^+$); R$_f$=4.9 (1/1 hexanes/EtOAc 1/1); $^1$H NMR (CDCl$_3$) δ 7.61 (d, J=15.6 Hz, 2H), 7.40 (m, 4H), 7.05 (m, 4H), 6.86 (m, 4H), 6.44 (m, 1H), 5.73 (m, 2H), 5.29 (m, 2H), 4.68 (m, 2H), 4.45 (m, 2H), 3.16 (m, 4H), 1.46 (s, 36H) ppm.

(2S,2'S)—O,O'-(3,5-Di oxohepta-1,6-diene-1,7-diyl) bis(4,1-phenylene) bis(2,6-bis-amino)hexanoate HCl salt, Compound 73

Method C; ESI/MS: m/z=647 (MNa$^+$); $^1$H NMR (CD$_3$OD): δ 7.68 (d, J=16.2 Hz, 2H), 7.44 (m, 2H), 7.31 (m, 2H), 7.20 (d, J=8.1 Hz, 2H), 6.89 (d, J=16.2 Hz, 2H), 6.13 (s, 1H), 4.41 (t, J=6.3 Hz, 2H), 3.96 (t, J=6.3 Hz, 2H), 3.92 (s, 6H), 2.98 (m, 6H), 2.15-1.76 (m, 6H) ppm.

Acetic acid 4-(7-(4-acetoxy-phenyl)-5-hydroxy-3-oxo-hepta-1,4,6-trienyl)phenyl ester, Compound 74

Method D; R$_f$=0.71 (1/1 hexanes/EtOAc); $^1$H NMR (CDCl$_3$) δ 7.70 (d, J=18.0 Hz, 2H, Ph-CH—), 7.61 (m, 4H, Ph), 7.17 (m, 4H, Ph), 6.60 (d, J=18.0 Hz, 2H, —CH—CO—), 5.87 (s, 1H, —CH—), 2.35 (s, 6H, 2×CH$_3$) ppm.

2,2-Dimethyl-propionic acid 4-(7-(4-(2,2-dimethyl-propionyloxy)-phenyl)-3,5-dioxo-hepta-1,6-dienyl)phenyl ester, Compound 75

Method D; ESI-MS m/z 477 (MH$^+$); R$_f$=0.35 (4/1 hexanes/EtOAc); $^1$H NMR (CDCl$_3$): δ 7.70 (d, J=18.0 Hz, 2H, Ph-CH—), 7.6 (m, 4H, Ph), 7.17 (m, 4H, Ph), 6.60 (d, J=18.0 Hz, 2H, —CH—CO—), 5.87 (s, 1H, —CH—), 1.22 (s, 18H, 2×(CH$_3$)$_3$) ppm.

(2 S,2'S)-4-(3-(3-(4-(2-(tert-Butoxycarbonylamino)-3-methyl butanoyl oxy)benzylidene)-2-oxocyclohexyl)-3-oxoprop-1-enyl)phenyl bis(2-(tert-butoxycarbonylamino)-3-methylbutanoate), Compound 76

Method C purified by preparative TLC (3/1 hexanes/EtOAc); ESI/MS: m/z=747 (MH$^+$); R$_f$=0.47 (3/1 hexanes/EtOAc); $^1$H NMR (CDCl$_3$): δ 7.78 (d, J=15.0 Hz, 1H), 7.69 (s, 1H), 7.60-7.42 (m, 4H), 7.16 (m, 4H), 7.06 (d, J=15.0 Hz, 1H), 5.07 (m, 1H), 4.48 (m, 2H), 2.69 (m, 4H), 2.33 (m, 2H), 1.82 (m, 2H), 1.47 (s, 18H), 1.10 (m, 12H) ppm.

4-((1E,3Z)-3-(3-((E)-4-((L-valyl)oxy)benzylidene)-2-oxocyclohexylidene)-3-hydroxyprop-1-en-1-yl)phenyl L-valinate HCl Salt, Compound 4

Method C; ESI/MS m/z=547 (MH$^+$); $^1$H NMR (CD$_3$OD): δ 7.81 (d, J=8.4 Hz, 2H), 7.73 (d, J=16.5 Hz, 2H), 7.55 (d, J=8.4 Hz, 2H), 7.33 (m, 5H), 4.26 (m, 2H), 2.76 (m, 4H), 2.50 (m, 2H), 1.82 (m, 2H), 1.21 (m, 12H) ppm.

(2 S,2'S)4-(3-(3-(4-(2-(tert-Butoxycarbonylamino)-3-methyl butanoyl oxy)-3-methoxybenzylidene)-2-oxocyclohexyl)-3-oxoprop-1-enyl)-2-methoxyphenyl bis(2-(tert-butoxycarbonylamino)-3-methylbutanoate), Compound 77

Method C; purified by preparative TLC (2/1 hexanes/EtOAc); ESI/MS: 829 (MNa$^+$); R$_f$=0.41 (2/1 hexanes/EtOAc); $^1$H NMR (CDCl$_3$): δ 7.75 (s, 1H), 7.68 (d, J=7.9 Hz, 2H), 7.21 (d, J=7.9 Hz, 1H), 7.12-6.99 (m, 6H), 5.10 (m, 2H), 4.53 (m, 2H), 3.85 (s, 3H), 3.82 (s, 3H), 2.75-2.66 (m, 4H), 2.40 (m, 2H), 1.82 (m, 2H), 1.31 (s, 18H), 1.08 (m, 12H) ppm.

(2S,2'S)4-(3-(3-(4-(2-amino-3-methylbutanoyloxy)-3-methoxybenzylidene)-2-oxocyclohexyl)-3-oxo-prop-1-enyl)-2-methoxyphenyl bis(2-(tert-butoxycarbonylamino)-3-methylbutanoate) HCl salt, Compound 78

Method C; ESI/MS m/z=607 (MH$^+$); $^1$H NMR (CD$_3$OD): δ 7.72 (m, 2H), 7.45 (m, 2H), 7.34-7.11 (m, 6H), 4.27 (m, 2H), 3.91 (s, 3H), 3.87 (s, 3H), 2.77 (m, 4H), 2.50 (m, 3H), 1.81 (m, 2H), 1.23 (m, 12H) ppm.

4-(3-(3-(4-(2,6-Bis(tert-butoxycarbonylamino) hexanoyloxy)-3-methoxybenzylidene)-2-oxocyclohexyl)-3-oxoprop-1-enyl)-2-methoxyphenyl bis(2,6-bis(tert-butoxycarbonylamino)hexanoate), Compound 79

Method C; ESI/MS: m/z=1087 (MNa$^+$); R$_f$=0.48 (1/1 hexanes/EtOAc); $^1$H NMR (CDCl$_3$): δ 7.75 (s, 1H), 7.67 (d, J=7.9 Hz, 2H), 7.25 (m, 1H), 7.12-6.99 (m, 6H), 5.24 (m, 4H), 4.64 (m, 4H), 4.29 (m, 4H), 3.86 (s, 3H), 3.81 (s, 3H), 3.13 (m, 8H), 2.68 (m, 4H), 1.82 (m, 2H), 1.31 (s, 18H) ppm.

4-(3-(3-(4-(2,6-diaminohexanoyloxy)-3-methoxybenzylidene)-2-oxocyclohexyl)-3-oxoprop-1-enyl)-2-methoxyphenyl bis(2,6-diaminohexanoate) HCl salt, Compound 80

Method C; ESI/MS m/z=664 (MH$^+$); $^1$H NMR (CD$_3$OD): δ 7.72 (m, 2H), 7.46 (s, 1H), 7.34-7.11 (m, 6H), 4.41 (t, J=6 Hz, 4H), 4.05 (t, J=6 Hz, 4H), 3.93 (s, 3H), 3.88 (s, 3H), 3.01 (m, 8H), 2.78 (m, 4H), 2.01 (m, 2H) ppm.

(2S,2'S)-4-(3-(4-(2,6-Bis(tert-butoxycarbonylamino) hexanoyloxy)benzylidene)-3-hydroxyprop-1-enyl) phenyl bis(2,6-bis(tert-butoxycarbonylamino) hexanoate), Compound 81

Method C; ESI/MS m/z=1005 (MH$^+$); R$_f$=0.61 (1/1 hexanes/EtOAc); $^1$H NMR (CDCl$_3$): δ 7.77 (d, J=15.6 Hz, 1H), 7.69 (s, 1H), 7.62 (d, J=9.6 Hz, 2H), 7.45 (d, J=9.6 Hz, 2H), 7.16-7.04 (m, J=15.6 Hz, 5H), 5.20 (m, 2H), 4.54 (m, 4H), 3.15 (m, 4H), 2.68 (m, 4H), 1.96 (m, 4H), 1.80 (m, 4H), 1.47 (s, 36H) ppm.

(2S,2'S)-4-(3-(4-(2,6-Diaminohexanoyloxy)benzylidene)-2-oxocyclohexyl)-3-oxoprop-1-enyl)phenyl bis(2,6-diaminohexanoate) HCl salt, Compound 82

Method C; ESI/MS m/z=605 (MH$^+$); $^1$H NMR (CDCl$_3$) δ 7.79 (d, J=8.4 Hz, 2H), 7.70 (d, J=16.5 Hz, 2H), 7.54 (d, J=8.4 Hz, 2H), 7.32 (m, 5H), 4.96 (m, 2H), 4.39 (m, 4H), 2.99 (m, 8H), 2.73 (m, 4H), 2.22-1.53 (m, 6H) ppm.

(S)-4-(3-hydroxy-7-(4-hydroxyphenyl)-5-oxohepta-1,3,6-trienyl)phenyl 2-N-Boc-amino-3-methylbutanoate HCl salt, Compound 83

Method C using 1 molar equivalent of valine; $^1$H NMR (CDCl$_3$) δ 7.63 (m, 2H), 7.58 (m, 2H), 7.47 (m, 2H), 7.13 (m, 2H), 6.86 (m, 2H), 6.55 (m, 1H), 5.82 (s, 1H), 5.09 (m, 1H), 4.48 (s, 1H), 2.35 (m, 1H), 1.50 (m, 9H), 1.12 (d, J=6.9 Hz, 1H), 1.06 (d, J=6.9 Hz, 1H) ppm.

(S)-4-(3-hydroxy-7-(4-hydroxyphenyl)-5-oxohepta-1,3,6-trienyl)phenyl 2-amino-3-methylbutanoate HCl salt, Compound 84

Method C; ESI/MS: m/z=407.2 (MH$^+$); $^1$H NMR (CD$_3$OD): δ 7.73 (m, 2H), 7.63 (m, 2H), 7.50 (m, 2H), 7.23 (m, 2H), 6.84-6.78 (m, 3H), 6.66-6.71 (m, 1H), 1.2 (m, 6H) ppm. (other peaks overlapping with solvent signals)

Example 4

Preparation of a Tricalcium Phosphate Matrix

The TCP powder was ground and sieved and then treated with a solution of 2% hydrogen peroxide (1.0 g of powder/ 1.2 mL solution) and naphthalene particles (710-1400 μm, at a ratio of 1.0 g of powder/0.3 g naphthalene particles) at 60° C. Subsequently, the naphthalene was evaporated at 80° C. and the porous green bodies were dried. Porous tricalcium phosphate was obtained by sintering the green bodies at 1100° C. for 8 h. The resulting ceramic was cleaned ultrasonically with acetone, then 70% ethanol and demineralized water, dried at 80° C., and sterilized by gamma irradiation prior to use.

Example 5

Adsorption of Compounds onto Matrix

The compounds of general Formula II, IV, and VI were adsorbed onto the surface of a matrix such as calcium phosphate-derived materials as a non-limiting example of the substances of the invention and methods for preparation.

A compound of Formula II, IV, or VI was dissolved in an organic solvent, either MeOH or preferably ethyl acetate, and combined with the matrix (e.g., calcium phosphate-derived materials). The suspension of matrix-compound solution was combined for 10 minutes at RT, evaporated, and dried under vacuum. Once the compound-fortified matrix was obtained, kinetics showed slow release of the compound (e.g., t$_{1/2}$ of 353 min for 1 in water) in the presence of water, serum, or cell media, sufficient for slow release to modulate cells in vitro or in vivo. To prepare a matrix formulated at 0.03% (wt/wt) with 3, capable of delivering up to 0.3 μg of compound/mg ceramic in solution, 6 μg of 3 in MeOH was added to ~20 mg of ceramic. After 10 minutes, the organic solvent was removed to provide the yellow-orange coated ceramic for in vitro and/or in vivo use.

Example 6

Wnt Transcriptional Reporter Assay for Screening Compounds

Commercially available Super(8x)TOPflash vector driven by a (7x) TCF-firefly luciferase response element was transiently transfected into HEK293T cells, together with a TK-driven Renilla luciferase plasmid as an internal control to normalize the luminescence signal and a Wnt3A-expressing vector as the source of pathway activation. HEK293T cells were transfected with plasmids in DMEM plus 10% fetal bovine serum (FBS) for 8 hr, replated to 96-well plates in DMEM plus 10% FBS followed by treatment with compounds (1.6 nM to 5 μM) (DMSO final concentration is 0.5%) for 20 hrs. Firefly and Renilla Luciferase activities were measured and normalized by the renilla luciferase values. Maximum activation of Wnt response in the assay was around 300% with the most potent activators (Table 5).

TABLE 5

| Effect of compounds on Wnt transcription | |
| --- | --- |
| Compound | Wnt transcription potency |
| 1 | +++ |
| 2 | + |

TABLE 5-continued

Effect of compounds on Wnt transcription

| Compound | Wnt transcription potency |
|---|---|
| 31 | ++ |
| 32 | + |

*Wnt potency is reported relative to the transcription of cells treated with DMSO alone.
+, EC50 > 40 nM; ++, 15 nM < EC50 < 40 nM; +++, EC50 < 15 nM

Example 7

C2C12 Cell Transdifferentiation with Substances of the Invention. Protocols for the Characterization of the Transdifferentiation Process Mouse myoblast C2C12 cells were used at low passage (<15 passage). C2C12 cells were cultured at 37° C. in 5% $CO_2$ in DMEM media supplemented with 10% heat inactivated FBS (growth media).

Alkaline Phosphatase (ALP) Functional Activity Assay: C2C12 cells were plated into 12-well plates with 7,000 cells/well in 1 mL growth media. After an overnight incubation, calcium phosphate ceramic (5 mg/well) was added to the cells. 1, 2, 3, or 4 in 0.1% DMSO was added (500 nM). Half the media was exchanged with fresh media containing compound every 48 hrs. After 6 days, media was removed, ALP Lysis Buffer (10 mM Tris-HCl pH 8.0, 1 mM $MgCl_2$, and 1% Triton X100) added, and cell lysate obtained (10 min incubation at RT) by centrifugation (5 min at 3500×g at 4° C.). Para-nitrophenol phosphate (pNPP) (2 mg/mL) was incubated with 50 µl cell lysate (10 mins, 37° C.). After addition of 100 µl 0.02 N NaOH, absorbance $OD_{405}$ was measured. Protein concentration was determined by Bradford protein assay. Results of ALP activity were plotted as nM pNP hydrolyzed/mg total protein. After normalizing control samples (i.e., DMSO-treated samples) to one-fold, the fold-changes were plotted to indicate the relative ALP activity. Osteogenic potency (increase of ALP activity) of 23 compounds of Formula II or IV (Wnt signaling pathway activators) (Table 6) and 20 compounds of Formula VI (TLR signaling pathway activators) (Table 7) showed some compounds tested were osteogenic but in the presence of calcium phosphate matrix, significant increase in ALP activity was observed. This protocol was applied to hMSC and E15 cells as well.

qPCR Detection of Osteogenic Markers:

Cells were cultured with compound in the presence or absence of matrix as described above, but using 96-well plate format. Total RNA was extracted from cells (as above) using Trizol. cDNA was made using 750 ng of total RNA with Bio-Rad iscript kit and was diluted 20-fold before being used for qPCR. qPCR was conducted under the following conditions: 95° C., 2 min; 95° C., 10 s and 60° C., 45 s for 40 cycles; 60° C. for 71 cycles for melt curve. qPCR results were analyzed by the ΔΔCt method. 18s rRNA was used as an internal standard. This protocol was applied to hMSC and E15 cells.

TABLE 6

Effect of compounds of Formula II or IV in the presence or absence of matrix on ALP activity in C2C12 cells.

| | ALP activity | |
|---|---|---|
| Compound | −matrix | +matrix |
| 11 | − | ++ |
| 26 | − | ++ |
| 15 | − | ++ |
| 20 | − | ++ |
| 19 | − | − |
| 28 | − | − |
| 32 | − | − |
| 30 | − | + |
| 8 | + | + |
| 31 | + | + |
| 27 | + | + |
| 22 | + | − |
| 25 | + | + |
| 7 | + | + |
| 21 | + | + |
| 5 | + | + |
| 23 | ++ | + |
| 6 | ++ | − |
| 24 | ++ | − |
| 29 | +++ | − |
| 12 | +++ | + |
| 13 | +++ | − |
| 18 | +++ | − |

*ALP activity was determined and normalized to DMSO treatment.
−, <5%; +, 5-50%; ++, 50-100%; +++, >100%.
NA, not available.

TABLE 7

Effect of compounds of Formula VI in the presence or absence of matrix on ALP activity in C2C12 cells.

| | ALP activity | |
|---|---|---|
| Compound | −matrix | +matrix |
| 62 | − | + |
| 59 | − | ++ |
| 57 | − | ++ |
| 56 | − | +++ |
| 53 | − | − |
| 69 | − | + |
| 78 | − | + |
| 80 | − | + |
| 83 | + | − |
| 38 | + | +++ |
| 71 | + | + |
| 55 | + | + |
| 58 | + | + |
| 54 | + | ++ |
| 64 | + | + |
| 63 | + | ++ |
| 49 | ++ | − |
| 39 | +++ | − |
| 48 | +++ | − |
| 47 | +++ | − |

*ALP activity was determined and normalized to DMSO treatment.
−, <5%; +, 5-50%; ++, 50-100%; +++, >100%.
NA, not available.

Cell Proliferation/Viability Assay:

Cells were seeded at a density of 500 cells/well on 96-well plates. After 24 hr, compound (i.e., 5 nM, 50 nM, 500 nM or 5000 nM) was added to the cells in the presence or absence of calcium phosphate matrix (5 mg/mL). One-half of the media was replaced with fresh media containing compound every 48 hours for 8 days. At the specified time, 1 µg of Resazurin was added to each well of the 96-well plate and the fluorescence signal at 590 nm (excitation at 530 nm) was immediately measured. Readings were designated as time zero values (value$_{0h}$). Cells were incubated for 1 hr before a second fluorescence measurement at 590 nm was made (value$_{1h}$). The difference in 1 hr and 0 h (value$_{1h}$–value$_{0h}$) readings were used to plot the fold-change in cell proliferation/viability after normalizing to control conditions (i.e., DMSO vehicle treatment). Compounds of Formula II or IV that activate Wnt signaling and compounds of Formula VI that activate TLR signaling pathways were analyzed. This protocol was applied to hMSC and E15 cells as well. Cell proliferation was not robust in keeping with a narrow number of cells highly committed to the bone cell lineage.

Alizarin Red S Staining:

C2C12 cells were cultured as described for the ALP functional activity assay (above, except compound was added every 48 hr for 25 days), but using 48-well plate format. On day 25, medium was removed and the cells were washed with PBS (calcium and magnesium free). Cells were fixed with 70% ethanol at room temperature for 30 mins, rinsed with water 3×. Following removal of water, 200 µl of Alizarin Red S (2%, pH 4.1) was added to each well and incubated for at least 20 mins. The dye was removed and the cells were washed with excess H$_2$O four times with gentle mixing. The cells were covered with water to prevent evaporation and analyzed by plate reader or microscope. This protocol was applied to hMSC and E15 cells.

Example 8

Effect of 1, 2, 3, or 4 on C2C12 Cells in the Presence or Absence of Calcium Phosphate Ceramic Matrix 1. ALP Activity.

Compounds 1, 2, 3, and 4 (500 nM) induced osteogenesis (ALP activity) in C2C12 cells (1.7- to 6-fold) versus untreated cells (Table 8 and FIG. 1). Compared to C2C12 cells treated without ceramic, in the presence of calcium phosphate ceramic (5 mg/mL), 1-4 (500 nM) induced osteogenesis (ALP activity) 2.3- to 22-fold greater (Table 8 and FIG. 1).

TABLE 8

Effect of Compounds 1-4 on ALP activity in the presence or absence of matrix in C2C12 cells after 6 days of culture.

| | ALP activity fold-changes +/− SD | |
|---|---|---|
| Compound | −matrix | +matrix |
| DMSO | 1.0 ± 0.1 | 4.0 ± 0.4 |
| rhBMP-2 | 4.0 ± 0.4 | 7.1 ± 0.7 |
| 1 | 5.7 ± 0.6 | 19.4 ± 2.0 |
| 2 | 3.9 ± 0.4 | 23.6 ± 2.5 |
| 3 | 1.7 ± 0.2 | 2.1 ± 0..2 |
| 4 | 1.7 ± 0.2 | 2.6 ± 0.3 |

2. Biomarkers.

Compared to untreated cells, compounds 1, 2, 3 or 4 (500 nM) induced expression of osteogenic biomarker (collagen I mRNA) in C2C12 cells 1.2- to 5-fold (6 days of treatment described in Example 7).

Compared to treated C2C12 cells without matrix, cells treated with 1, 2, 3 or 4 (500 nM) in the presence of calcium phosphate ceramic (5 mg/mL) markedly induced expression of osteogenic biomarker (i.e., collagen I mRNA) 10- to 90-fold greater (6 days treatment, Example 7).

Compared to treated cells in the absence of matrix, compounds 1, 2 3 or 4 (500 nM) induced increased expression of Wnt pathway related-protein mRNA (i.e., ID3 mRNA) that has been associated with osteogenesis. For example, in the absence of matrix, 1 induced increased expression of ID3 mRNA 1.8-fold; in the presence of matrix, compound 1 and 2 induced increased expression of ID3 mRNA 5.0-fold and 1.7-fold, respectively (6 days of treatment, Example 7).

Compounds 1, 2, 3 or 4 (500 nM) alone induced marked calcium deposition of C2C12 cells. In the absence of matrix, 1 and 2 increased calcium deposition 1.6-fold and 2.0-fold, respectively. In the presence of matrix, 1 and 2 induced increased calcium deposition 2.5-fold and 2.3-fold, respectively (25 days of treatment, Example 7).

Example 9

Lack of Toxicity of Compounds 1, 2, 3 or 4 in C2C12 Cells

An Alamar blue assay of C2C12 cells cultured for 25-days that had been treated with compounds 1, 2, 3 or 4 (500 nM, every 48 hrs for 25 days, Example 7) using standard cell culture conditions described above did not show a decrease in cell viability.

Cytotoxicity is also associated with increased expression of apoptosis marker genes, such as Bax and Fos. On the basis of qPCR analysis, we were unable to detect gene expression of typical apoptosis biomarkers (i.e., Bax and Fos) in C2C12 cells treated with compounds 1, 2, 3 or 4 up to 25 days (500 nM or 5 µM of compound, every 48 hrs for 25 days, Example 7).

Example 10

Gene Expression in hMSCs after Treatment with Compound 3

In the presence of matrix (5 mg/mL) the effect of 3 (500 nM) on target mRNA expression in hMSC cells was unexpectedly synergized (as determined by qPCR). Runx2 and BMP-2 are osteogenic markers; Axin2, Wnt3a, and Sox 9 are Wnt-inducible gene markers. Gene expression was analyzed after three days treatment (as described in Example 7) (Table 9). In the presence of matrix, Runx2 and BMP-2 mRNA expression (8.2- and 7.5-fold respectively) correlated with osteogenesis. During this three-day interval, Wnt repressor gene Axin2 was dramatically decreased (80% decrease) by 3 treatment, while other Wnt inducible markers such as Wnt3a and Wnt5a were up-regulated 82.4-fold and 6.3-fold, respectively. Sox9 expression decreased 40%. Compared to the effect of 3 on hMSCs in the absence of matrix, generally, an increase in gene expression was observed for cells treated with 3 in the presence of matrix (synergistic increases in BMP-2 expression and a marked synergism for Wnt3a expression).

TABLE 9

Effect of compound 3 on mRNA target gene expression in hMSCs after 3 days.

| | Fold-changes +/− SD | |
|---|---|---|
| Gene ID | −matrix | +matrix |
| Runx2 | 101.3 ± 10.0 | 8.2 ± 0.8 |
| BMP-2 | 2.6 ± 0.2 | 7.5 ± 0.7 |

TABLE 9-continued

Effect of compound 3 on mRNA target gene
expression in hMSCs after 3 days.

| Gene ID | Fold-changes +/− SD | |
|---|---|---|
| | −matrix | +matrix |
| Axin2 | ND* | 0.2 ± 0.02 |
| Wnt5a | 1 ± 0.1 | 6.3 ± 0.6 |
| Wnt3a | 1 ± 0.1 | 82.4 ± 8.0 |
| Sox9 | 0.1 ± 0.01 | 0.6 ± 0.1 |

*ND, not detectable (n = 3).
Cells were cultured for 3 days as in Example 7.

Example 11 hMSC Cell Differentiation Induced by Compounds of Formula II, IV and VI in the Presence or Absence of a Calcium Phosphate Ceramic Matrix. Protocols for the Characterization of the Transdifferentiation Process hMSCs, also known as human bone marrow-derived stromal cells with less than 6 passages were used in experiments. hMSCs were cultured at 37° C., in 5% $CO_2$ in α-MEM media supplemented with 20% heat inactivated FBS (growth media) and 1× GlutaMax.

Alkaline Phosphatase Functional Activity Assay:
The assay for ALP functional activity followed the same procedure with hMSCs as described for C2C12 cells (Example 7).

qPCR Detection of Osteogenic Markers:
The assay for mRNA expression followed the same procedure with hMSCs as described for C2C12 cells (Example 7).

Cell Proliferation/Viability Assay:
The assay for cell proliferation followed the same procedure with hMSCs as described for C2C12 cells (Example 7).

Alizarin Red S Staining:
The assay for Alizarin Red S staining followed the same procedure with hMSCs as described for C2C12 cells (Example 7).

Oil Red O Staining:
Oil Red O (ORO, 1-(2,5-dimethyl-4-(2-5-dimethylphenyl) phenyldiazenyl) azonapthalen-2-ol) was used to stain for the presence of adipocytes. An ORO solution was prepared to afford a 0.03% final concentration in $dH_2O$. hMSCs were cultured as described above for Alizarin Red Staining (Example 7) in 48-well plates. On day 25 of cell incubation, cells were fixed with 4% formaldehyde for 40 mins at room temperature. Cells were stained for 1 hr followed by washes with $dH_2O$ (1 mL) until the wash water was clear (without red elutes). Cell culture images were taken under a microscope and quantified by densitometry.

Alcian Blue Staining:
Alcian Blue staining was used to stain for the presence of chondrocytes. Alcian Blue solution (1% wt/volume, acetic acid, pH 2.5). hMSCs were cultured as described above for the Alizarin Red S Staining assay (Ex. 7) in 48-well plates. After 25 days of cell culture, cells were fixed with 4% formaldehyde (40 mins) at room temperature, stained for 1 hr followed by washing with $dH_2O$ (1 mL) until water was clear (without blue elutes). Cell culture images were taken under a microscope and quantified by densitometry.

Example 12

Figure 2:
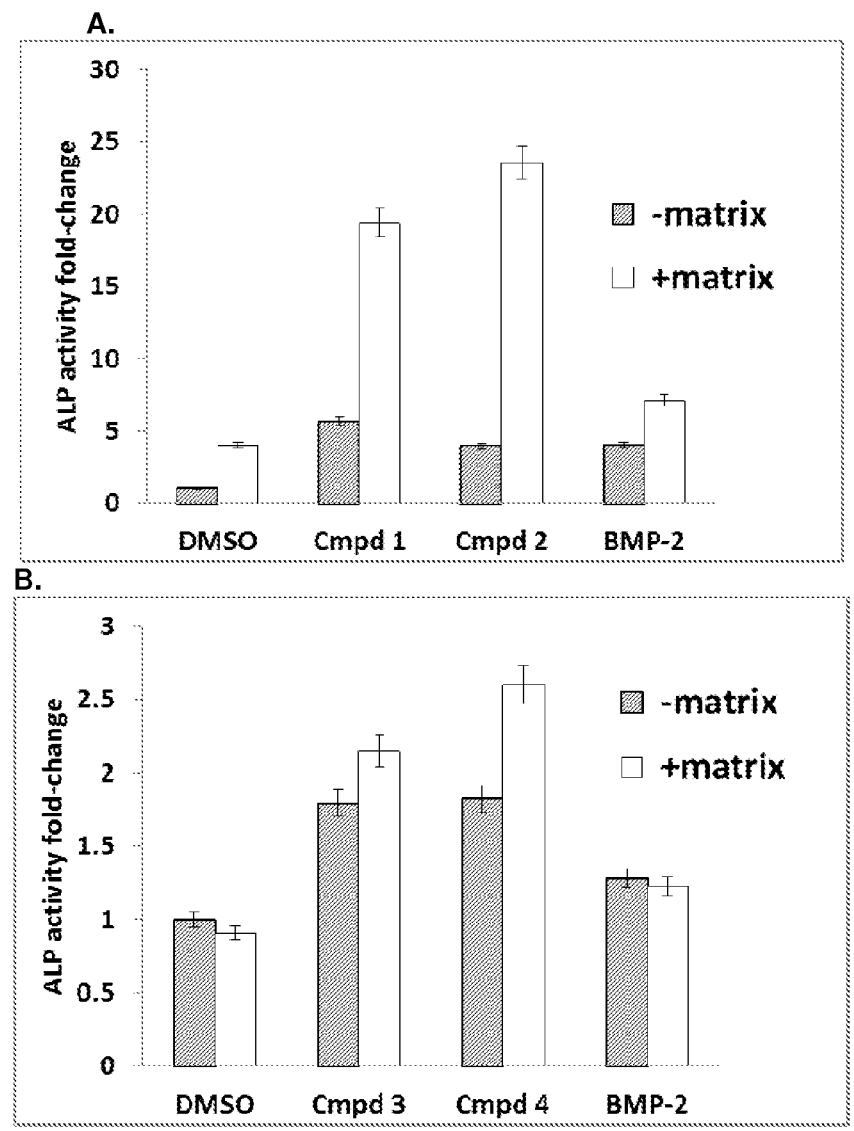
FIG. 2. A plot of the effect of compounds 1, 2, 3 or 4 (500 nM) on Alkaline Phosphatase functional activity after a 6 day incubation of C2C12 cells in the presence or absence of tricalcium phosphate ceramic matrix (5 mg/mL), that showed the combination of compound and matrix gave a synergistic increase in ALP activity compared to the effect of compound alone or matrix alone. A. Effect of compounds 1 and 2 that modulate Wnt signaling pathway. B. Effect of compounds 3 and 4 that modulate TLR signaling pathway.

Effect of 1, 2, 3, or 4 on hMSC Differentiation in the Presence or Absence of a Calcium Phosphate Ceramic Matrix Compounds 1, 2, 3, or 4 (500 nM) induced osteogenesis in hMSCs (on the basis of ALP functional activity) up to 2.6-fold greater than DMSO-treated cells. Compounds 1, 2, 3, or 4 induced ALP activity as early as day 8 and the functional activity further increased from day 8 levels to day 25 of treatment (Table 10 and FIG. 2). After 8 days of incubation of hMSCs with 1, 2, 3, or 4 (500 nM) in the presence of matrix (5 mg/mL), osteogenesis was induced on the basis of ALP functional activity up to 4.5-fold greater than cells treated with calcium phosphate matrix alone (Table 10 and FIG. 2). Compounds 1, 2, 3, and 4 in the presence of matrix all induced ALP activity as early as day 8 and the functional activity further increased over day 8 levels by day 25 of treatment. Surprisingly, for compounds 1, 2, 3, and 4 in the presence of matrix, the increase in ALP activity significantly (p<0.005) exceeded the ALP activity of cells incubated with compound alone or matrix alone. The induction of ALP activity was dose-dependent with an $EC_{50}$ of 26 nM for compound 1, an $EC_{50}$ of 140 nM for compound 3, and an $EC_{50}$ of 130 nM for compound 4.

Incubation of hMSCs with compounds 1, 2, 3, or 4 (500 nM), induced expression of osteogenic biomarkers (i.e., ALP mRNA) by up to 5-fold over DMSO-treated cells (Table 11) (8 days of cell culture described in Example 11).

After 8 days of incubation of hMSCs with compound 3 (500 nM), expression of osteogenic biomarkers ALP and Collagen I was increased by 4.0-fold and 1.5-fold over vehicle (i.e. DMSO)-treated cells (Table 11).

TABLE 10

Effect of Compounds 1, 2, 3 or 4 on Alkaline Phosphatase activity in hMSC cells in the presence or absence of matrix.

| Time (days) | Compound 1 | | Compound 2 | | Compound 3 | | Compound 4 | |
|---|---|---|---|---|---|---|---|---|
| | −matrix | +matrix | −matrix | +matrix | −matrix | +matrix | −matrix | +matrix |
| 8 | 1.2 ± 0.1 | 1.5 ± 0.1 | 1.5 ± 0.1 | 2.6 ± 0.3 | 1.5 ± 0.1 | 1.8 ± 0.1 | 1.5 ± 0.1 | 2.7 ± 0.2 |
| 25 | 1.5 ± 0.1 | 3.6 ± 0.4 | 2.6 ± 0.3 | 4.5 ± 0.4 | 1.7 ± 0.1 | 2.3 ± 0.2 | 1.8 ± 0.2 | 4.0 ± 0.4 |

*Data = mean +/− SD (n = 3).

Incubation of hMSCs with compound 3 (500 nM, every 48 hr, Example 11) in the presence of a calcium phosphate ceramic matrix (5 mg/mL) induced osteogenic biomarkers. Compared to either the effect of treating cells with compound alone or the effect treating cells with matrix alone, VDR, ALP, Collagen I, and Osteocalcin mRNA expression was increased to a much greater extent in cells treated with 3 in the presence of matrix (500 nM 3, 8 days of treatment every 48 hr as described in Example 11). For example, VDR mRNA was increased 45-fold and ALP mRNA was increased 55-fold for hMSCs cultured in the presence of 3 and calcium phosphate matrix. The conclusion is that small molecule 3 induced osteogenesis in hMSCs, but in the presence of the calcium phosphate ceramic the response is surprisingly increased because robust mRNA up-regulation of VDR or ALP in the presence of highly purified curcumin (i.e., 38) or BDC (i.e., 54) was not observed. There is an unexpected optimal interaction between 3 and cells and matrix to afford robust osteogenesis.

TABLE 11

Effect of compounds in the presence or absence of matrix on target gene expression in hMSCs.

| Gene | Fold-Change +/– SD by Compound 3* | |
|---|---|---|
| | –matrix | +matrix |
| VDR | 5.0 ± 0.5 | 45.0 ± 5.0 |
| ALP | 4.0 ± 0.4 | 55.0 ± 5.0 |
| Collagen I | 1.5 ± 0.2 | 1.8 ± 0.2 |
| Osteocalcin | 0.5 ± 0.1 | 5.2 ± 0.5 |

*Data = mean +/– standard deviation (n = 3).

Figure 3:
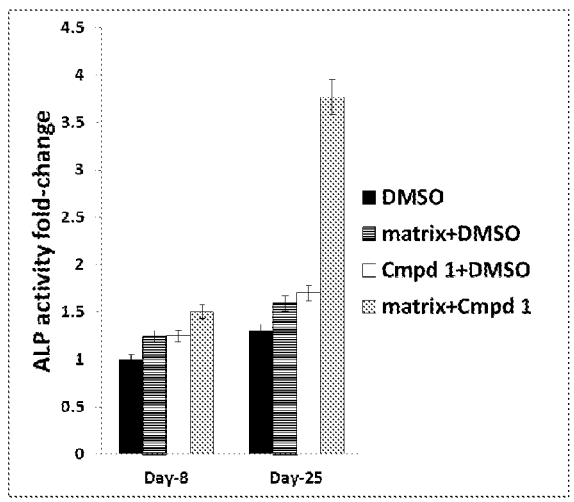
FIG. 3. A plot of the effect of compounds 1, 2, 3 or 4 (500 nM) on Alkaline Phosphatase (ALP) functional activity after 8 and 25 day incubations of hMSCs in the presence or absence of tricalcium phosphate ceramic matrix (5 mg/mL), that showed that the time-dependent effect of compound and matrix exceeded the effect of compound alone or matrix alone. A. Compound 1. B. Compound 2. C. Compound 3. D. Compound 4.
Figure 3:
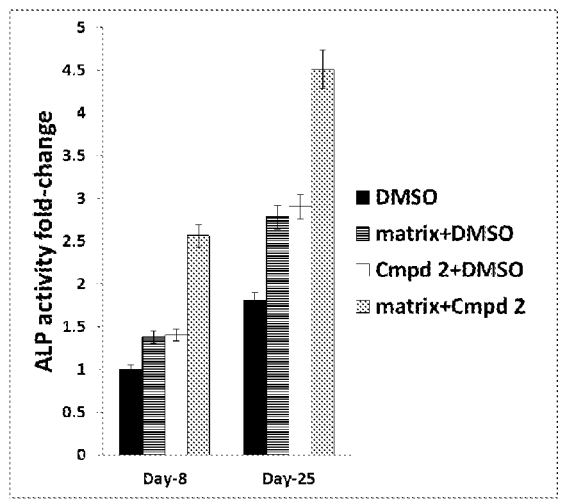
Figure 3:
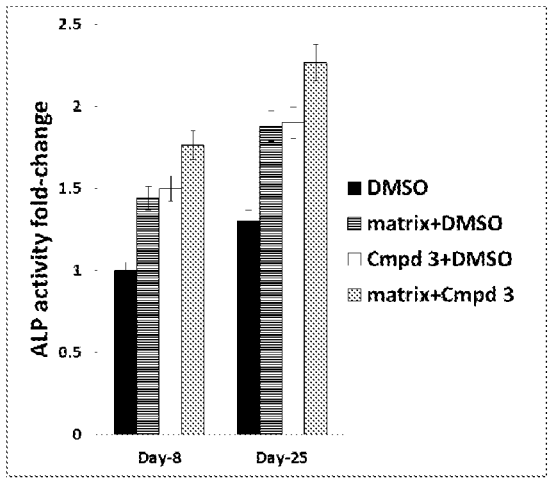
Figure 3:
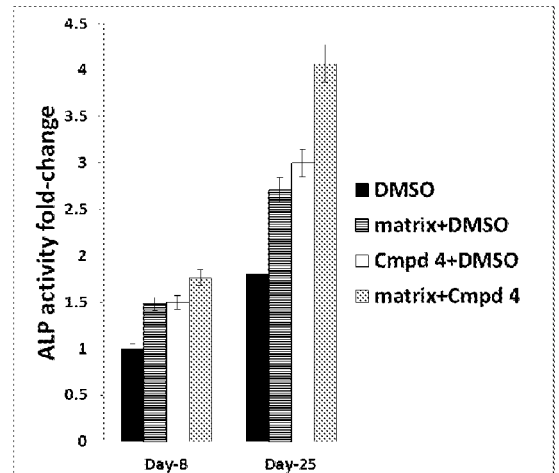

Incubation of hMSCs with compounds 3 or 4 in the presence or absence of matrix (25 days, treatment every 48 hr, Example 11) showed marked increases in calcium deposition as determined by Alizarin Red staining. Treatment of hMSCs with 3 or 4 (500 nM) increased calcium deposition 2.0-fold and 2.1-fold respectively; treatment of hMSCs (500 nM) with compound 3 or 4 in the presence of matrix increased calcium deposition by 4.2-fold and 4.0-fold respectively (FIG. 3). The calcium deposition results are consistent with ALP functional activity and mRNA osteogenic biomarker expression in that the presence of compound 3 or 4 and matrix increases osteogenesis in far excess over treating hMSCs with compound alone or matrix alone.

Compounds 3 and 4 did not promote adipogenesis of hMSCs as determined by Oil Red O staining. Oil Red O stain detects adipocytes that are a native lineage of hMSCs. Compared to vehicle (i.e., DMSO)-treated hMSCs, incubation of hMSCs with compounds 3 or 4 in presence or absence of matrix absence of matrix resulted in no increase in adipogenesis, as determined by Oil Red O staining after 25 days. Quantification of the cell culture images by densitometry showed that the effect of compounds 3 and 4 (500 nM, every 48 hr for 25 days, Example 11) in the presence of TCP (5 mg/mL) was modestly inhibitory to adipogenesis.

Compounds 3 and 4 did not promote chondrogenesis of hMSCs as determined by Alcian Blue staining. Alcian Blue stain detects chondrocytes that are a native lineage of hMSCs. Compared to vehicle (i.e, DMSO)-treated hMSCs, incubation of hMSCs with compounds 3 or 4 in presence or absence of matrix resulted in no increase in chondrogenesis, as determined by Alcian Blue staining after 25 days. Quantification of the cell culture images by densitometry showed that the effect of compounds 3 and 4 (500 nM) in the presence of TCP (5 mg/mL) was modestly inhibitory on chondrogenesis compared to vehicle (i.e., DMSO)-treated hMSCs. The conclusion is that treatment of hMSCs with 3 or 4 in the presence of matrix selectively commits the cells to bone lineage and not to fat or chondrocyte cells.

Example 13

Lack of Toxicity of hMSCs to Compounds

An Alamar blue assay of 25-day-old hMSCs cells that had been incubated with compounds 1, 2, 3, or 4 (500 nM) using standard cell culture conditions described above showed no decrease in cell viability.

After administration of compounds 1, 2, 3, or 4 to hMSCs showed no cytotoxicity as determined by quantification of apoptosis. In hMSCs, an increased expression of apoptosis mRNA biomarker genes such as Bax and Fos is associated with cytotoxicity. Based on qPCR analysis, we were unable to detect gene expression of typical apoptosis biomarkers (i.e., Bax and Fos) in hMSCs individually treated with compounds 1, 2, 3 or 4 for up to 25 days (500 nM to 5 µM of compound). This result showed that cell proliferation or differentiation or calcium deposition that is induced in hMSCs over 25 days in the presence of compound 3 or 4 was not due to a toxic insult to the cells that could potentially give rise to dystrophic events including calcification and that the observed calcium staining was attributed to the mineralized matrix deposition of maturing osteoblasts.

Example 14

Induction of Cell Migration and Localization of hMSCs to a Calcium Phosphate Ceramic Matrix Using Compounds 1, 2, 3, or 4

Human MSC migration to the site of bone injury is an important part of the repair process. Studies of hMSC migration using a transwell migration system showed that hMSCs incubated in the presence of compound and matrix increased cell migration onto the matrix. hMSCs were pre-treated with compounds (500 nM) for 8 hrs before the migration assay. After 8 hrs, compounds were washed off the cells and cells placed in a traditional transwell migration system. The top reservoir contained serum-free DMEM and the bottom reservoir contained DMEM plus 2% FBS. After incubation overnight, non-migrated cells were removed, migrated cells (stuck in the bottom chamber) were then fixed with 70% EtOH (40 mins) and total migrated cells were counted under a microscope after staining with 1 mg/mL of crystal violet (1 hr). hMSCs treated with compound 2 (500 nM, 8 hr) induced a 10-fold greater cell migration to the matrix than DMSO-pre-treated cells under the conditions described above. In a separate experiment, matrix that was pre-coated with compound 4 (as prepared in Example 5) was placed in the bottom chamber and migration of hMSCs from the top chamber was evaluated. Compound 4-coated matrix induced a 2-fold increase in cell migration to the matrix compared to DMSO-treated cells.

hMSC migration was analyzed by using calcium phosphate matrix that had been pre-adsorbed with compounds 1 or 2 (500 nM, as described in Example 5) and studied in the transwell system (2% serum, described above). Compound 1 and 2 induced 3.5-fold and 1.9-fold more cell migration than non-coated ceramic. While non-limiting, these examples show the utility of the approach for increased cell migration and localization to the calcium phosphate ceramic matrix when compounds of the disclosure are present. Use of compounds of Formula II, IV, and VI to pre-coat the ceramic and also pretreat the cells is also of utility.

Example 15

TLR Expression in hMSCs Induced by Compounds 1, 2, 3, or 4

TLRs are modulators of hMSC differentiation. TLRs (TLR1-10) mRNA could be detected by qPCR in hMSCs. TLR4 is a biomarker for osteogenesis and TLR3 is a biomarker for adipogenesis. After co-culturing hMSCs with compounds 1, 2, 3 or 4 for 8 days and quantifying TLR mRNA by qPCR, the ratio of TLR4/TLR3 expression was determined as an indicator for osteogenesis over adipogenesis. Compounds 1, 2 and 3 (500 nM) induced a modest increase in TLR4/TLR3 ratio. What was unexpected was that under similar conditions, in the presence of calcium phosphate matrix, a 5- to 9-fold increase in TLR4/TLR3 ratio was observed supporting the observation that the osteogenic activity of cells treated with compounds of Formula II, IV or VI was dramatically increased in the presence of matrix. We also observed a 3- to 4-fold increase in the TLR4/TLR3 gene expression ratio in E15 cells under otherwise identical conditions.

Example 16

Protocol for Culturing ESCs, Promoting Cell Differentiation, and Characterizing the Differentiation Process Human embryonic stem cells E15 (hESCs) obtained from ATCC with less than 15 passages were cultured at 37° C. in 5% $CO_2$ in DMEM media supplemented with 15% heat inactivated FBS and 1× GlutaMax. TLRs are biomarkers of stem cell differentiation. TLR4 expression is an osteogenic biomarker and TLR3 expression is an adipogenic biomarker. After culturing hESCs for 8 days in the presence of test compounds under standard cell culture conditions described above, isolation and quantification of TLR mRNA by qPCR showed marked changes in TLR expression levels. Using a ratio of TLR4/TLR3 as a biomarker for osteogenic induction in hESCs that is induced by compound treatment, we observed compound 3 and 4 (500 nM) induced an increase of TLR4/TLR3 ratio by 2-fold.

Similarly, after culturing hESCs with compounds 3 or 4 (500 nM) for 8 days, induction of osteogenic mRNA biomarker expression (Collagen I) in hESCs was 1.7-fold to 5-fold greater compared to cells treated with DMSO. The results suggest that compounds of Formula VI, such as compounds 3 or 4, act in part by modulating TLR signaling to promote osteogenesis of hMSCs.

Example 17

Effect of Compounds on Allogeneic Cells and Allograft Tissues to Promote Differentiation Demineralized allogeneic bone chips were thawed at 37° C. quickly with gentle agitation, washed with Dulbecco's PBS (DPBS) and centrifuged at 600×g for 5 min at room temperature. The material was digested with a collagenase and the mixture was filtered through a 100 m cell strainer and the remaining bone fragments were rinsed with DPBS. The released cells were centrifuged at 1,200×rpm for 5 min at room temperature, resuspended and plated in 10 mL α-MEM media plus 20% FBS plus 1× Glutmax. After three days at 37° C. and 5% $CO_2$, the TCP matrix (5 mg/mL) was added followed by compound 1 (500 nM) (or other compounds of Formula II, IV or VI) and the cell culture media was replaced every two days with fresh media-containing compound for 8 days. Cells were harvested after 8 days for determination of ALP activity, osteogenic mRNA biomarkers (i.e., VDR and collagen I), and cell proliferation. Cell proliferation increased 2.5-fold. VDR and collagen I mRNA expression increased 4.5-fold and 2.2-fold, respectively. Similar to isolated hMSCs in the presence of matrix, allograft-derived cells also respond to the presence of compounds and matrix to afford osteogenesis. The cells can be used in implantation as described in Examples 19 and 20.

Example 18

Prodrug Properties of Compound 3 that Promotes Osteogenesis

Compound 3 was a bis(amino acid) prodrug of a naturally occurring curcumin 54 (also known as, bisdemethoxycurcumin). The bis(amino acid) prodrug 3 imparted solubility of greater than 10 mg/mL in water, while the parent compound 54 was only sparingly soluble. 3 provided 54 (described in Example 3) through prodrug hydrolysis as determined by HPLC.

At pH 6.5 PBS, compound 3 persisted over 77 minutes with a half life of hydrolysis of 23 minutes. Within 5 minutes, the hydrolysis of 3 produced compound 84 (described in Example 3) that is the mono hydrolysis product of the bis(amino acid) pro-drug 3. Within 15 minutes, compound 54 that is the fully hydrolyzed product from 3 (and 84) was prominent in solution. By 77 minutes, most of 3 was hydrolyzed while compound 84 and compound 54 persisted. Thus, the results show the compound 3 persists for over an hour in pH 6.5 phosphate buffer (10 mM), but not in pH 7.5 buffer, and is capable of delivering compounds 84 and 54 into solution.

Compound 3 and compound 54 were compared for biological activity. C2C12 cells were incubated with either compound 3 or 54 (50 nM) and after 3 days cell proliferation was determined by an Alamar Blue Assay, using protocols described above. Compound 3 gave a 4-fold increase in cell proliferation while compound 54 gave a 2-fold increase. These results and others showed that biological activity of water-soluble compound 3 was different from the biological activity of compound 54 that is the prodrug hydrolysis product of 3 in aqueous media.

From these results a general protocol was derived for administering compound 3 to cells. First, cells were incubated with compound 3 in pH 6.5 phosphate buffer (10 mM) for 40 minutes to prolong the presence of 3 and 84 in solution. Following 40 minutes, cell culture media (e.g. DMEM with 20% FBS at pH 7.4) was added in equal volume to the incubation. After 48 hours, the cell culture media is removed and fresh pH 6.5 phosphate buffer (10 mM) containing compound 3 was added to the cells to start another iteration of compound treatment.

Example 19

Surgical Implants of Osteogenic Cell Products Using the Materials of the Invention GMP grade hMSCs are seeded at a density of 1840 cells/$cm^2$ in growth media (α-MEM, 20% FBS, 1× GlutaMax). After 24 hours incubation, cells were treated with compounds of Formula II, IV, or VI (and in particular 3 (500 nM)) in the presence of the calcium phosphate ceramic matrix (5 mg/mL). For compound 3 treatment, cells were incubated in PBS buffer (12 mM, pH 6.5, 40 mins) for 40 minutes. An equal volume of hMSC culture medium was then added to cell incubations with 3 and media was replaced every 48 hrs for 8 days. On day 8, the cell-ceramic-compound mixture was washed with PBS (50 mM, pH 7.4, $Ca^{+2}$-free) once and the cells were trypsinized with 0.5× trypsin-EDTA for 4-5 minutes. The cells obtained were pelleted at 500×g (3 mins) to remove trypsin and residual compound 3. Three washes are done before freezing the re-suspended cells and calcium phosphate ceramic matrix (from cell culture) in cryopreservative (20% FBS, 5% DMSO, α-MEM, 1× GlutaMax). On the day of use, the cell-matrix mixture is thawed, washed with PBS, and pelleted by centrifugation. The induced cell-ceramic composition is reconstituted in either patient blood or serum sample, or in Ringers solution, using a syringe to mix with the appropriate formulation of cells and calcium phosphate ceramic matrix. A cellular adhesive is optionally combined with the induced hMSCs/matrix composition before addition of the mixture to a surgical cage for delivery with appropriate surgical instrumentation and devices. Using this procedure, highly osteogenic cells committed to the bone lineage were prepared and are delivered to the animal (preferably human patient) by a surgeon using the techniques of the field, for example by addition of the compositions to PEEK surgical cage specifically designed for use in spinal fusion procedures.

Example 20

Preparation and Transplantation of the Compositions of the Invention (Intramuscular Osteoinduction)

Figure 5:
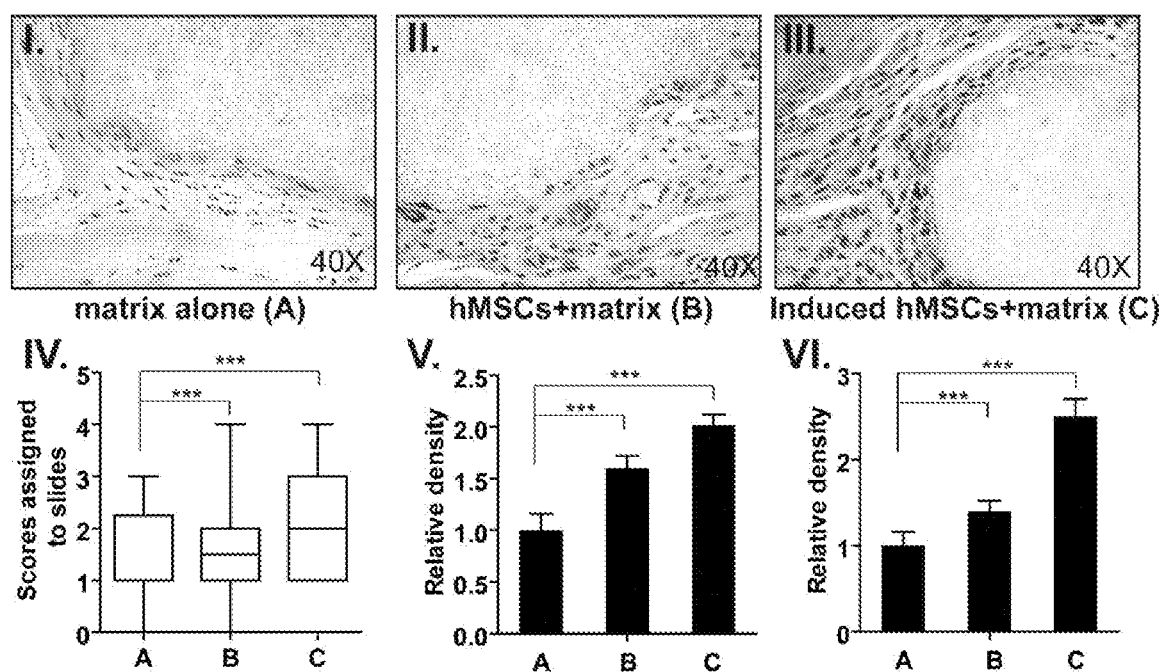
FIG. 5. A series of histological images of H&E stained tissue sections of implants placed intramuscularly in immunodeficient mice 8-weeks post-implantation and their analysis. I-III. A series of higher magnification (40×) images of tissue sections that received matrix alone (I), hMSCs and matrix (II), and small molecule-induced hMSC and matrix (III), showing that the induced hMSC and matrix implant gave increased osteoid formation and cell density on the periphery of granules. IV. H&E stained tissue sections of the implants scored by blinded, trained observers for the intensity of stained tissue peripheral to the implanted TCP granules. Scoring results shown in a Box and Whisker Plot with a $75^{th}$ percentile (box) and median (line), that showed that the induced hMSC-matrix implants gave more osteoid formation. Images were scored from 0-4, where 0: no osteoid, 1: thin and/or discontinuous regions of osteoid, 2: thin regions of osteoid on the periphery of the granules, 3: thick or dense regions of osteoid on the periphery of the granules, 4: robust regions of osteoid on the periphery of the granules. V. Quantification of H&E stained tissue sections at 4× magnification of the implants by densitometry analysis using image analysis software, showed that the small molecule-induced hMSC-matrix implants gave more osteoid formation. Data were means±SD (n=6). VI. Quantification of the histology images shown in FIG. 4A through 4C (40× magnification) by densitometry analysis using image analysis software, that showed improved osteoid density from small molecule-induced hMSC-matrix implants. Data are means±SD (n=6). Statistical analysis is done with student t-test (***p<0.001).
Figure 6:
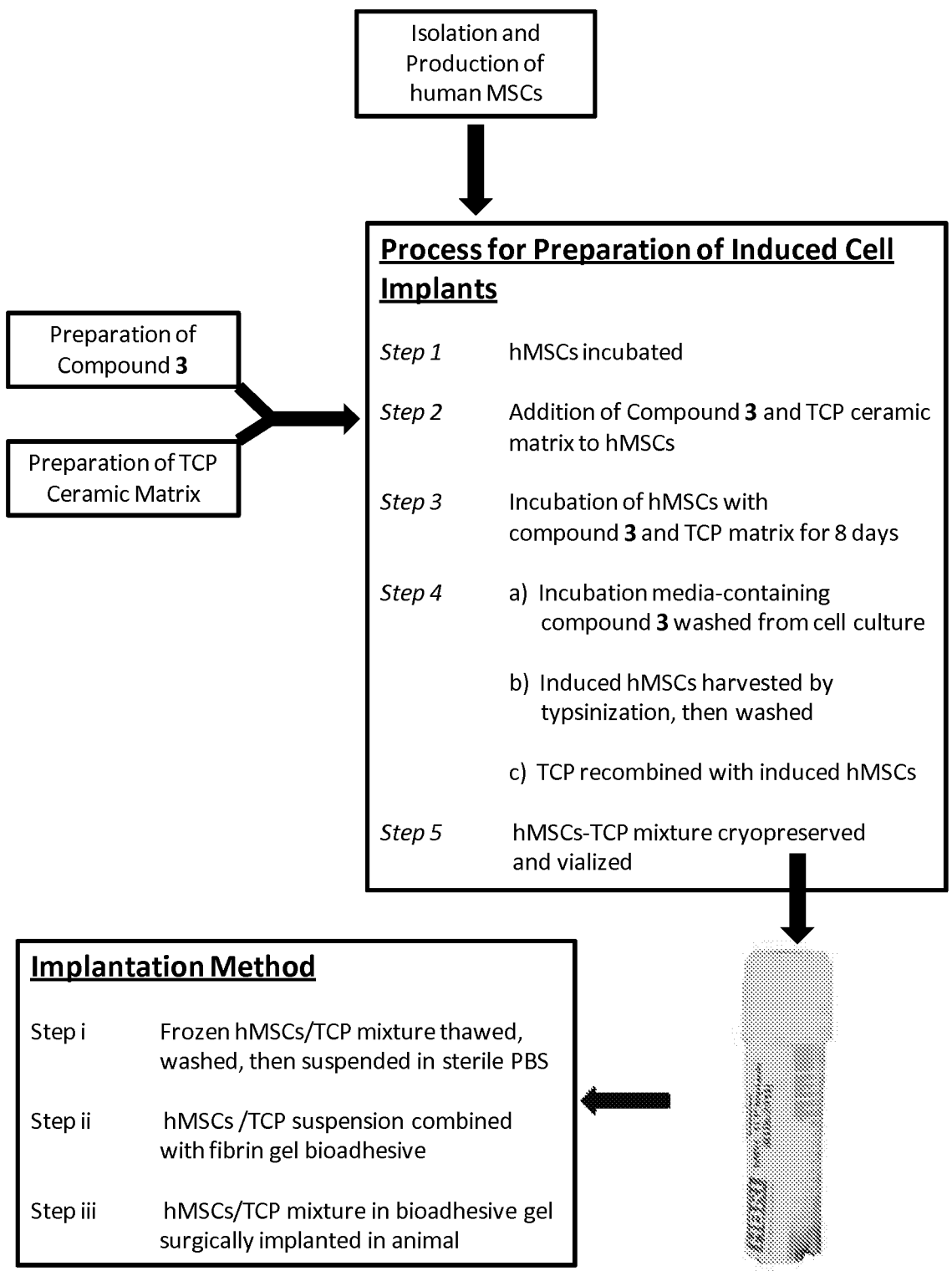
FIG. 6. A high-level flow diagram that depicted a representative process for the preparation of small molecule-induced hMSC-TCP implants (Steps 1-5) and a representative method for how the implants are used (Steps i-iii).

Induction of hMSCs with Compound 3 in the Presence of TCP Ceramic Matrix (FIG. 5, Steps 1-3).

hMSCs (i.e., less than five passages) were seeded at a density of 17,500 cells/well in 6-well plates and cultured for 8 days under various conditions before implantation in mice. Mice were divided into groups according to the experimental design: i) uninduced hMSCs that were treated with vehicle alone (i.e., 0.1% DMSO, final concentration) for 8 days then combined with TCP ceramic matrix, and ii) induced hMSCs that were treated with 3 (500 nM) in the presence of TCP ceramic matrix (5 mg/mL) for 8 days, and iii) TCP ceramic matrix (i.e. no cells) mock cultured for 8 days. The TCP ceramic matrix used was 500-100 μm granules. To prepare compound-induced cells, hMSCs were incubated with compound 3 in the presence of TCP ceramic matrix (5 mg/mL) on day 0, and the media was replenished every 48 hours. To administer compound 3 to cell culture, cells were washed with 1 mL PBS (50 mM, pH 7.4) and then 1 mL of PBS (10 mM, pH 6.5) containing compound 3 (1000 nM) was added. Compound 3 was applied for 40 minutes. MEM medium was added to existing PBS (pH 6.5) cell incubations to effect a 500 nM final concentration.

Isolation of Compound-Induced hMSCs and their Cryopreservation (FIG. 5, Steps 4-5).

At the end of an 8-day cell culture period, the cells were washed three times with 1 ml PBS (50 mM, pH 7.4), and removed from the 6-well plate by trypsinization. For induced cells, the TCP granules that remained on the plate were retained. After three washes with PBS (50 mM, pH 7.4), cells were centrifuged at 1200×g for 3 min. The cell pellet was recombined with TCP ceramic taken from cell culture and the mixture was suspended in 1 mL freezing medium (MEM essential containing 20% FBS and 5% DMSO). Before cryopreservation of the cell-TCP mixture in liquid nitrogen, a 10 μl aliquot of each sample was taken and used to count the cells, or to confirm ALP functional activity and mRNA biomarker expression (i.e., Osteocalcin, Collagen I) in advance of implantation.

Preparation of Implants for Surgery (FIG. 5, Steps i and ii).

On the day of surgery, implants comprised of either i) TCP ceramic matrix, ii) hMSCs (0.5 million) and 5 mg TCP ceramic matrix, or iii) compound-induced hMSCs (0.5 million) and 5 mg TCP ceramic matrix were prepared for transplantation. Frozen cell/ceramic suspensions were thawed and washed three times with PBS (50 mM, pH 7.4). All implants were combined with a bioadhesive just prior to implantation in mice. Implants of cell-matrix mixtures (induced or non-induced with 3), or TCP matrix alone, were each re-suspended in 10 μl of a 0.16 mg/μl fibrinogen solution and then 10 μl of a 0.036 mg/μl thrombin solution was added. Immediately after addition of thrombin, a core Fibrin mesh structure formed. The cell-ceramic suspension in Fibrin gel was immediately used for implantation in the animal.

Surgical Implantation of Compositions of the Invention (FIG. 5, Step iii).

Ten-week old nude, immunodeficient Bg-Nu-XID female mice (20 g) were used as implant recipients. Mice were acclimatized in a pathogen-free facility for two-weeks prior to implantation surgery. Fourteen mice were given a total of 28 bilateral intramuscular implants in the biceps femoris. Mice were divided into experimental groups that received implants of: i) TCP matrix alone (n=3 mice, 6 implants), ii) implants of hMSCs+TCP matrix (n=5, 10 implants), and iii) implants of compound-induced hMSCs+TCP matrix (n=6, 12 implants). For surgery, mice were anesthetized by a single ip injection of a mixture of ketamine (100 mg/kg) and xylazine (7.5 mg/kg) in sterile saline. Mice were monitored throughout surgery and thereafter for maintenance of the surgical plane of anesthesia. The surgical area on each hind limb was cleaned with Betadine. Bilateral surgical incisions of approximately 1-2 cm in length were made longitudinally in the dorsal hind limbs. Pockets were made in the biceps lemons muscles by blunt dissection parallel to the muscle fiber long axis. For each mouse, the cell-ceramic implant was placed in the muscle pouch using sterile forceps, and the fascia was sutured with 5-0 Vicryl absorbable sutures. The incision site skin was closed using surgical wound clips. Animals were given antibiotics Trimethoprim/Sulfamethoxazole (0.05% and 0.01% by weight) in the drinking water for up to 5 days post-surgery. Wound clips were removed within 1-week post-surgery, upon visual confirmation of healing of the incision site. After 8 weeks, mice were euthanized for histological evaluation. Explants of the muscle tissue containing the implants were immediately fixed in freshly prepared 10% neutral buffered formalin (10% NBF) over 48 hours at 21° C.

Histomorphological and Radiographic Studies.

Prior to histological processing, explants were radiographed in a consistent orientation by reference to a suture placed in each tissue during necropsy. Radiographs were obtained with a hard tissue standard (steel ruler) and an osteological standard (rat fibula), at 22 kv for 20 seconds, using a Faxitron X-Ray. Radiographs confirmed that the implants remained cohesive (i.e. the TCP matrix granules remained together) after 8 weeks.

For histological processing and slide preparation, specimens were dehydrated by a graded series of ethanols, transferred to glass vials, and immersed in methyl methacrylate (MMA). After a period of three days, a mixture of MMA and 0.5% anhydrous benzoyl peroxide was infiltrated into specimens to drive polymerization. The embedding pots were then placed in a water bath (29-33° C.) until fully polymerized (3-10 days). From each embedded specimen at room temperature, three 4-μm sections were cut using a Polycut slab microtome and mounted on glass slides in 70% ethanol and air-dried. Specimen orientation was determined using the radiographs and visual inspection of a suture placed during necropsy. Sections were taken from approximately the mid-line of the implant, through the longest axis of the radio-opaque implant material, and one from each side (more superficial and deeper to the mid-line) spaced approximately 200 μm from the mid-line. Sections were mounted on slides so that suture orientation was toward the slide label. Mounted sections were stained with a hematoxylin and eosin (H&E) stain. The stained mounted slides were cover slipped using one drop of DPX mounting medium and air-dried.

Figure 4:
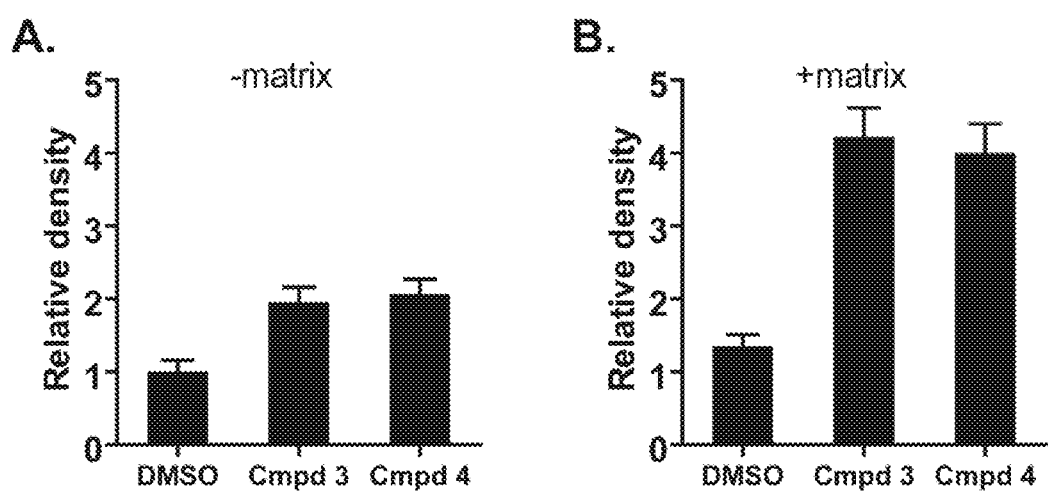
FIG. 4. A plot of the effect of compounds 3 or 4 (500 nM) on calcium deposition from hMSCs that were incubated in the presence or absence of matrix (5 mg/mL) for 25 days. A. Quantification of Alizarin Red S staining of hMSCs after 25 days incubation with 3 or 4 in the absence of matrix, that showed compound 3 or compound 4 increased calcium deposition in hMSCs. B. Quantification of Alizarin Red S staining of hMSCs after 25 days incubation with 3 or 4 in the presence of matrix, that showed 3 or 4 in the presence of matrix increased calcium deposition more than the combined effects of compound alone and matrix alone. Quantification of the stained cell cultures was conducted by densitomy analysis using image analysis software. Data are means±SD (n=6).

Digital images of slides were obtained at 4× magnification using an EVOS®XL Core Cell Imaging System. A region of interest (ROI) was cropped from the composite digital images that represented the area surrounding the location of the implanted TCP granules. Blinded, trained observers were asked to score the ROI, with emphasis on the regions proximal to the granules. A semiquantitative scoring system was used: 0—no osteoid in the ROI, 1—thin or discontinuous regions of osteoid in the ROI, 2—a thin film of osteoid in the ROI, 3—a thick or dense osteoid distribution in the ROI, and 4—for robust osteoid formation in the ROI. Three independent observers scored the slides and the full data set was depicted in non-parametric form using a Box and Whisker plot (FIG. 4, IV). For the induced hMSC implants that were prepared by culturing hMSCs in the presence of compound 3 and the TCP ceramic matrix for 8 days, blinded observers rank this group as having more osteoid tissue in the ROI. Both the median score and the $75^{th}$ percentile of the scores were significantly (p<0.005) higher than implants comprised of non-induced hMSCs on TCP matrix, or TCP matrix implants alone.

Densitometry analysis of the microscopic images was done by manual selection of the osteoid tissue in the ROI compared to the total area of the ROI that was held consistent in each slide. Total pixels of the selected osteoid tissue were counted and expressed as a percentage of total pixels in the ROI, where all images were normalized by applying a consistent cut-off filter to the background. The percent osteoid in a ROI was expressed as relative differences between experimental groups (FIG. 4, V and VI). The results of the densitometry analysis of the tissue sections confirmed the rankings described above. Induced hMSC implants that were prepared by culturing hMSCs in the presence of compound 3 and the TCP ceramic matrix for 8 days gave a 2.1-fold greater osteoid in the ROI than implants comprised of TCP alone, and 1.3-fold greater osteoid in the ROI than implants comprised of non-induced hMSCs and TCP ceramic matrix. Closer inspection of the ROI at 40× magnification (FIG. 4, I-III) showed dense regions of osteoid tissue surrounding the TCP ceramic matrix that are far less pronounced in groups with non-induced cells or TCP alone. Taken together, the in vivo data showed that the induction of hMSCs by the effect of compound 3 and TCP ceramic matrix during in vitro cell culture led to more robust osteogenesis upon implantation of these compositions in vivo. The findings supported the hypothesis that in vitro induction of hMSC implants using the novel compositions and methods of the disclosure gave rise to improved bone formation in vivo.

What is claimed is:

1. A composition comprising a compound and isolated cells capable of differentiating into bone cells, wherein the compound has the structure of

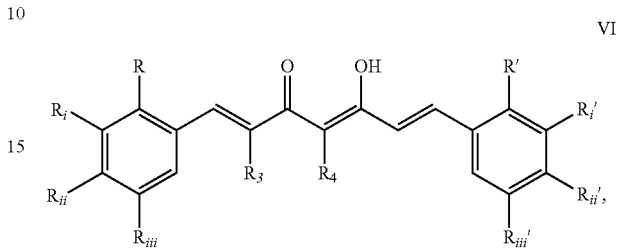

VI wherein R, $R_i$, $R_{iii}$, R', $R_i'$, and $R_{iii}'$ are hydro;
$R_{ii}$ and $R_{ii}'$ are independently selected from the group consisting of glycine-O-carboxylate, sarcosine-O-carboxylate, alanine-O-carboxylate, valine-O-carboxylate, leucine-O-carboxylate, isoleucine-O-carboxylate, phenylalanine-O-carboxylate, tyrosine-O-carboxylate, tryptophan-O-carboxylate, asparagine-O-carboxylate, glutamine-O-carboxylate, lysine-O-carboxylate, and proline-O-carboxylate; and
$R_3$ and $R_4$ are independently hydro, methyl, trideuteromethyl, trifluoromethyl, ethyl, propyl, isopropyl, butyl, sec-butyl, iso-butyl, tert-butyl, cyclopropyl, cyclobutyl, cyclopentyl or cyclohexyl, or
$R_3$ and $R_4$ are taken with an alkyl chain to define a 5-membered or 6-membered carbocyclic ring,
wherein the composition further comprises a calcium phosphate matrix, and the compound is non-covalently associated onto the calcium phosphate matrix.

2. The composition of claim 1, wherein the isolated cells capable of differentiating into bone cells are isolated human bone marrow-derived mesenchymal stem cells, human mesenchymal stem cells of adipose tissue, human mesenchymal stem cells of blood, human mesenchymal stem cells of bone allograft or autograft tissues, human mesenchymal stem cells of dental pulp, human pericytes, human myoblasts, and human chondrocytes, human osteoprogenitor cells, urine stem cells, or their respective progenitor cells, or wherein the isolated cells capable of differentiating into bone cells are as stem cells isolated from amniotic fluid or cord blood, embryonic stem cells, or induced pluripotent stem cells.

3. The composition of claim 1, wherein the calcium phosphate matrix is a tricalcium phosphate ceramic.

4. The composition of claim 1 wherein the compound is (2S,2'S)-O,O'-(3-hydroxy-5-oxohepta-1,3,6-triene-1,7-diyl) bis(4,1-phenylene) bis(2-amino-3-methylbutanoate) HCl salt, the isolated cells are human bone marrow-derived mesenchymal stem cells, and the calcium phosphate matrix is a tricalcium phosphate ceramic.

5. The composition of claim 1 wherein the compound is 4-((1E,3Z)-3-(3-((E)-4-((L-valyl)oxy)benzylidene)-2-oxocyclohexylidene)-3-hydroxyprop-1-en-1-yl)phenyl L-valinate HCl salt, the isolated cells are human bone marrow-derived mesenchymal stem cells, and the calcium phosphate matrix is a tricalcium phosphate ceramic.

6. The composition of claim 4 further comprising one or more components selected from the group consisting of bone morphogenetic proteins, fibroblast growth factors, platelet-derived growth factors, Wnt proteins, transforming growth factors, stromal derived factor-1, parathyroid growth hormone, vitamin D, 1,25-dihydroxy vitamin D, deoxycholic acid, teriparatide, ascorbic acid, ascorbic acid 2-phosphate, beta-glycerol phosphate, dexamethasone, and their respective salts.

7. A method of inducing bone formation comprising the steps of:
   (a) treating isolated cells capable of differentiating into bone cells with a compound having the structure of Formula VI of claim 1, and
   (b) administering the treated cells from step (a) to a subject.

8. The method of claim 7, further comprising the step (a') of seeding the cells from step (a) onto a calcium phosphate matrix prior to said administration of step (b).

9. A bone graft material prepared by combining isolated cells capable of differentiating into bone cells, a calcium phosphate matrix, and a compound having the structure of Formula VI of claim 1 into a surgical cage.

10. A method of inducing bone formation comprising the steps of (a) and (b) or (a) and (c), wherein the steps are as follows:
   (a) combining the composition of claim 1 with a bioadhesive
   (b) administering the composition of step (a) to a subject
   (c) adding the composition of step (a) to a surgical cage suitable for implantation in a subject.

* * * * *